United States Patent
King

(10) Patent No.: US 11,813,195 B2
(45) Date of Patent: Nov. 14, 2023

(54) APPLICATION OF LOCALIZED HYPOTHERMIC THERAPY TO A HUMAN HEAD

(71) Applicant: Restorear Devices, LLC, Kirkland, WA (US)

(72) Inventor: Curtis S. King, Kirkland, WA (US)

(73) Assignee: Restorear Devices, LLC, Kirkland, WA (US)

( * ) Notice: Subject to any disclaimer, the term of this patent is extended or adjusted under 35 U.S.C. 154(b) by 950 days.

(21) Appl. No.: 16/693,208

(22) Filed: Nov. 22, 2019

(65) Prior Publication Data
US 2020/0100938 A1    Apr. 2, 2020

Related U.S. Application Data

(63) Continuation-in-part of application No. 16/522,548, filed on Jul. 25, 2019, which is a continuation-in-part of application No. 16/163,479, filed on Oct. 17, 2018, now Pat. No. 11,523,941.

(60) Provisional application No. 62/573,716, filed on Oct. 18, 2017.

(51) Int. Cl.
*A61F 7/10* (2006.01)
*A61F 7/00* (2006.01)

(52) U.S. Cl.
CPC ........ *A61F 7/10* (2013.01); *A61F 2007/0005* (2013.01); *A61F 2007/0056* (2013.01)

(58) Field of Classification Search
CPC ..... A61F 2007/0002; A61F 2007/0005; H04R 1/1008
See application file for complete search history.

(56) References Cited

U.S. PATENT DOCUMENTS

| | | | |
|---|---|---|---|
| 7,335,222 B1 | 2/2008 | Tyler | |
| 2017/0099539 A1* | 4/2017 | Di Censo | G05D 23/00 |
| 2017/0201820 A1* | 7/2017 | Inoue | H04R 1/1041 |

* cited by examiner

*Primary Examiner* — Kaitlyn E Smith
(74) *Attorney, Agent, or Firm* — Brian C. Trask

(57) ABSTRACT

A heat transfer device particularly structured for application of thermal therapy from a contact surface to internal structures of a human ear. A device may be passive (pre-cooled), active (thermoelectrically active), or include elements of both. A device may be structured to apply thermal treatment from a contact surface of a contact cavity only to a localized posterior area relative to the circumference of an ear. A device may include both of a contact cavity and a bulk cavity, with heat transfer media disposed in each cavity. Typically, a bulk cavity holds at least twice the media volume contained in a contact cavity. The cavities may be disposed in fluid communication, or separated by a barrier to permit only thermal communication there-between. When a barrier between cavities is present, a device may include different heat transfer media in each cavity.

19 Claims, 61 Drawing Sheets

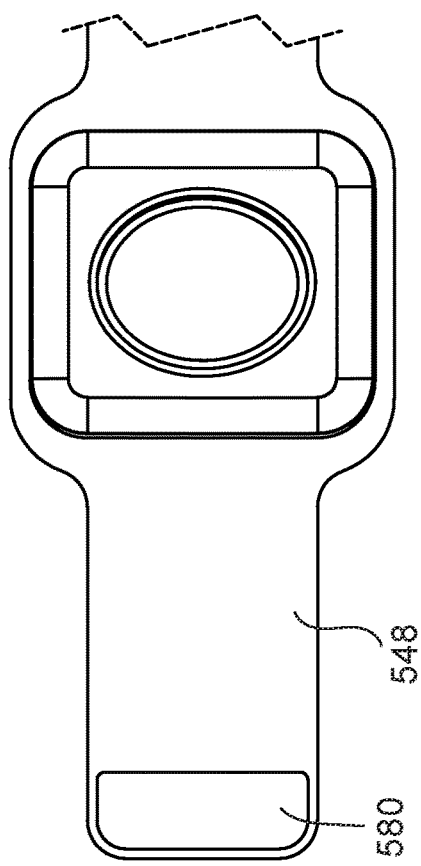
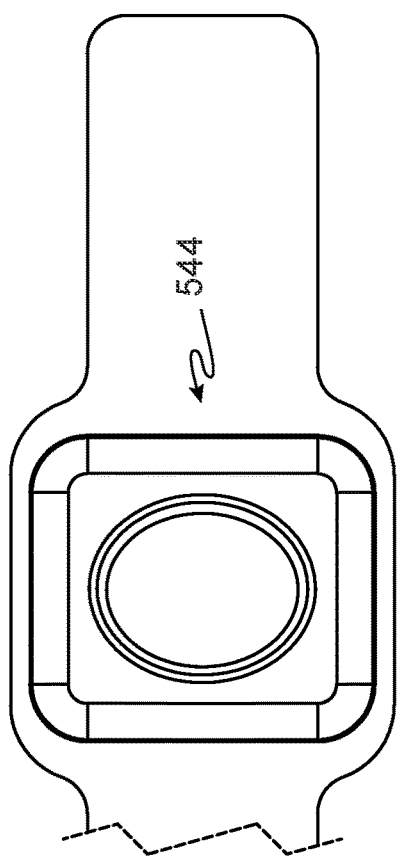
FIG. 48
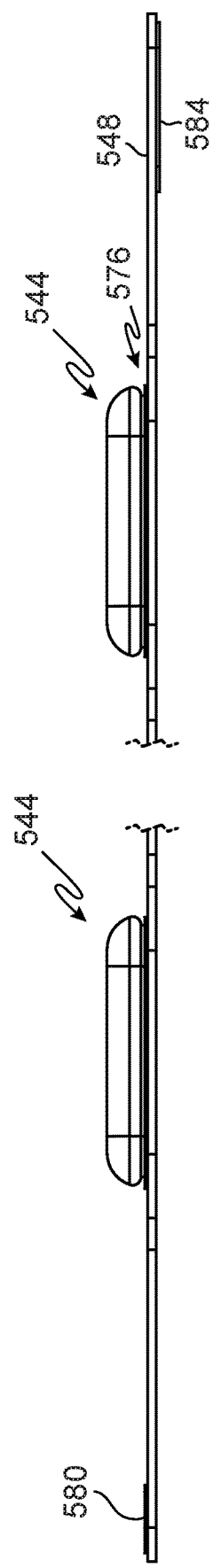
FIG. 49

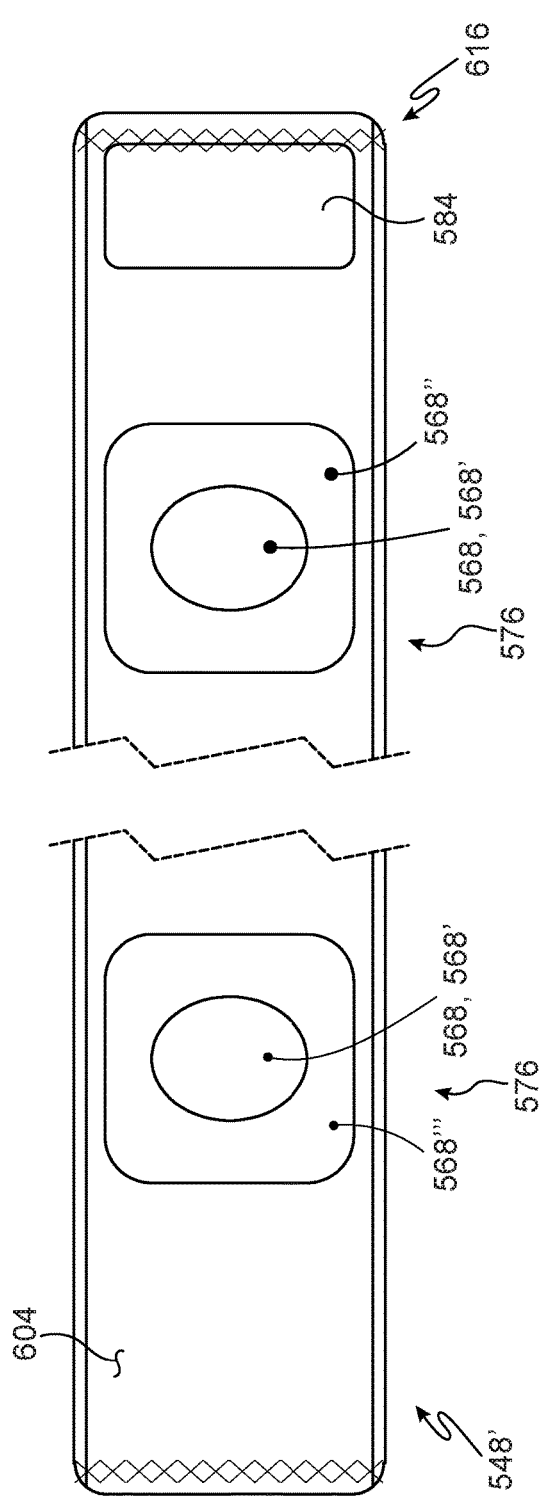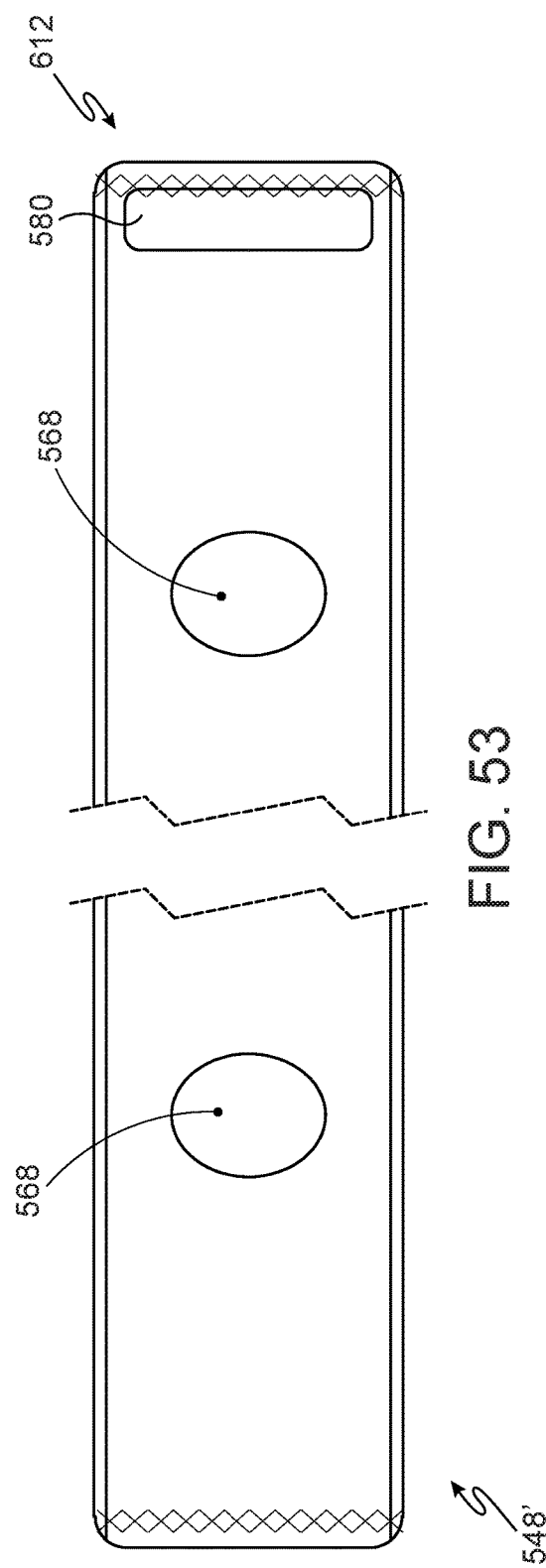

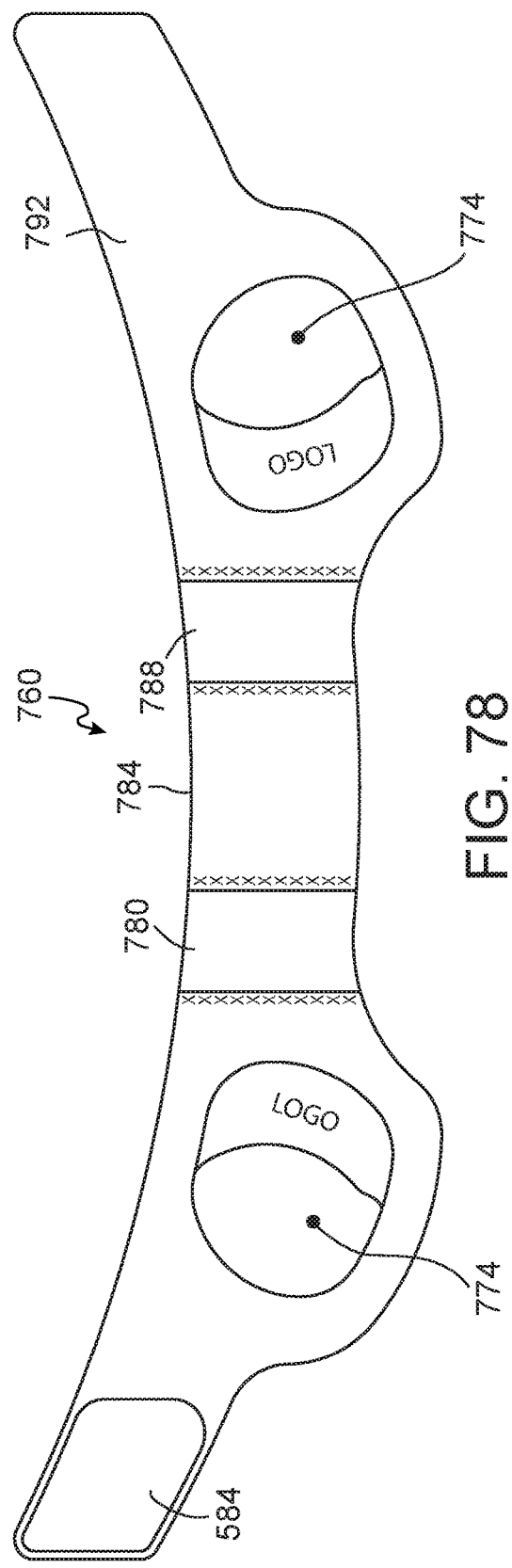
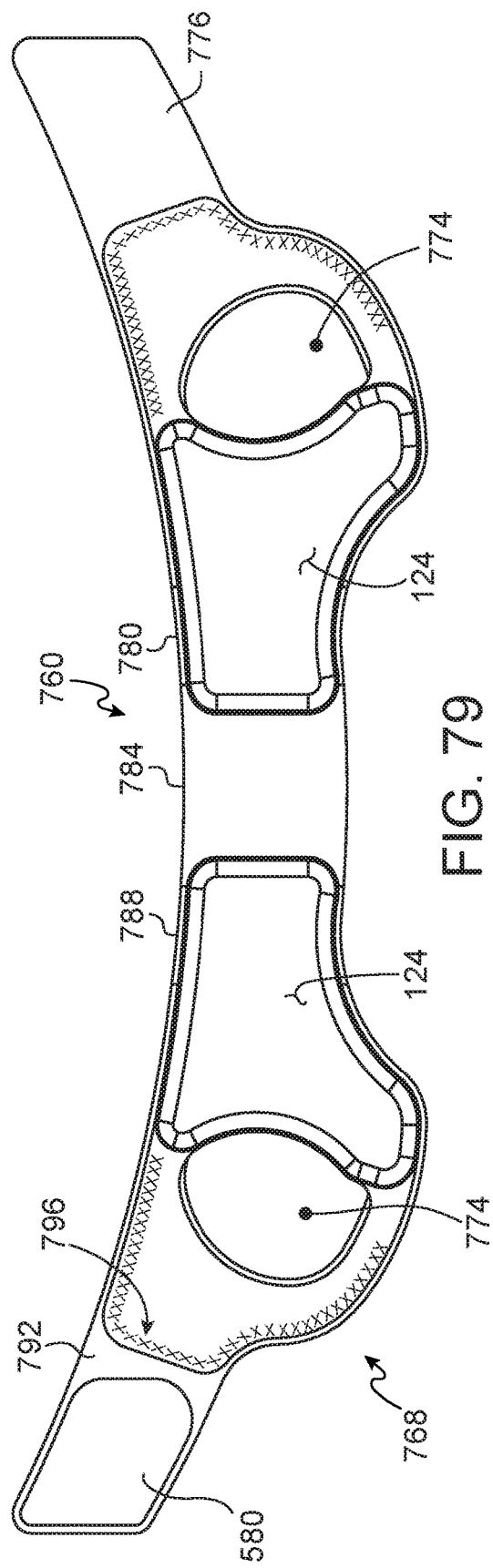

APPLICATION OF LOCALIZED HYPOTHERMIC THERAPY TO A HUMAN HEAD

RELATED APPLICATIONS

This application is a continuation-in-part of Utility application Ser. No. 16/522,548, filed Jul. 25, 2019, for "Devices for Application of Localized Hypothermic Therapy to the Human Ear", which is a continuation-in-part of Utility application Ser. No. 16/163,479, filed Oct. 17, 2018, for "Devices for Application of Localized Hypothermic Therapy to the Human Ear", and claims the benefit under 35 U.S.C. 119(e) of the filing date of Provisional Application Ser. No. 62/573,716, filed Oct. 18, 2017, for "Devices and Methods for Application of Localized Hypothermic Therapy to the Human Ear", the disclosures of all of which are hereby incorporated as a portion of this disclosure as though set forth herein in their entirety.

BACKGROUND

Field of the Invention

This invention relates to devices and methods for hypothermic therapy. It is particularly directed to devices and methods for application of hypothermic therapy to structures of a human ear that are inside the skull.

State of the Art

It has long been known that application of hypothermic therapy (i.e., "therapeutic cooling") of human body tissue can be beneficial in reducing inflammation and limiting adverse effects related to injury. Cooling therapy using e.g., ice, ice-packs, etc., has been used for centuries to treat injury. This trend continues today, and cooling therapy remains the first line of treatment for a variety of injuries. Consumer devices with different types of materials (gels, various polymeric fluids, etc.) are commercially available, and are commonly used. These devices are often designed with specific geometry or features such that the device, when installed on the human body, can efficiently cool the injured area, and reduce the severity of the inflammatory response.

In some instances, modern techniques utilizing therapeutic hypothermia have been developed, and have now become standard of care for advanced medical cases. It is commonly known that for patients suffering cardiac arrest, lowering the body temperature as quickly as possible after trauma offers significant benefits. In cases of traumatic central nervous system injuries (brain and spinal cord), localized hypothermic therapy (in these cases, referred to as Targeted Temperature Management) also shows promising results as a method for improved outcomes. Localized, or targeted application of, thermal therapy may avoid or reduce patient discomfort during the therapy.

Most recently, work in the field of otolaryngology and audiology has shown that there is a potential benefit to the use of this targeted/localized therapeutic hypothermia for the treatment of noise induced hearing loss, or hearing damage. Animal studies have shown that the application of localized cooling to the external regions of the skull nearest the ears (specifically, areas of the skull nearest the organs/structures of the outer, middle, and inner ear), following noise trauma may reduce or eliminate hearing damage. Data shows that application of this therapy may offer significant benefits for reducing hearing damage in both the long and the short term.

Considering this, there exists a need for improved devices and methods for the effective application of therapeutic hypothermia to structures in, on, or around the region of a human ear.

BRIEF SUMMARY OF THE INVENTION

Noise-induced hearing loss (NIHL) is an impairment resulting from irreversible damage to the hair cells or underlying neural structures in the cochlea as a result of noise exposure. The consequence of such damage is loss of hearing, that can occur acutely or over a period of time. The significant health problems presented by such hearing loss require development of new strategies to reduce or prevent it. We have shown that controlled and localized therapeutic hypothermia provided to the inner ear non-invasively and subcutaneously post-noise trauma conserves residual hearing. We have further shown that such a treatment may preserve sensitive neural structures against trauma. This invention provides a novel apparatus and technique that can be applied for preservation of hearing and balance during ototoxic insults, noise-exposure, traumatic brain injuries, exposures to blast, inner ear or middle ear surgeries, and chemotherapy. Cooling post-trauma can extend or postpone the critical time window of cell death by modulating multiple molecular and cellular pathways, which then allows for synergistic therapies. For example, one can envision local cooling after trauma to the ear (noise) "buying" the patient 24-48 hours. During this time, treatment can be combined with targeted drugs that are synergistic and provide a long-term benefit.

Certain embodiments structured according to the invention can be essentially described as an ice-pack for the ear. A system for treatment of a patient typically requires one thermal element or device per ear. Sometimes, a thermal device may be characterized as "passive". An exemplary passive device includes a compartment, or bladder, containing some sort of thermal "working fluid" or thermal mass. Sometimes, an embodiment may be made reference to as "active". An active device includes electronic elements to aid in cooling a localized area of a patient. Cooling devices may include both passive and active elements in workable combination. A cooling device may be structured for placement of the entire device, or only a portion thereof, into a cooling device such as a freezer to prepare a pre-chilled element for application of thermal therapy onto a patient.

In one method of use, the device(s) is/are placed into a freezer until the working fluid/mass attains a temperature significantly lower than human body temperature. With the fluid/thermal mass at low temperature, the device is placed on the skull, in a region near, or around the ear. The therapy occurs as the device cools the skull (and the auditory structures within the skull) locally, over a time period and at a rate dependent on the liquid volume, or thermal mass contained within the device.

An exemplary embodiment structured according to certain principles of this invention includes a thermal therapy device structured to interface in installed registration with an ear of a human head, the device being structured to place a heat transfer contact element in contact with the head at a localized area. In some cases, the localized area extends only partially around a circumference of the ear. Preferred devices are structured to couple with auditory headphones, so that a user may enjoy music or sonic therapy during thermal therapy sessions.

A therapy device may be structured to maintain an open pathway from the local environment to the ear canal of the ear on which the device is installed. In some cases, the open pathway, from the local environment to the ear canal of the ear on which the device is installed, passes through the device.

Desirably, the therapy device is structured to maintain the heat contact element at a posterior position with respect to the ear canal of the ear on which the device is installed. For example, an ear opening may be structured to cause radial compression against an exterior surface of the ear, the opening being structured to receive an ear in penetration there-through during installation of the device on the head. An exemplary such ear opening is generally ovaloid to generate a torque against a top and a bottom of an ear to resist twisting of the device about an axis perpendicular to the head. Typically, the ear opening extends around an entire circumference of an installed ear. In certain cases, the ear opening may include an ear cone affixed to the therapy device at a large diameter open end of the cone to dispose a free-standing conic element that extends to a smaller diameter opening disposed at the opposite end of the ear cone. An internal conic surface of the ear cone may be structured to stretch and accommodate in compression against an exterior surface of an installed ear.

Sometimes, the thermal therapy device is passive. Other times, the device may include an electrically active thermal element.

An exemplary heat transfer contact element is embodied in a floor of a contact cavity. Desirably, the floor is transversely flexible and conformable to accommodate and conform under compression against the skin in the vicinity of the ear. A therapy device may also include a bulk cavity disposed in thermal communication with the contact cavity. In certain cases, the bulk cavity is further disposed in fluid communication with the contact cavity. Desirably, the bulk cavity is sized to hold between two-times and about twenty five-times the volume of a heat transfer media that is held in the contact cavity (or even more, possibly much more).

In certain embodiments, a boundary between the contact cavity and the bulk cavity is defined by a step-change in cross-section at the boundary, and heat transfer between the contact cavity and the bulk cavity occurs across a cross-section disposed at the step-change location. Typically, the bulk cavity is insulated to resist heat transfer into the bulk cavity from the local environment. The bulk cavity may also be insulated to resist heat transfer into the bulk cavity from the head and/or structured to avoid contact with the head, and/or to resist heat transfer into the bulk cavity from the ear.

An embodiment according to certain principles of the instant invention may be configured to provide thermal therapy to the head of a human. An exemplary embodiment includes a first cooling pack having a first heat transfer element with a first contact surface and a first pack aperture to a first tunnel, the first tunnel communicating from the first contact surface through a first thickness of the first pack. An embodiment may include a second cooling pack. Typically, the second cooling pack is basically symmetric to the first cooling pack. That is, the second cooling pack may also have a second heat transfer element with a second contact surface and a second pack aperture to a second tunnel, the second tunnel communicating from the second contact surface through a first thickness of the second pack.

Typically, one or more cooling packs are held in operable registration on the head by way of a band, or belt. One workable band has a band thickness between a band inside surface and a band outside surface. Desirably, a band is adjustable in length along a band circumference to accommodate human heads of various sizes in reception within the band circumference. Preferred bands are configured such that the first and/or second cooling pack can be carried by the band for application of thermal therapy to the head of a human wearer of the band.

In certain embodiments, at least one cooling pack has a tunnel disposed to communicate from a respective contact surface to at least an inside surface of the band. A workable tunnel is configured to receive a helix portion of a human ear therein. A tunnel may communicate from a first contact surface to at least an outside surface of the band.

A workable cooling pack may include a first bladder and a second bladder, each such first and second bladder being spaced apart by a foldable element to permit juxtaposition of a thermally conductive face of the first bladder and a thermally conductive face of the second bladder. The juxtaposed faces may then form a path for heat transfer between first and second bladders.

Desirably, one or more cooling pack may be removably affixable to the band at a plurality of operable locations disposed around the band circumference to dispose an ear-receiving tunnel in agreement with a respective ear of a human user. In that configuration, each respective tunnel may receive protruding portions of a human ear to permit the contact surface of the cooling pack to be disposed in contact with the user's head in the vicinity of the user's respective ear canal.

An embodiment may include a holding mechanism configured to permit adjusting a held position of a cooling pack with respect to the band to operably align a first aperture in the band and a second aperture in the cooling pack, the aligned first aperture and second aperture to receive the helix portion in penetration there-through. A currently preferred holding mechanism is a hook-and-loop connection between the pack and the band. An alternative the holding mechanism includes a belt loop connection between the pack and the band. A belt loop connection may include a belt loop aperture spaced apart from a cooling pack edge to define a belt loop tab, the band being installed in penetration through the belt loop aperture.

In the case where a first cooling pack includes a first bladder and a second bladder, the first and second bladder being spaced apart by a foldable element to permit juxtaposition of a thermally conductive face of the first bladder and a thermally conductive face of the second bladder, the belt loop tab may be disposed on the opposite side of the band from the first contact surface. Sometimes, such a cooling pack may be suspended from the belt such that the belt loop tab is disposed on the opposite side of the band from both of the first bladder and the second bladder of the folding cooling pack.

Sometimes, the first and second cooling pack of a workable embodiment each include a second thickness disposed on the opposite side of a suspension/application band from the respective first thickness, and the first and second tunnels further extend through the second thickness of each respective cooling pack. That is, a combined tunnel may pass completely through the thickness of a folded cooling pack. The tunnel may also include a portion passing through the suspension band. In that case, the wearer's ear canal is unobstructed.

In another workable configuration, the first cooling pack and second cooling pack are permanently affixed to the band at respective operable locations of the band circumference, and the band is structured to dispose the first and second tunnels in agreement with respective left and right ears of a user such that each respective tunnel may receive protruding portions of a human ear to permit the first and second contact surfaces to be disposed in contact with the user's head in the vicinity of the user's respective left and right ear canals.

Desirably, a suspension band is adjustable in circumferential length. Certain bands may simply stretch in circumferential length to fit a particular wearer. In one embodiment, a band may include a multi-part adjustment mechanism operable to change a circumferential length of the band. The currently preferred multi-part adjustment mechanism includes a hook-and-loop fastener assembly.

In certain embodiments, a band may be configured such that operation of a multi-part adjustment mechanism to effect a change in in length of the band circumference primarily causes a corresponding change in a circumferential distance between posterior ends of respective first and second cooling packs. For example, a cooling pack may be affixed at the pack anterior end, permitting the posterior end to slide with respect to the band when the multi-part mechanism reduces circumferential length of mounting wings, and a distance between posterior portions of a pair of installed cooling packs is increased. On the other hand, the band may be configured such that operation of the multi-part adjustment mechanism to effect a change in the band circumference primarily causes a corresponding change in a circumferential distance between anterior ends of respective first and second cooling packs. E.g., pack rear parts are stitched to less-stretchy wing panel, and the anterior band portion between packs consequently stretches in length. Said in another way, the band may include portions of varying extensibility to permit modification of a circumferential length disposed between anterior ends and/or posterior ends of the first and second cooling packs.

In certain cases, a band includes at least one oversize through-hole to permit displacement of, and cooperating alignment of, a suspended cooling pack's tunnel with an ear canal of the wearer. Desirably, the position of the cooling pack with respect to the band may be adjusted while still maintaining operable registration between the tunnel and through-hole.

A cooling pack may be configured as a multi-layer cooling pack to be carried in some way by a suspension band. Preferred embodiments of a multi-layer cooling pack are structured in cooperation with the band to trap one layer of the multi-layer cooling pack between a wearer's head and the band. Further, such preferred embodiments may be structured in cooperation with the band to trap both layers of a 2-layer cooling pack between a wearer's head and the band.

BRIEF DESCRIPTION OF THE DRAWINGS

In the drawings, which illustrate what are currently considered to be the best modes for carrying out the invention:

FIG. 48 is a plan view of the inside surface of the embodiment in FIG. 44;

FIG. 49 is a side view in elevation of the embodiment in FIG. 48;

FIG. 52 is a plan view of the inside surface of a belt for use with certain embodiments;

FIG. 53 is a plan view of the outside surface of the belt in FIG. 52;

Figure 55:
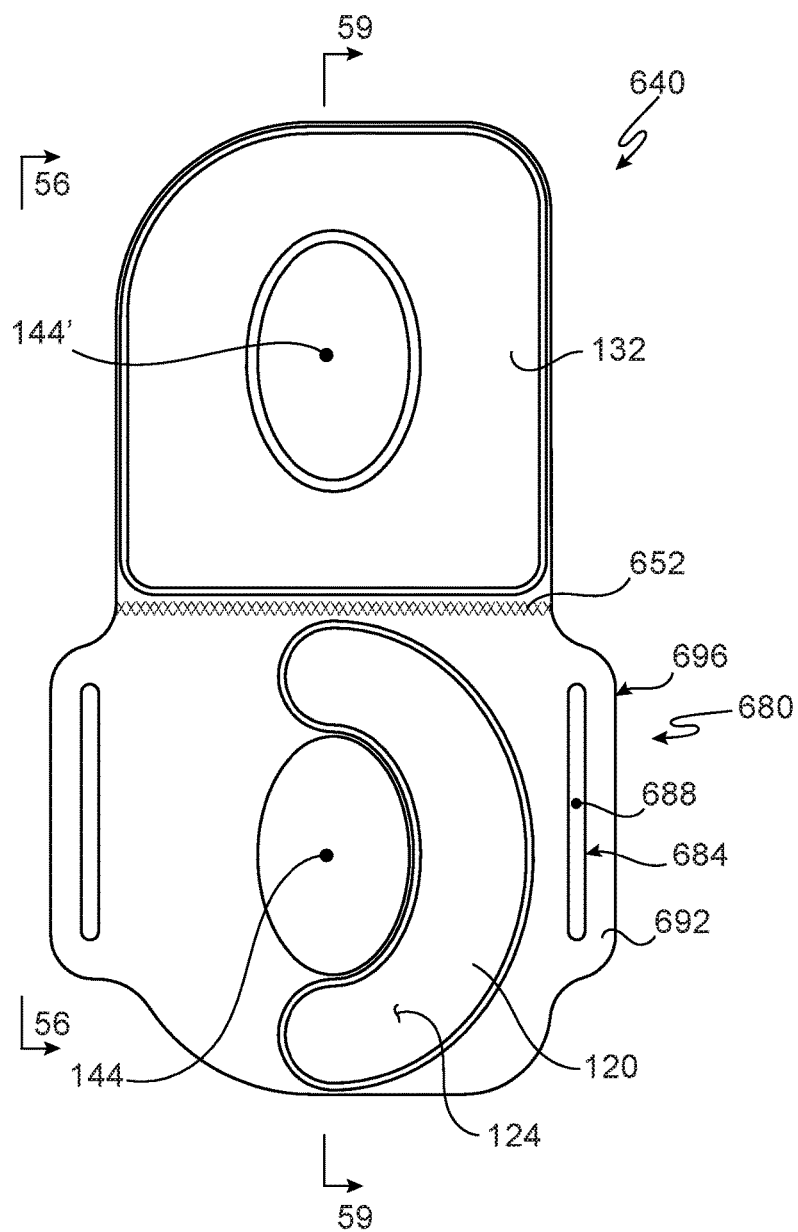
FIG. 55 is a plan view of an embodiment of a folding cooling pack, in an unfolded configuration.
Figure 56:
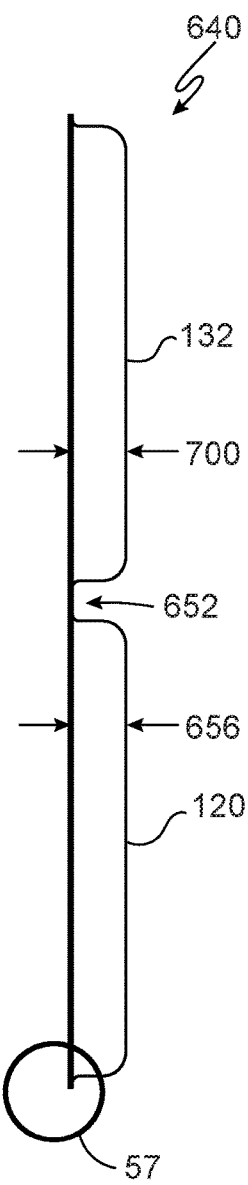
FIG. 56 is a side view of the embodiment in FIG. 55, taken from section 56-56 in FIG. 55 and looking in the direction of the arrows.
Figure 59:
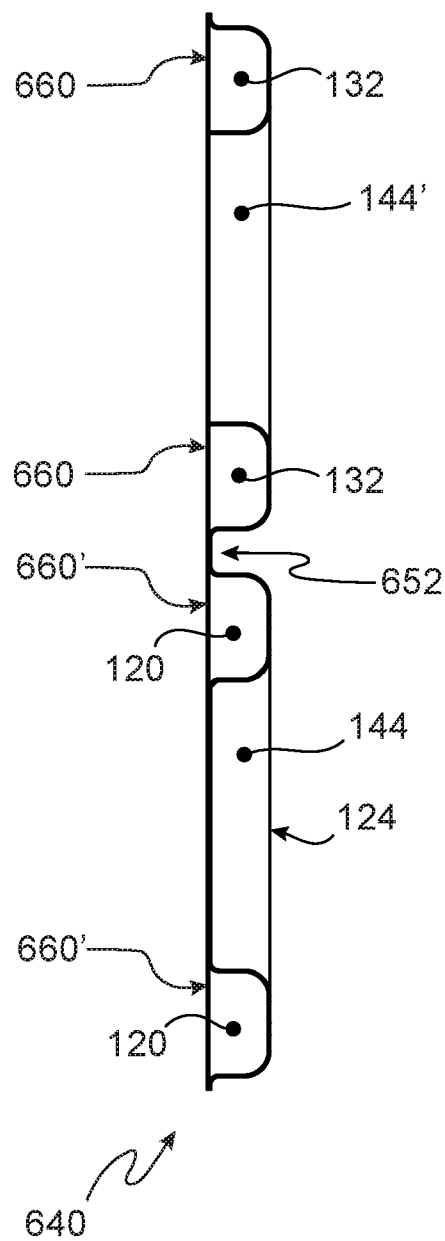
Figure 60:
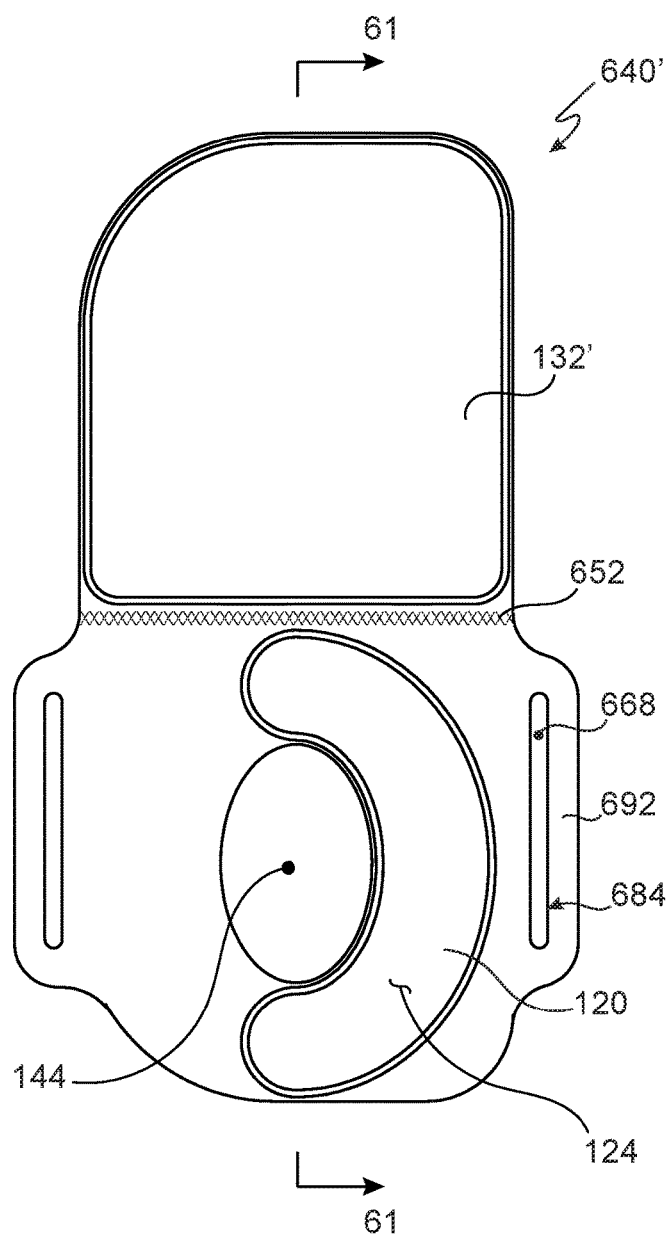
Figure 61:
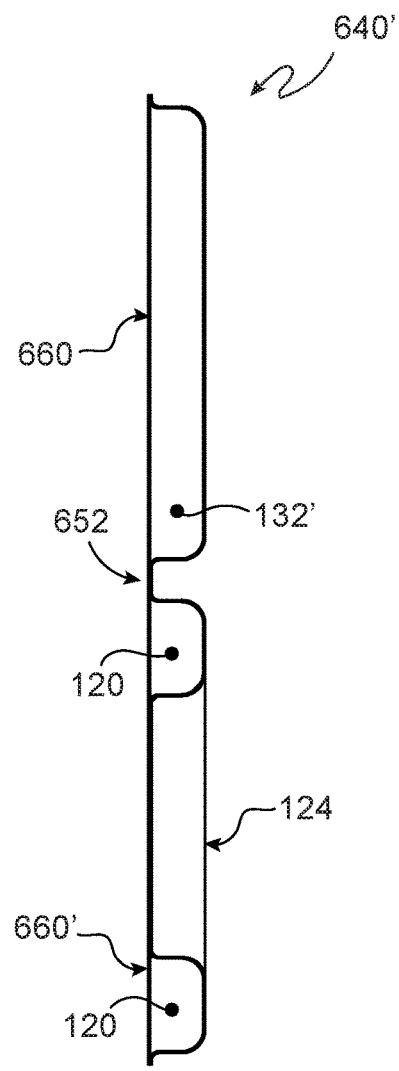
Figure 62:
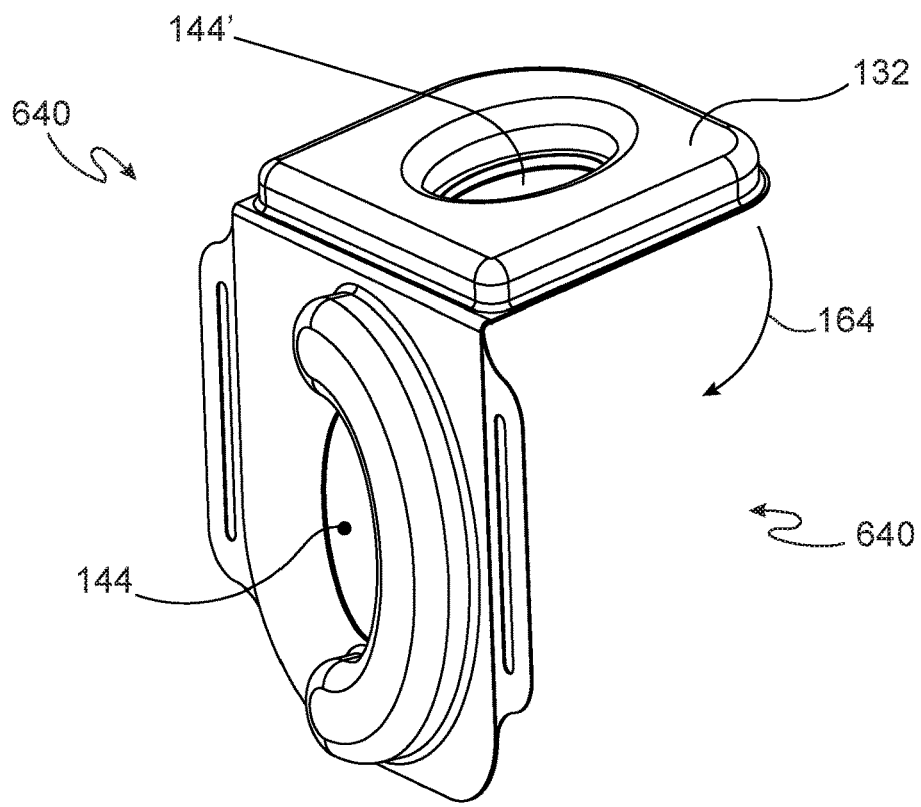
Figure 63:
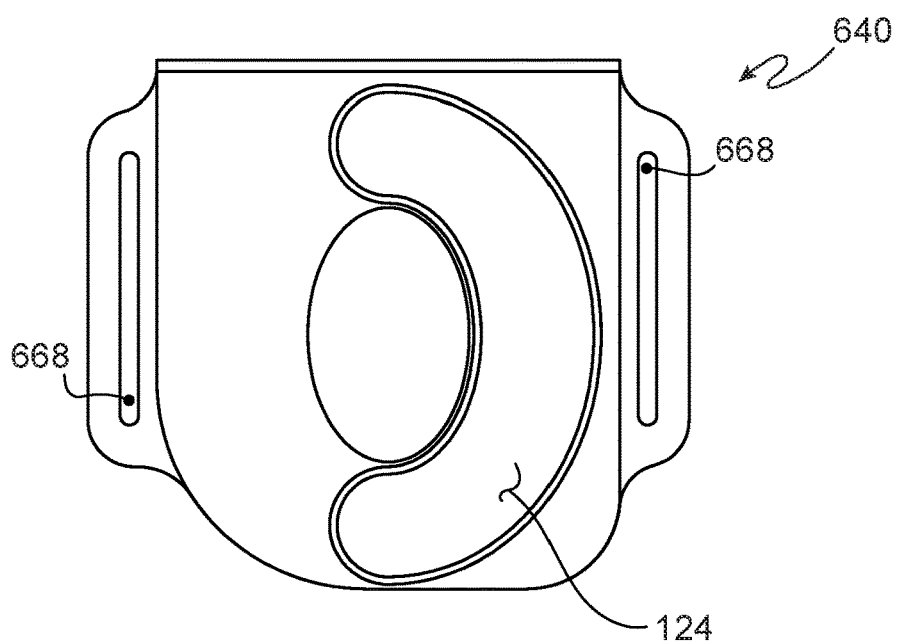
Figure 64:
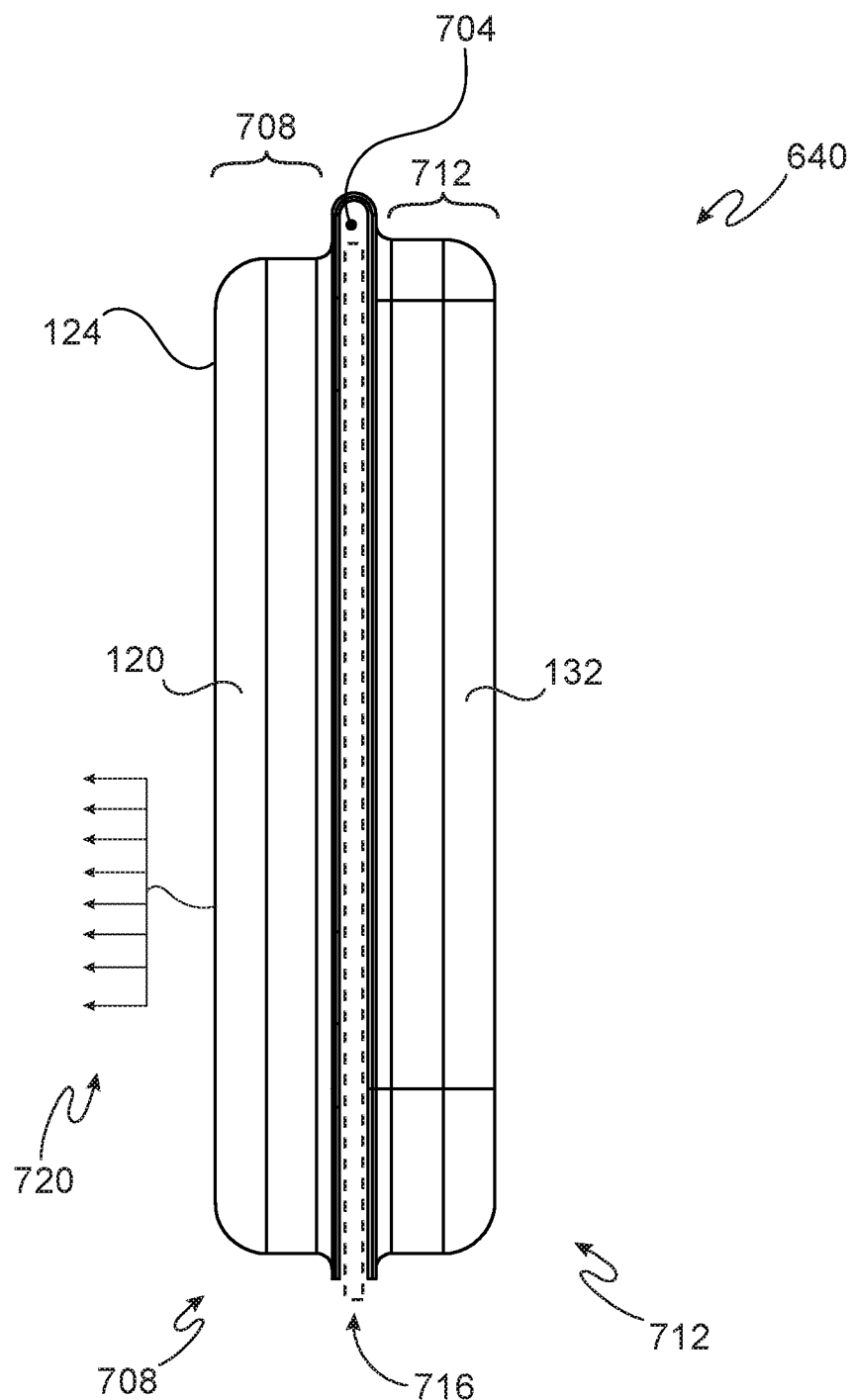
Figure 65:
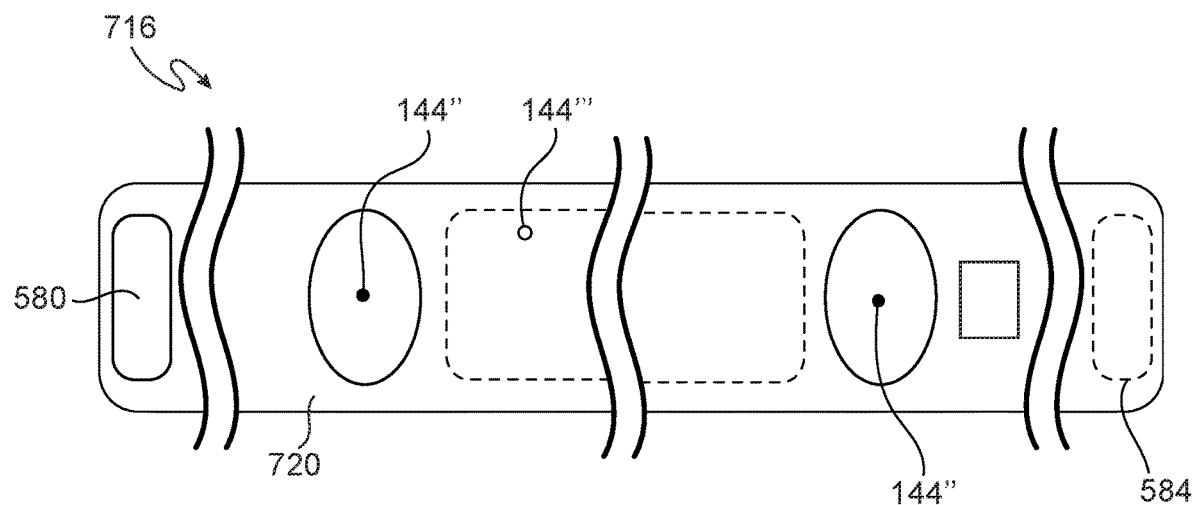
Figure 66:
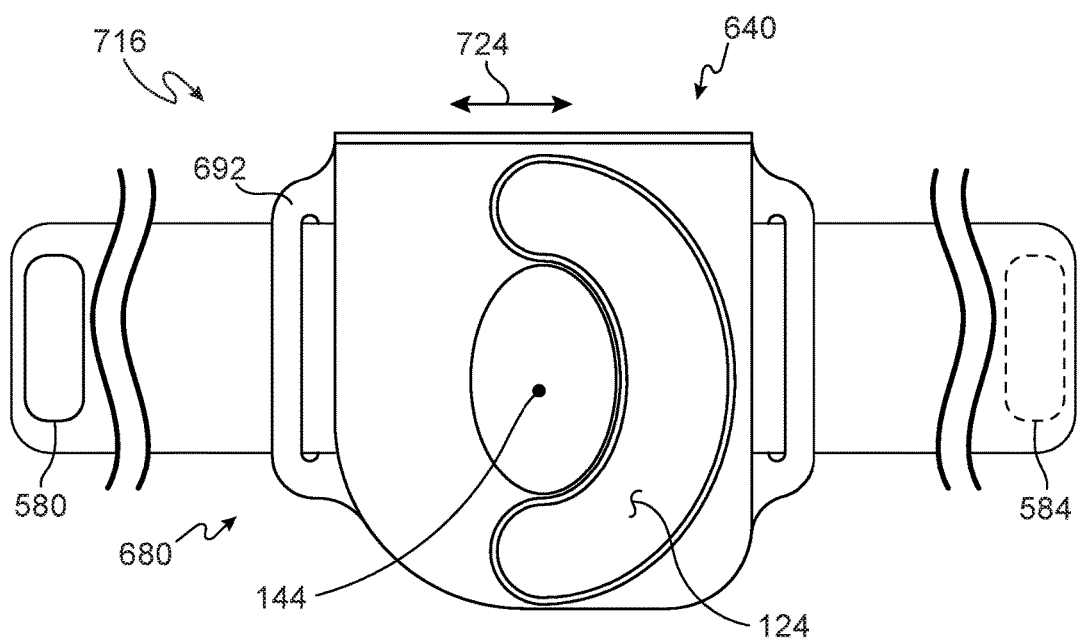
Figure 67:
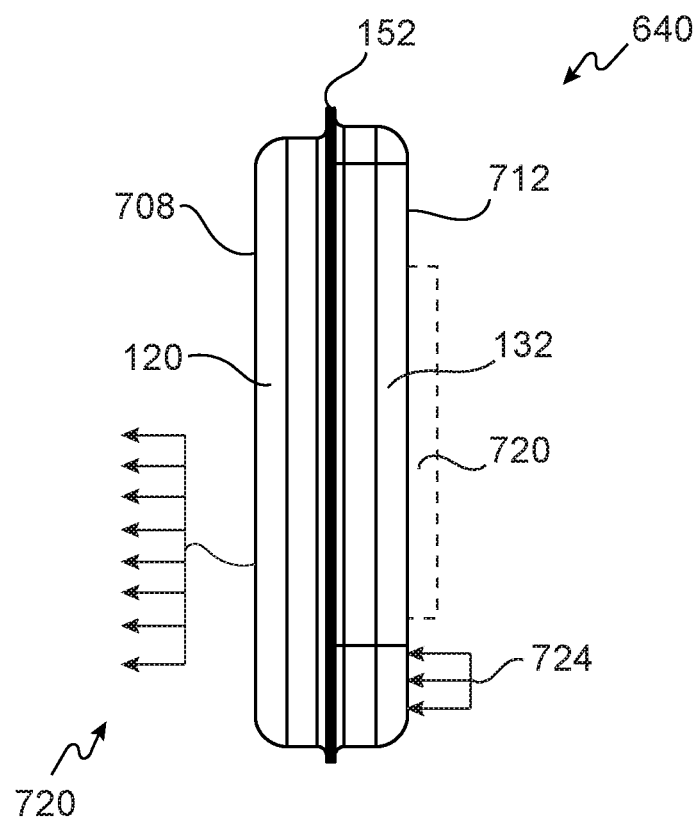
Figure 68:
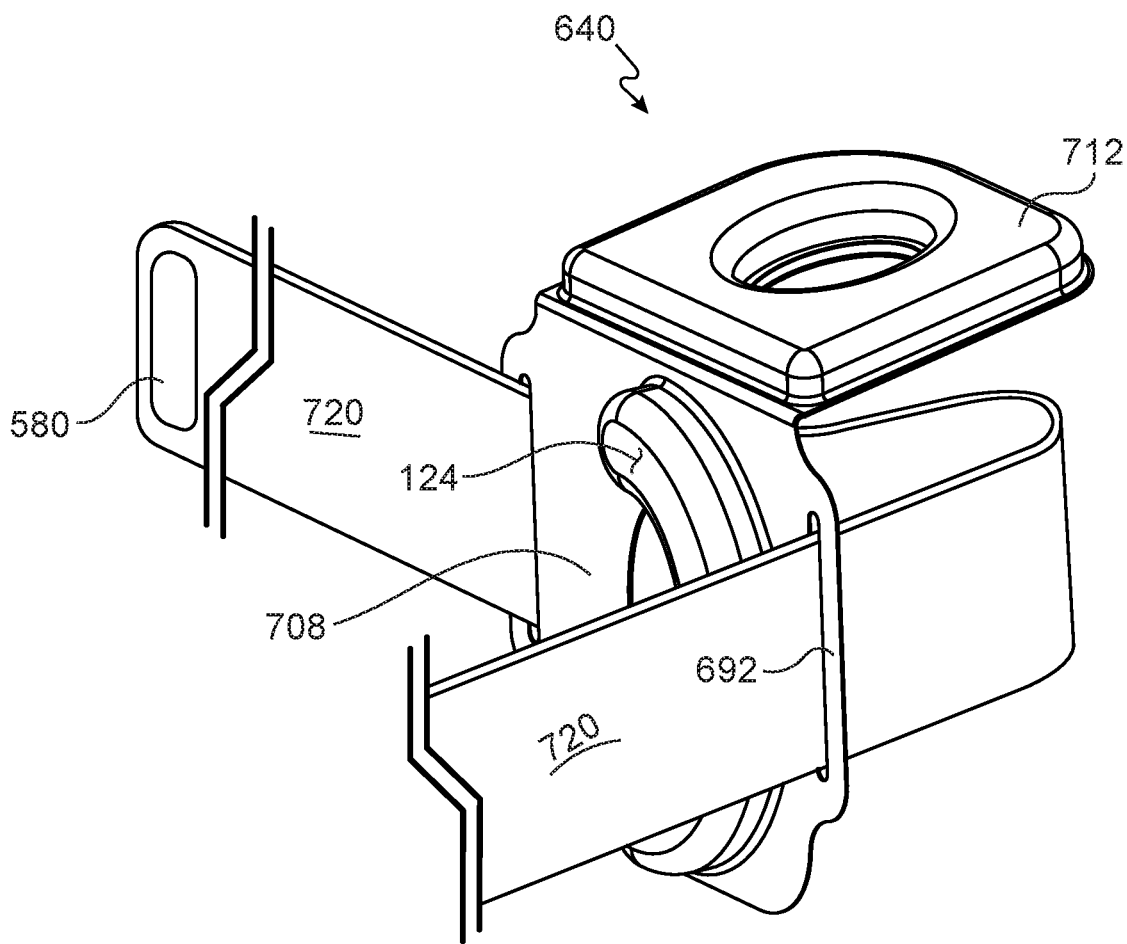
Figure 69:
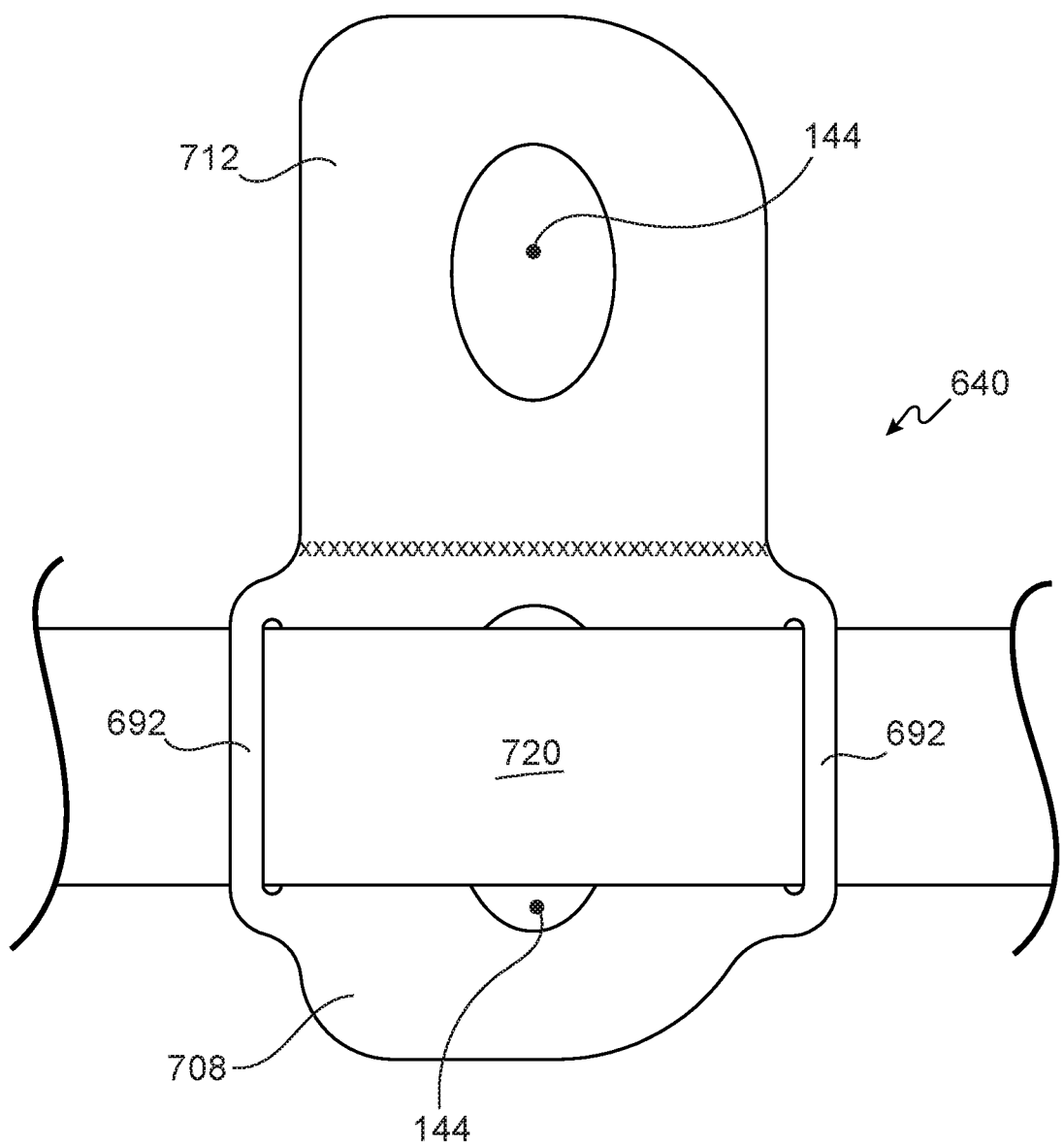
Figure 70:
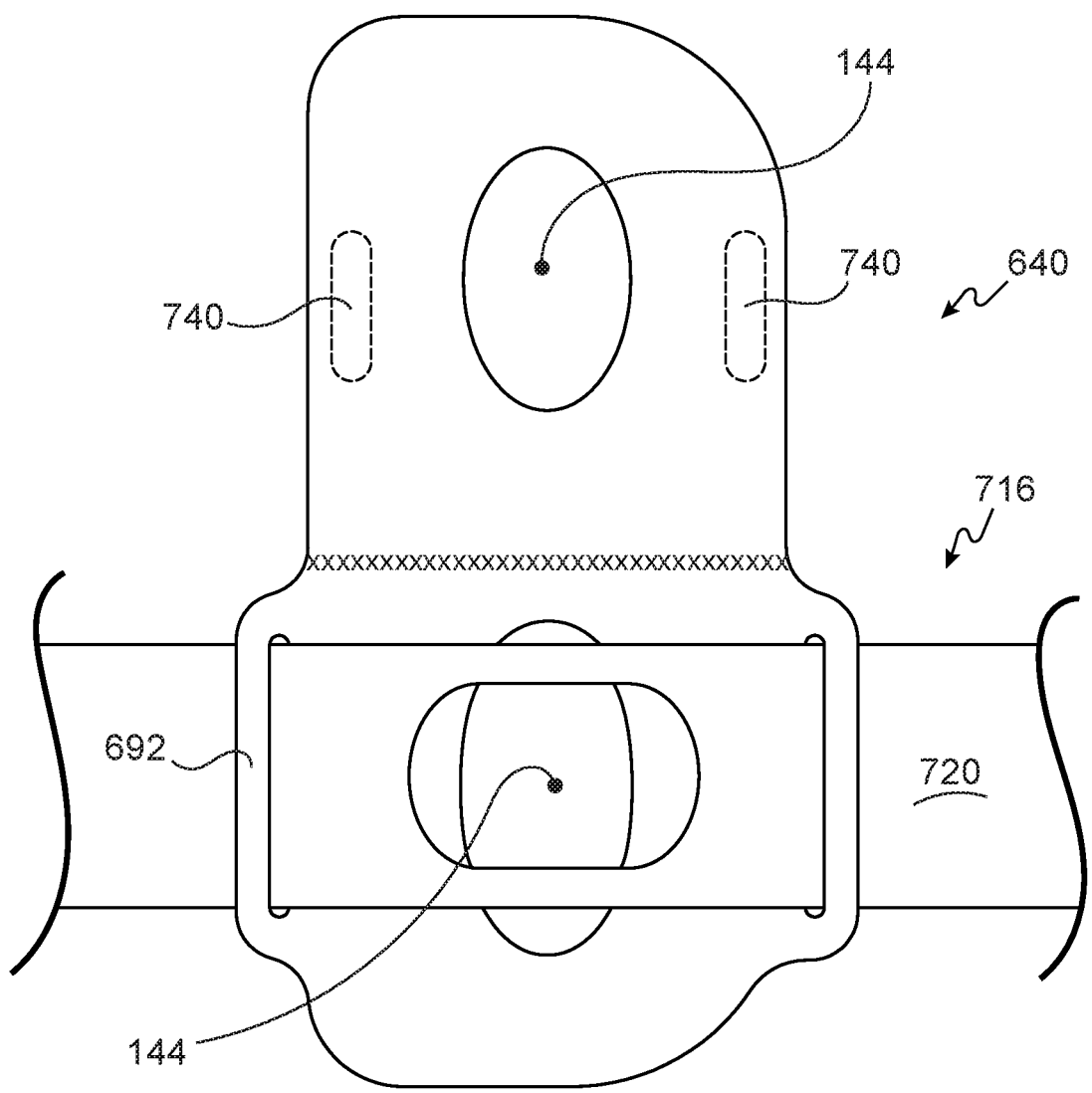
Figure 71:
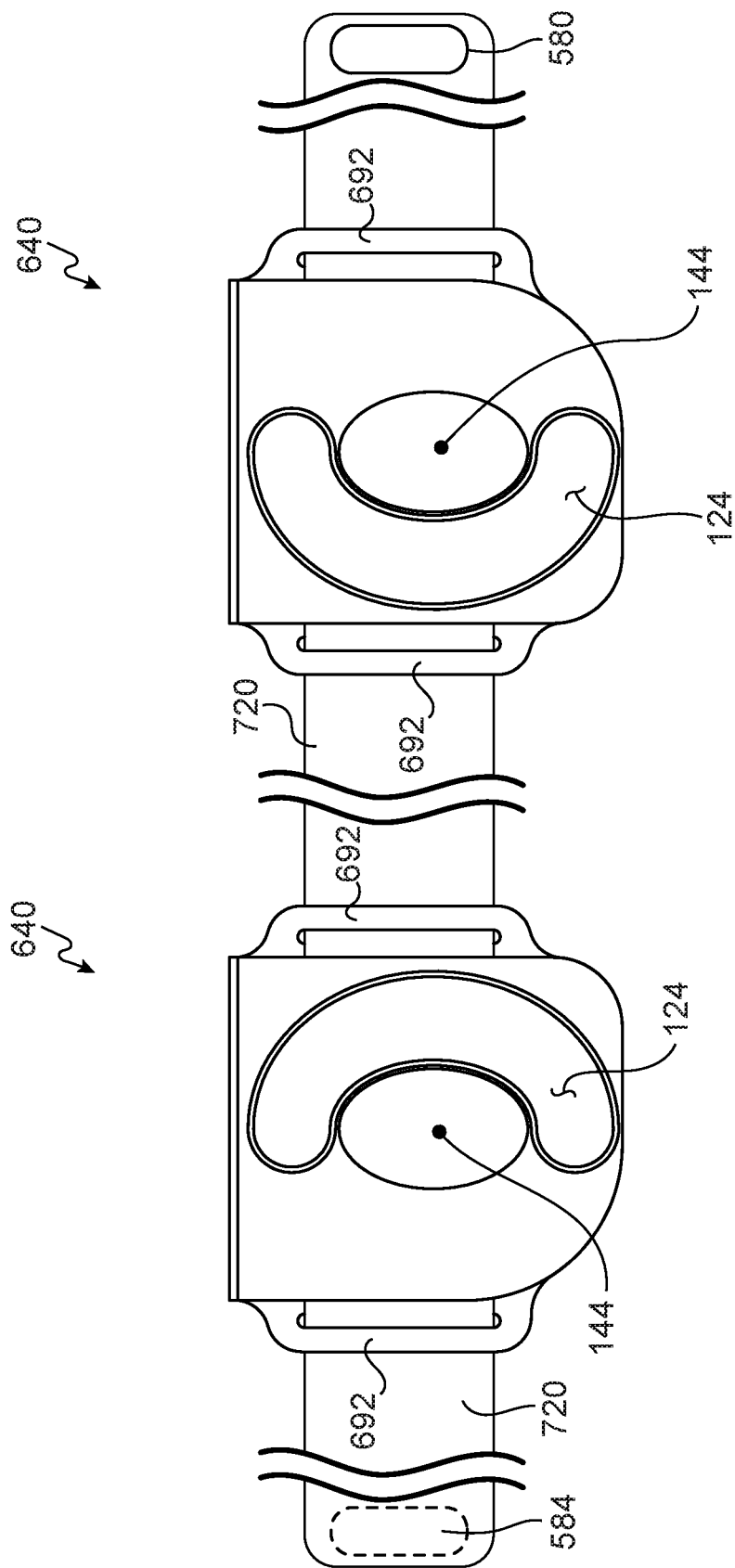
Figure 72:
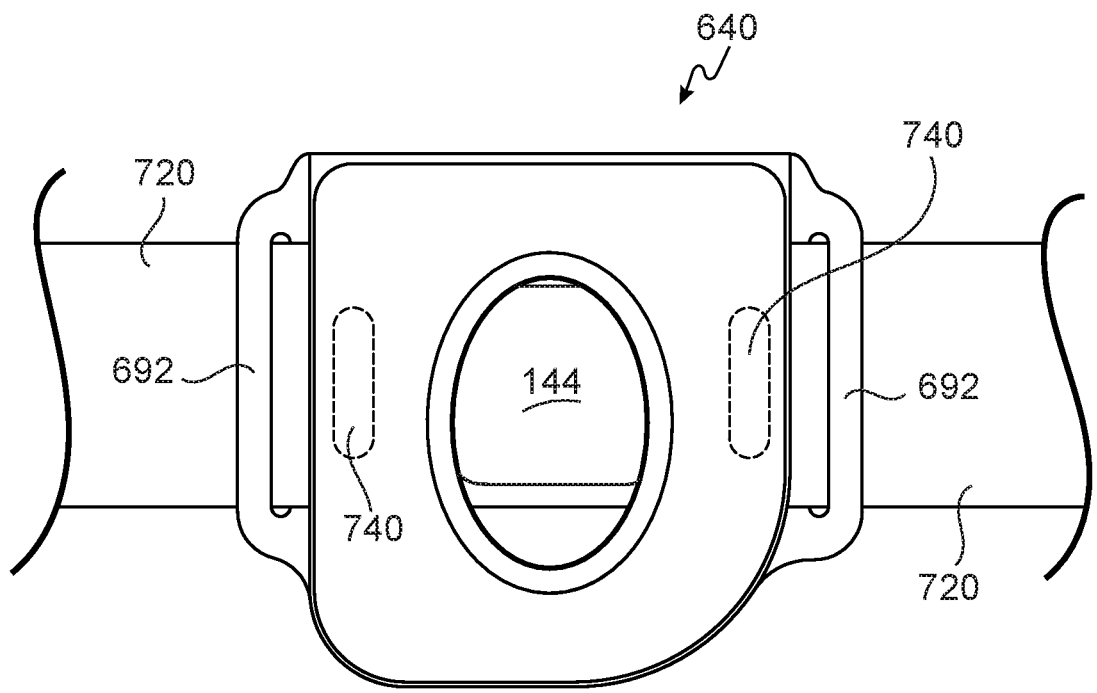
Figure 73:
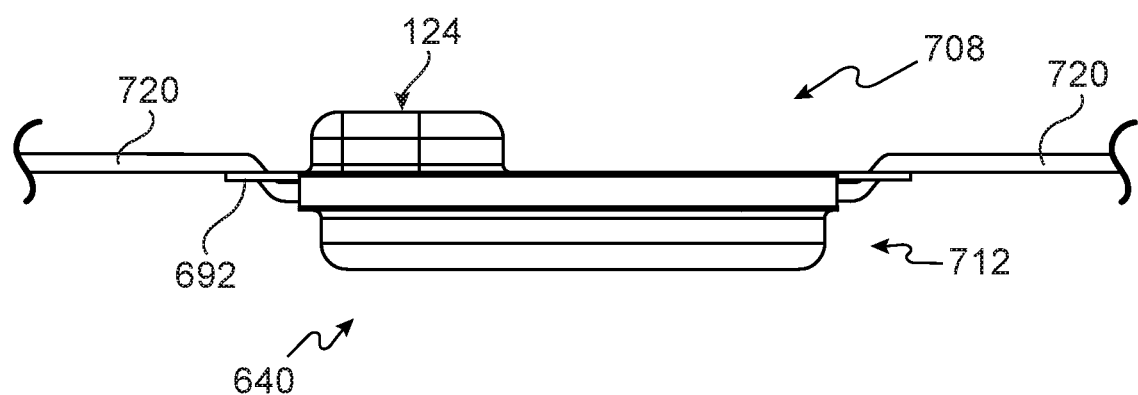
Figure 74:
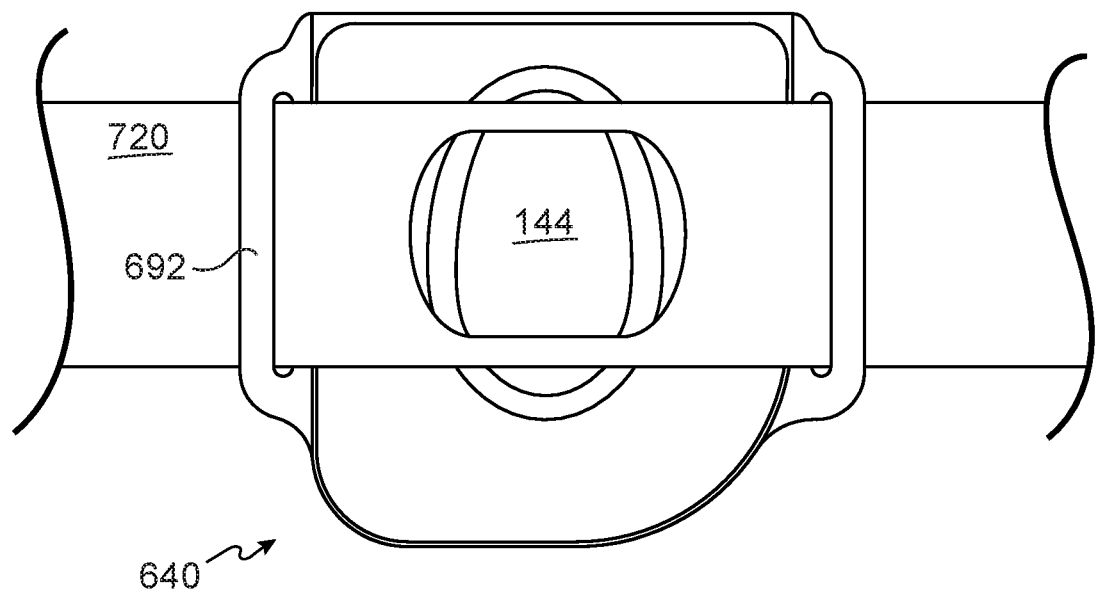
Figure 75:
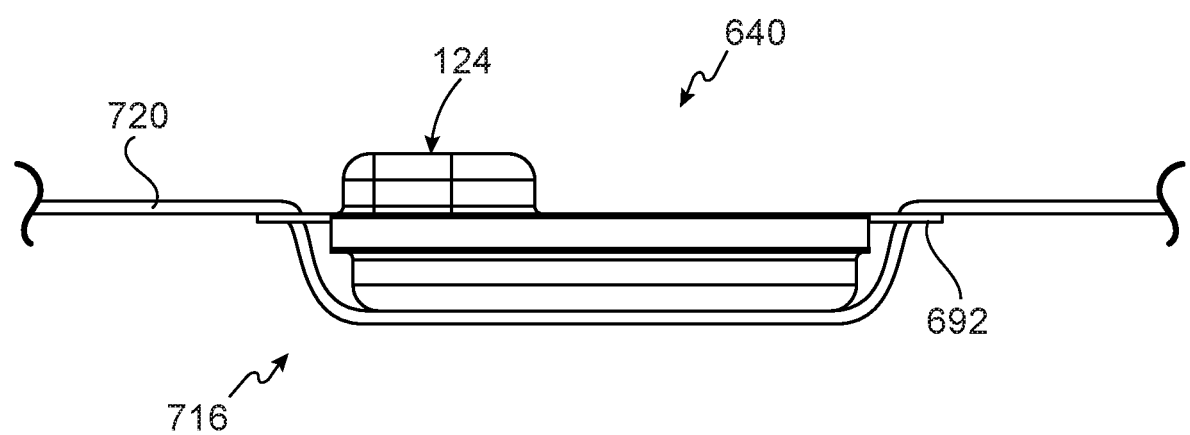
Figure 76:
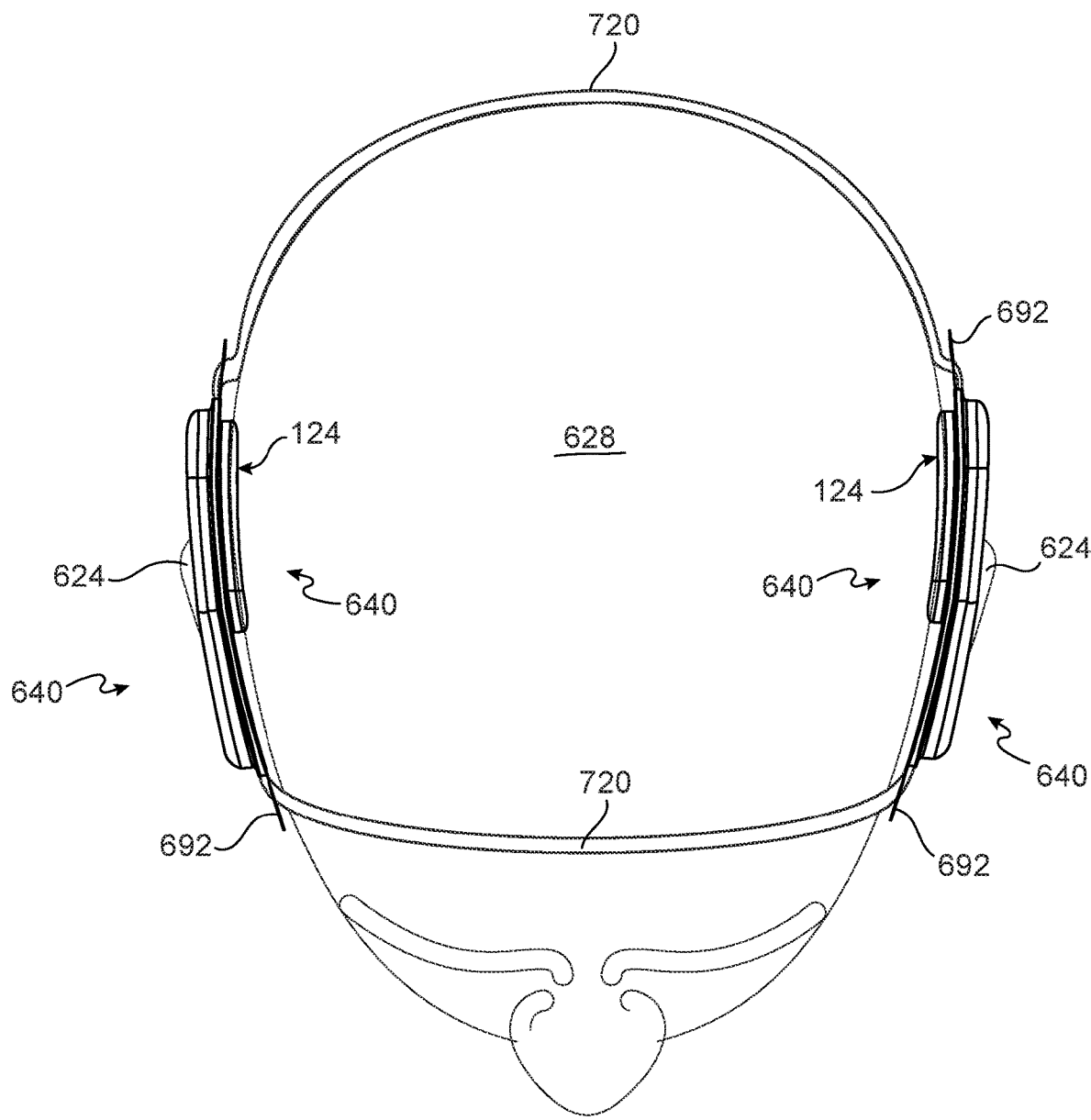
Figure 77:
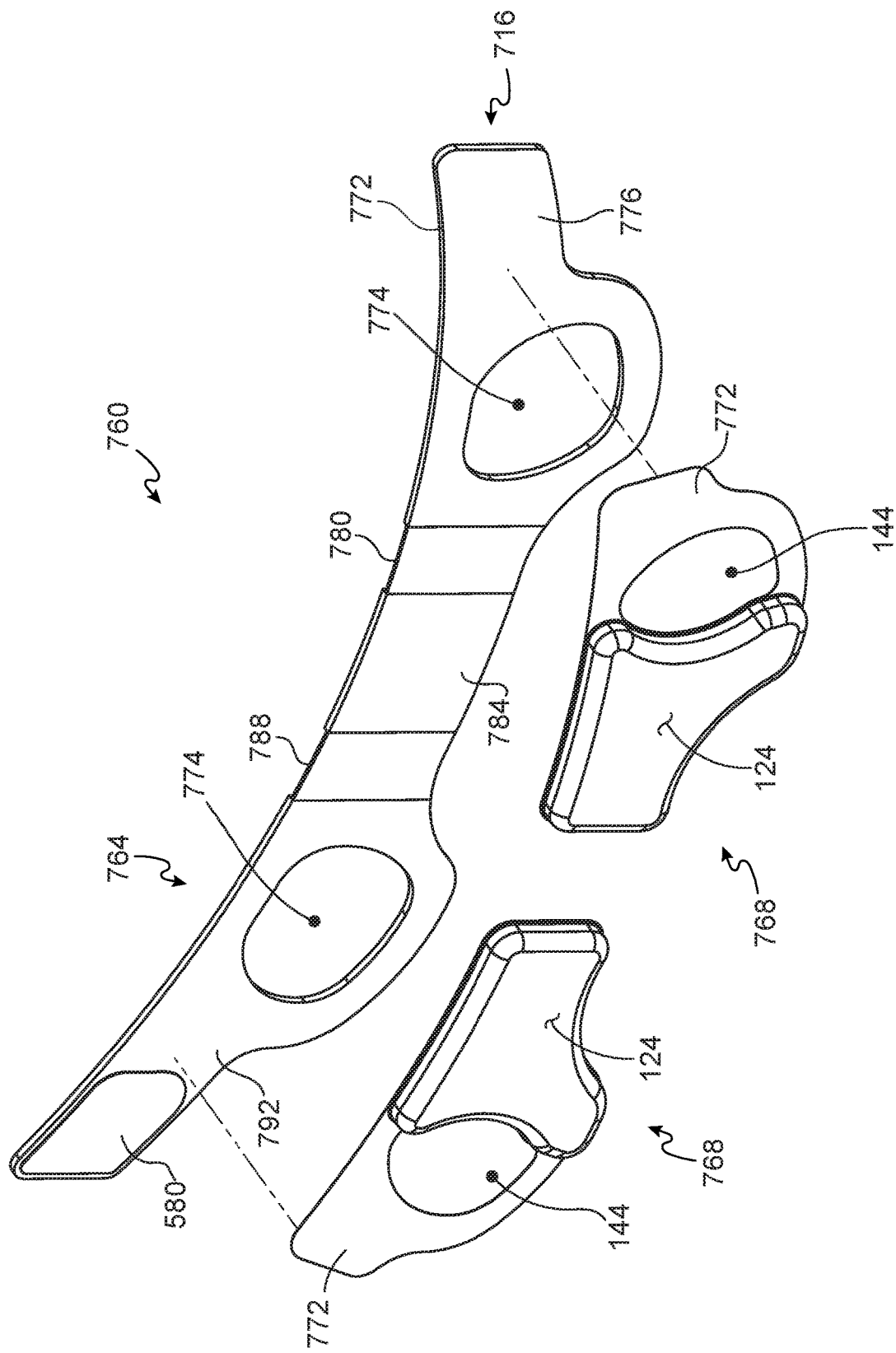

58 is a plan view of the opposite side of the embodiment in FIG. 55;

FIG. 59 is a cross-section view taken through the section 59-59 in FIG. 55, and looking in the direction of the arrows;

FIG. 60 is a view similar to that in FIG. 55, of an alternative embodiment of a folding cooling pack;

FIG. 61 is a cross-section view taken through the section 61-61 in FIG. 60, and looking in the direction of the arrows;

FIG. 62 is a view in perspective of the folding cooling pack embodiment in FIG. 55, partially folded;

FIG. 63 is a side view of the folding cooling pack embodiment in FIG. 55, fully folded;

FIG. 64 is an end view of the folding cooling pack embodiment in FIG. 55, fully folded;

FIG. 65 is a side view of a belt operable with embodiments, including the folding cooling pack embodiment in FIG. 55;

FIG. 66 illustrates a cooling pack installed on a belt similar to the belt in FIG. 65;

FIG. 67 illustrates a cooling pack installed on a belt similar to the belt in FIG. 65;

FIG. 68 is a perspective view illustrating an association of a cooling pack and a band;

FIG. 69 is a side view of a partially assembled first embodiment;

FIG. 70 is a side view of a partially assembled second embodiment;

FIG. 71 is a side view of an embodiment including a pair of cooling packs;

FIG. 72 is a side view illustrating a first configuration to effect the association of a cooling pack and a band;

FIG. 73 is a top view of the configuration in FIG. 72;

FIG. 74 is a side view illustrating a second configuration to effect the association of a cooling pack and a band;

FIG. 75 is a top view of the configuration in FIG. 74;

FIG. 76 is a view from above of an embodiment installed on the head of a human;

FIG. 77 is a perspective assembly view of an alternative embodiment;

FIG. 78 is a rear (outside) view in elevation of the embodiment in FIG. 77; and

FIG. 79 is a front (inside) view in elevation of the embodiment in FIG. 77.

DETAILED DESCRIPTION OF THE ILLUSTRATED EMBODIMENTS

Reference will now be made to the drawings in which the various elements of the illustrated embodiments will be given numerical designations and in which the invention will be discussed so as to enable one skilled in the art to make and use the invention. It is to be understood that the following description is only exemplary of certain principles of the present invention, and should not be viewed as narrowing the claims which follow.

Figure 5:
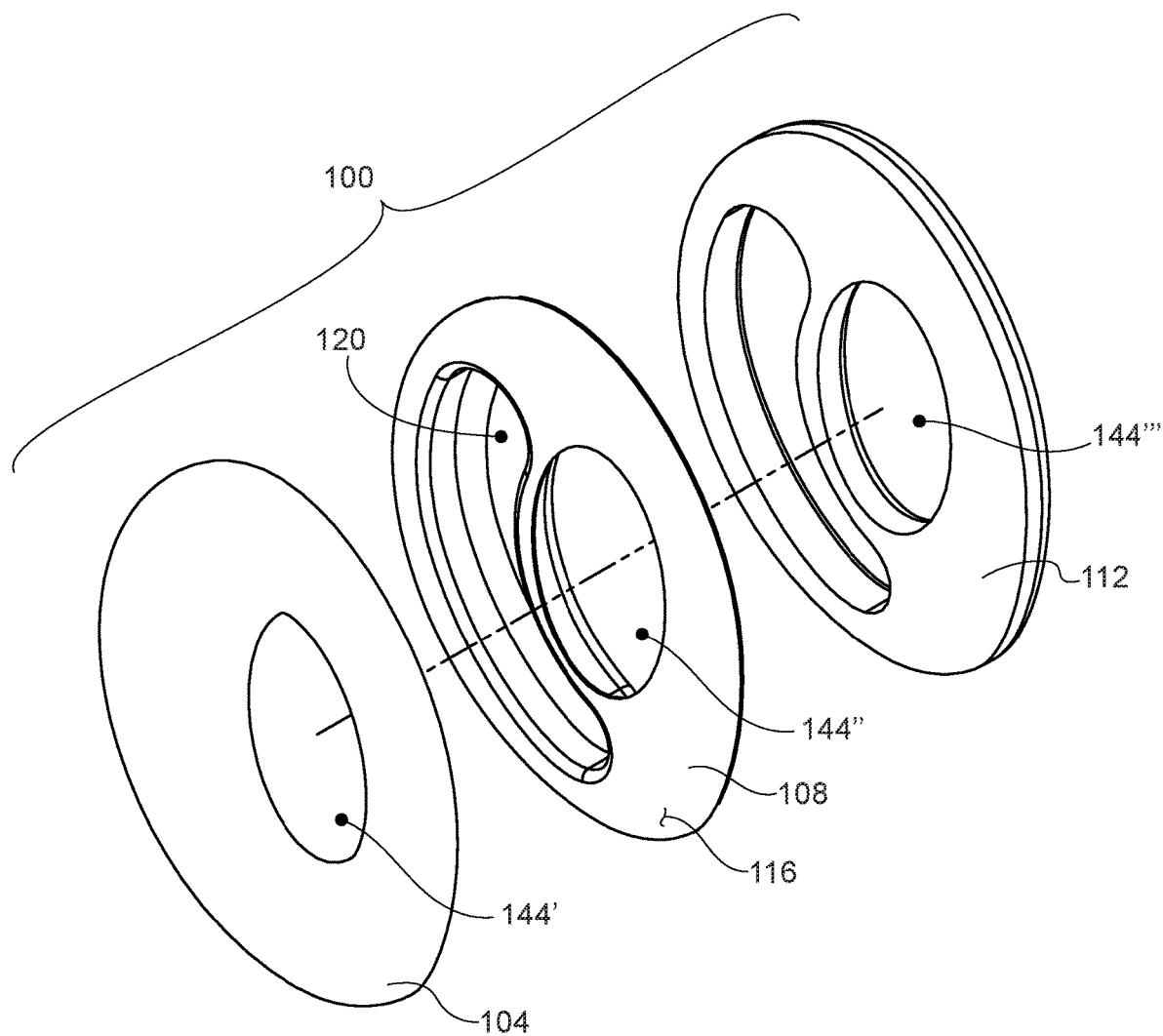
FIG. 5 is an exploded assembly view in perspective looking at the back side of the embodiment in FIG. 1.

An exemplary thermal device, or cooling pack assembly, is indicated generally at 100 in FIGS. 1 through 6. With particular reference to FIG. 5, embodiment 100 includes a rear cover 104, a membrane 108, and an insulator 112. Membrane 108 includes a substantially flat surface 116 that is formed to include or define a cavity 120. Cover 104 forms a rear surface of device 100.

Cavity 120 forms a contact heat transfer reservoir, and typically projects through insulator 112 to dispose its front or contact surface 124 proud of the exposed front surface 128 of insulator 112 (see FIG. 6), such that surface 124 will contact the patient's skin near the ear. Desirably, cavity 120 provides a contact surface 124 that is structured to conform to the different anatomical surfaces of a variety of different patients. Also, it is desirable for membrane 108 to facilitate heat transfer from a patient into thermal/heat transfer fluid or media confined inside cavity 120.

Figure 6:
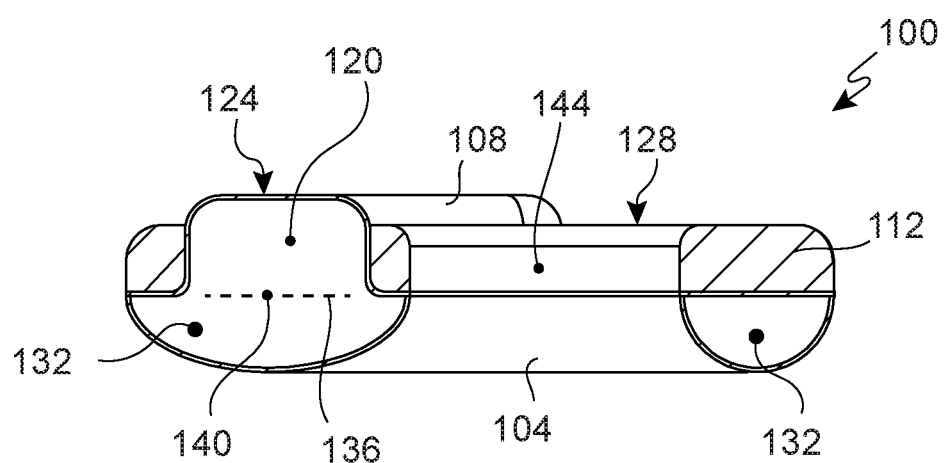
FIG. 6 is the cross-section view indicated in FIG. 2 by section lines 6-6 and looking in the direction of the arrows.

As illustrated in FIG. 6, cover 104 forms a cavity 132 in which to hold a bulk quantity of heat transfer fluid or media. Desirably, cover 104 includes an insulating property to resist heat transfer from a patient's ear (e.g., from a medial portion of the projecting cantilevered ear "flap"), or the local environment, into cavity 132. Consequently, a cover 104 may include a plurality of layers of different materials (not illustrated). Cavity 120 and cavity 132 may be regarded as separated by an imaginary boundary 136 for purpose of structure definition. In fact, and in the case of illustrated embodiment 100, they may be in fluid communication and together form a combined reservoir cavity 140, in which is confined heat transfer media or fluid. It is preferred for a cavity 132 to be sized to hold a volume of heat transfer media that is about 2 times as great as a volume held in cavity 120. A workable cavity 132 may hold between 2 times and up to perhaps 25 times the volume that is held in a cavity 120, or even more.

A through-hole or tunnel 144 is formed in device 100 to accommodate passage there-through of a human ear.

Figure 1:
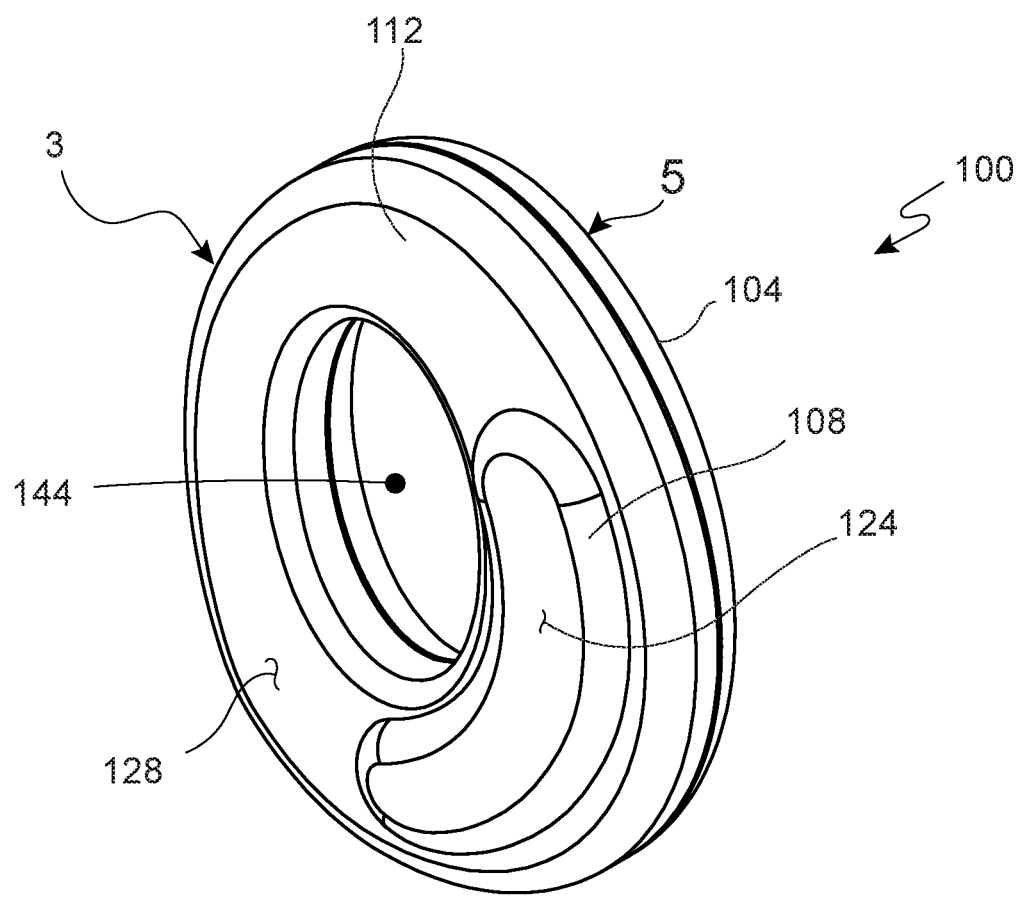
FIG. 1 is a perspective view looking at the front side, or alternatively the head-side, or contact portion, of a localized cooling pack assembly structured according to certain principles of the invention.
Figure 2:
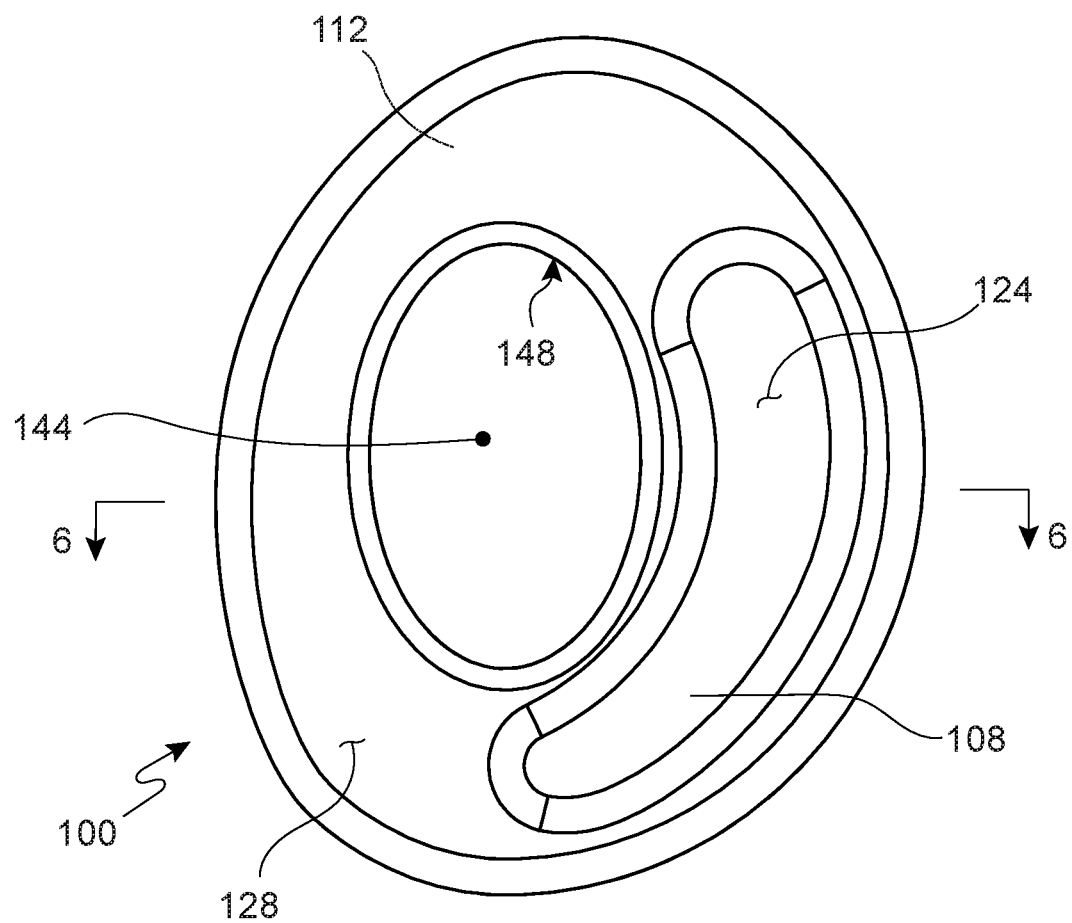
FIG. 2 is a front plan view of the device in FIG. 1
Figure 3:
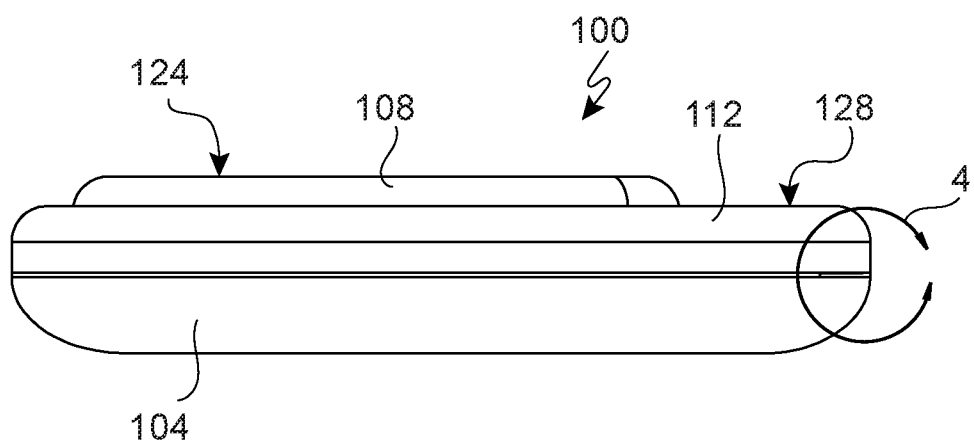
FIG. 3 is a side view in elevation of the device in FIG. 1.
Figure 4:
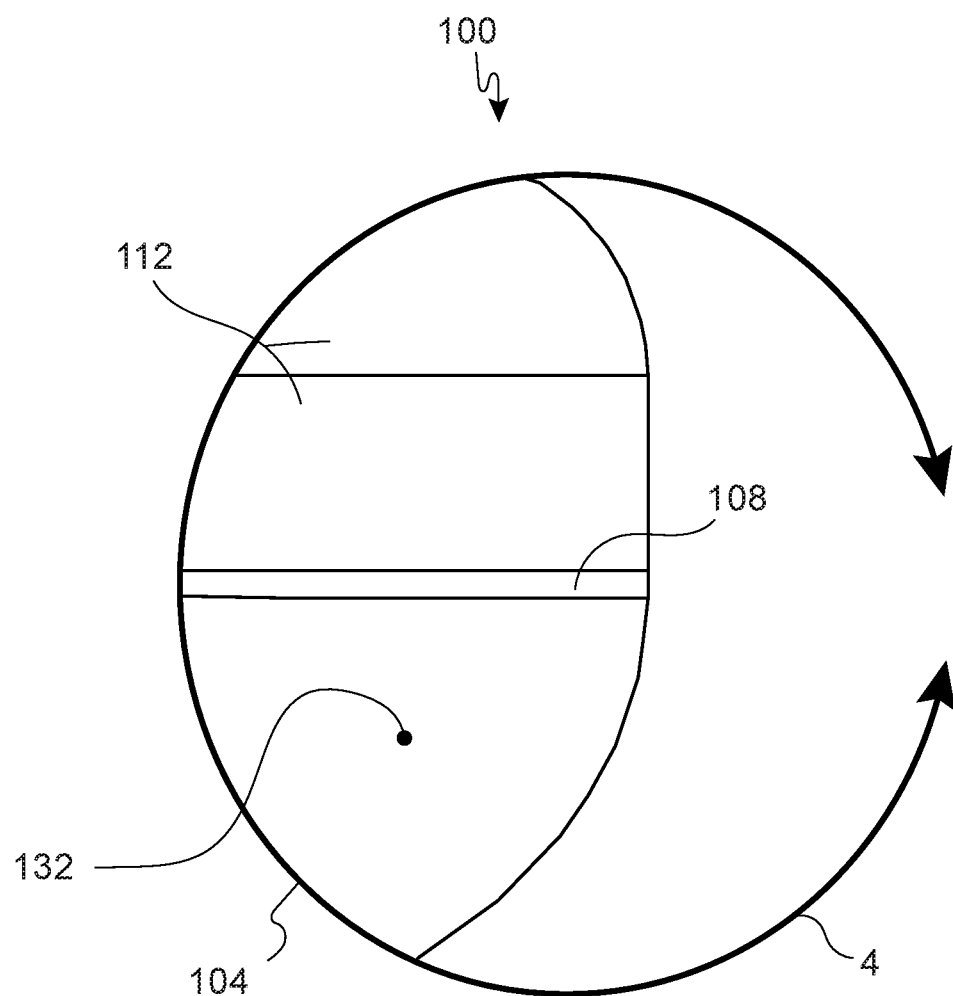
FIG. 4 is a close-up view of the detail indicated by circle 4 in FIG. 3.

Through-hole 144 is formed by corresponding through-holes 144', 144", and 144''' in cover 104, membrane 108, and insulator 112, respectively (see FIG. 5). As shown in FIG. 2, the perimeter 148 of through-hole 144 may be structured as a generally ovaloid cross-section, to fit in registration with the conventional shape of a human ear when the device 100 is installed on an ear. The non-circular cross-section of through-hole 144 resists twisting of the device out of desired registration to apply cooling to a particular location of the head.

Embodiment 100 is a passive cooling pack, and includes a cavity 140 that contains heat transfer media or fluid (liquid, gel, etc.). The entire device 100, or a component such as cavity 120, is typically chilled in a freezer, then applied as desired to a patient's head in the vicinity of an ear. Heat is removed from a localized portion of the patient's head, and absorbed by contact heat transfer reservoir 120. Heat gained in reservoir 120 is then transferred into bulk reservoir 132.

Figure 7:
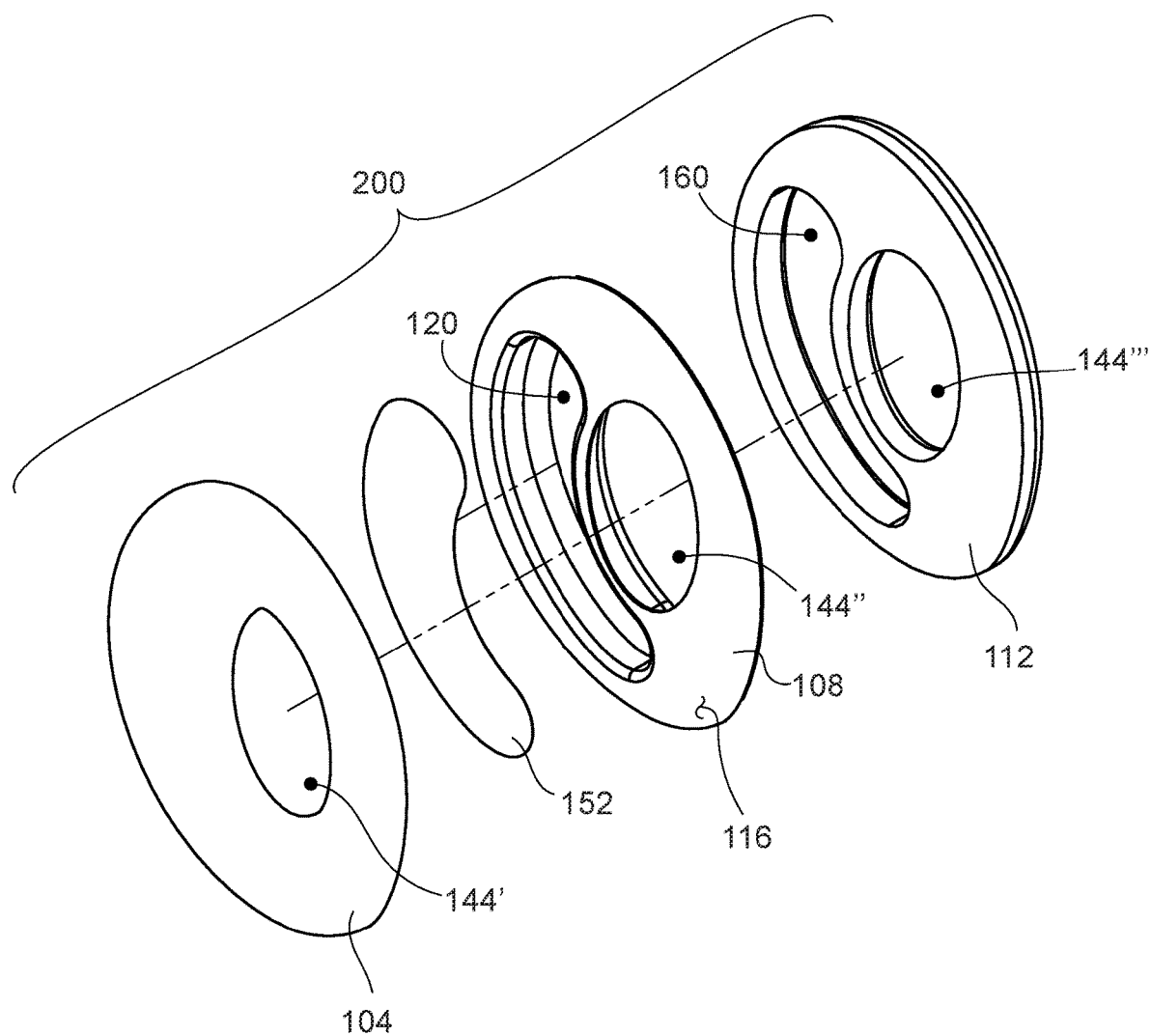
FIG. 7 is an exploded assembly view, similar to that in FIG. 5, of an alternative embodiment.
Figure 8:
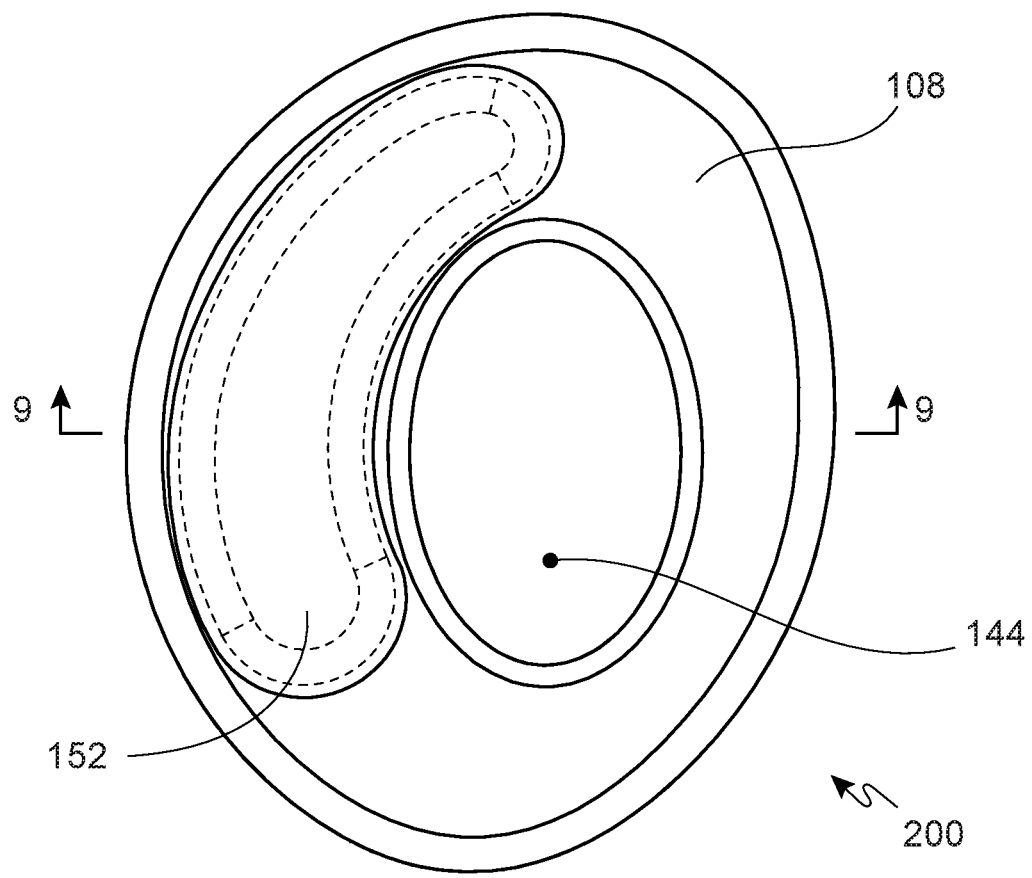
FIG. 8 is a rear plan view of the device in FIG. 7, partially assembled.
Figure 9:
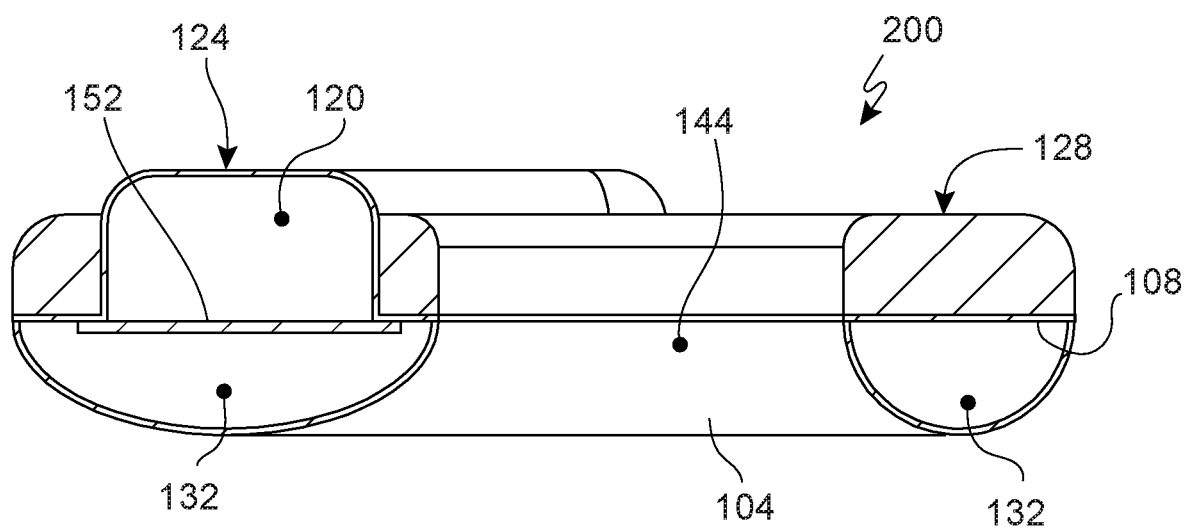
FIG. 9 is the cross-section view indicated in FIG. 8 by section lines 9-9 and looking in the direction of the arrows.

A two-reservoir embodiment is indicated generally at 200 in FIGS. 7-9. Embodiments similar to 100 and 200 may include certain elements in common, which are generally numbered accordingly. Superficially, embodiment 200 may appear to be identical to embodiment 100 in e.g., FIG. 1. However, embodiment 200 includes an internally-disposed physical barrier element 152 to define a fluid-tight separation between contact cavity 120 and bulk cavity 132. FIG. 8 illustrates barrier 152 stacked in registration on top of membrane element 108 to form a cap for cavity 120. Desirably, barrier element 152 facilitates heat transfer between media confined in respective cavities 120 and 132. Embodiment 200 therefore provides an opportunity to include different heat transfer media in each cavity. That permits tailoring a heat transfer profile or behavior for embodiment 200 compared to that available with embodiment 100.

Figure 10:
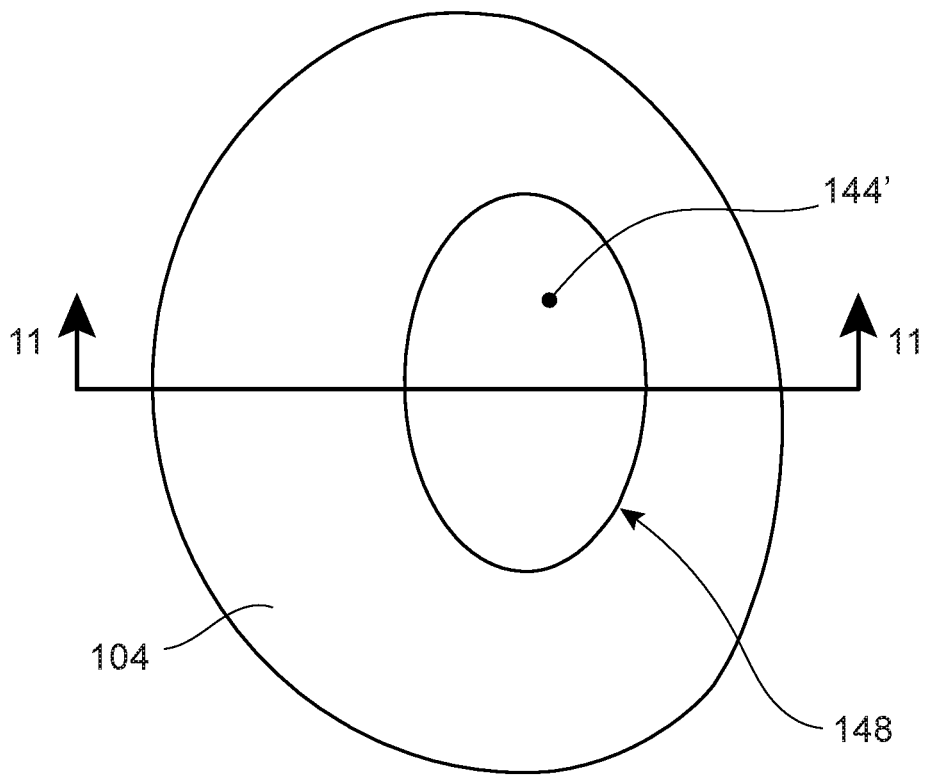
FIG. 10 is a rear plan view of a rear cover or bulk reservoir element.
Figure 11:
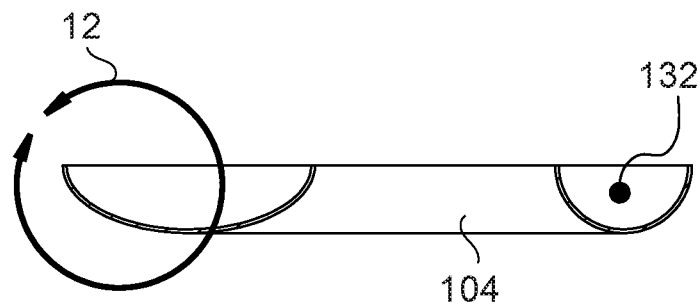
FIG. 11 is the cross-section view indicated in FIG. 10 by section lines 11-11 and looking in the direction of the arrows.
Figure 12:
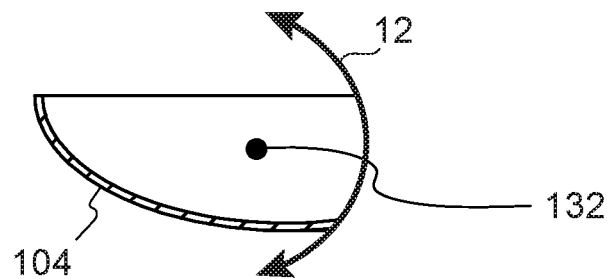
FIG. 12 is a close-up view of the detail indicated by circle 12 in FIG. 11.
Figure 13:
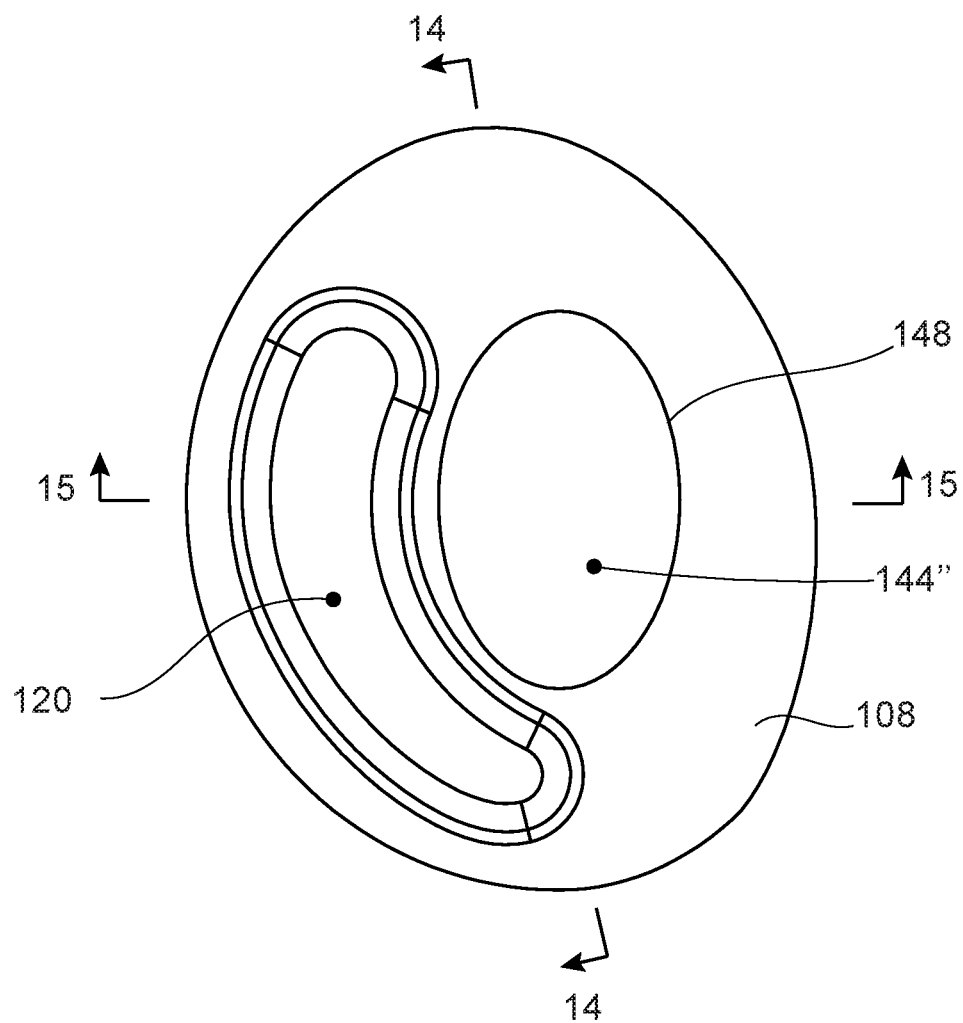
FIG. 13 is a plan view of a heat-sink reservoir element.
Figure 14:
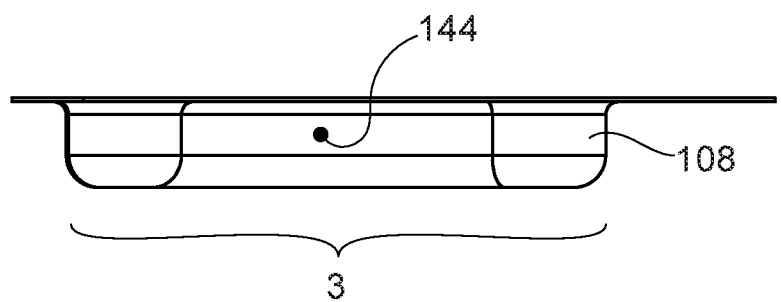
FIG. 14 is the cross-section view indicated in FIG. 13 by section lines 14-14 and looking in the direction of the arrows.
Figure 15:
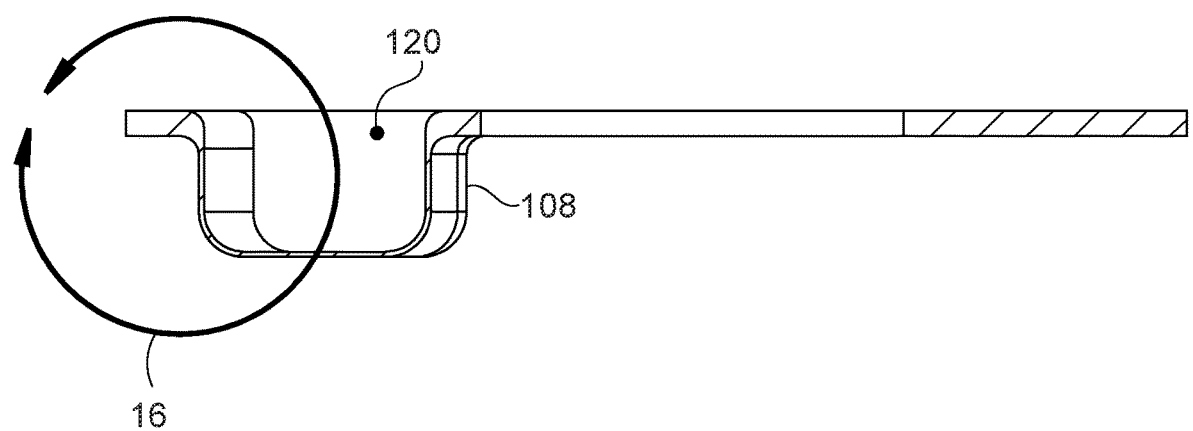
FIG. 15 is the cross-section view indicated in FIG. 13 by section lines 15-15 and looking in the direction of the arrows.
Figure 16:
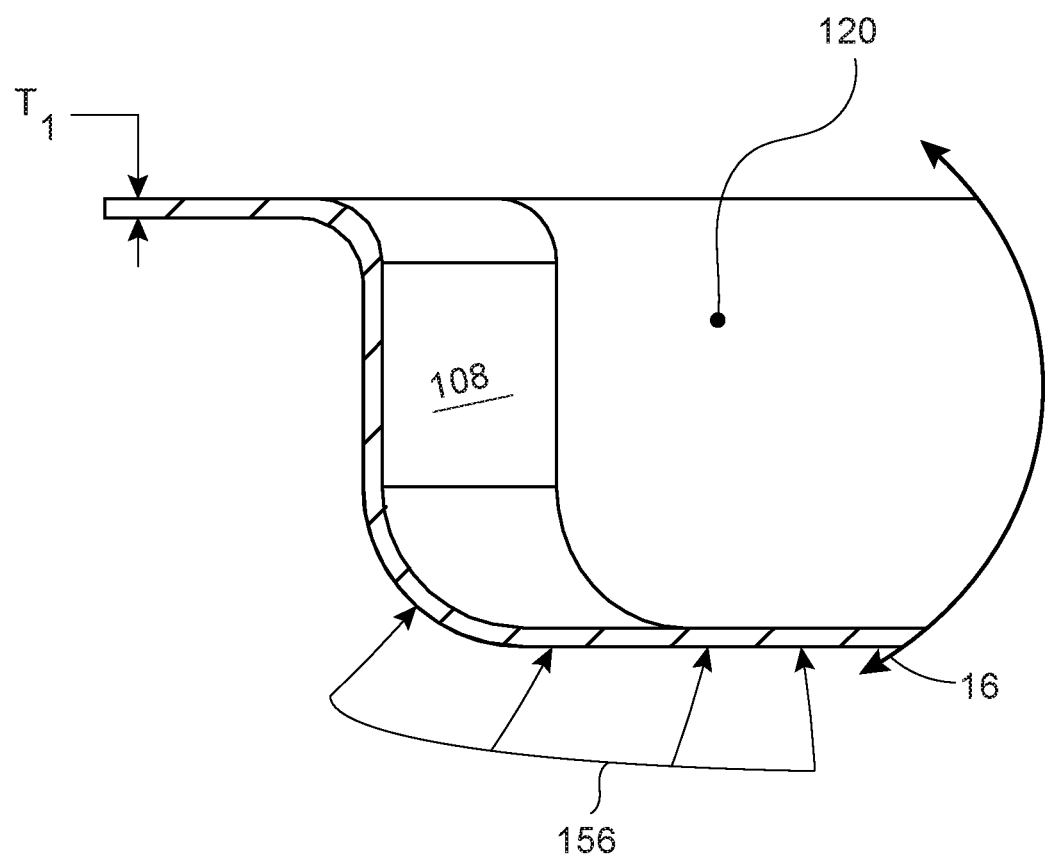
FIG. 16 is a close-up view of the detail indicated by circle 16 in FIG. 15.

Certain details of a workable rear cover 104 are illustrated in FIG. 10-12. A workable cover 104 may be formed from a flexible membrane, such as a polymer film, or from a rigid plastic, hard or firm rubber, urethane, and the like. Certain covers 104 may expand like a balloon to accommodate loading or thermal expansion e.g., of heat transfer media. A workable rear cover 104 may sometimes be insulated to resist heat transfer from the environment into the confined heat transfer media. Certain rear covers may encompass a plurality of layers of different materials to provide a desired functionality.

Certain details of a workable membrane 108 are illustrated in FIGS. 13-16. A membrane may be fashioned by heat-forming, blow-molding, injection molding, or other known manufacturing method to generate a cavity defined by a membrane or thin wall. A currently preferred membrane 108 is made from polymer film having a thickness $T_1$ (see FIG. 16) of about 0.005-0.010" thickness. A preferred material includes a stretchable polymer film (e.g., polyethylene (LDPE, HDPE, LLDPE), polyester, nylon, Teflon, etc.). Such material may be used to manufacture either/both of cavities 120 and 132. The membrane/film desirably providing a deformable wall to contact and conform to, or register in engagement with, a contact patch of a user's head surface responsive to an applied pressure profile 156. The membrane forming patient-contact cavity 120 also preferably facilitating heat transfer there-through.

Figure 17:
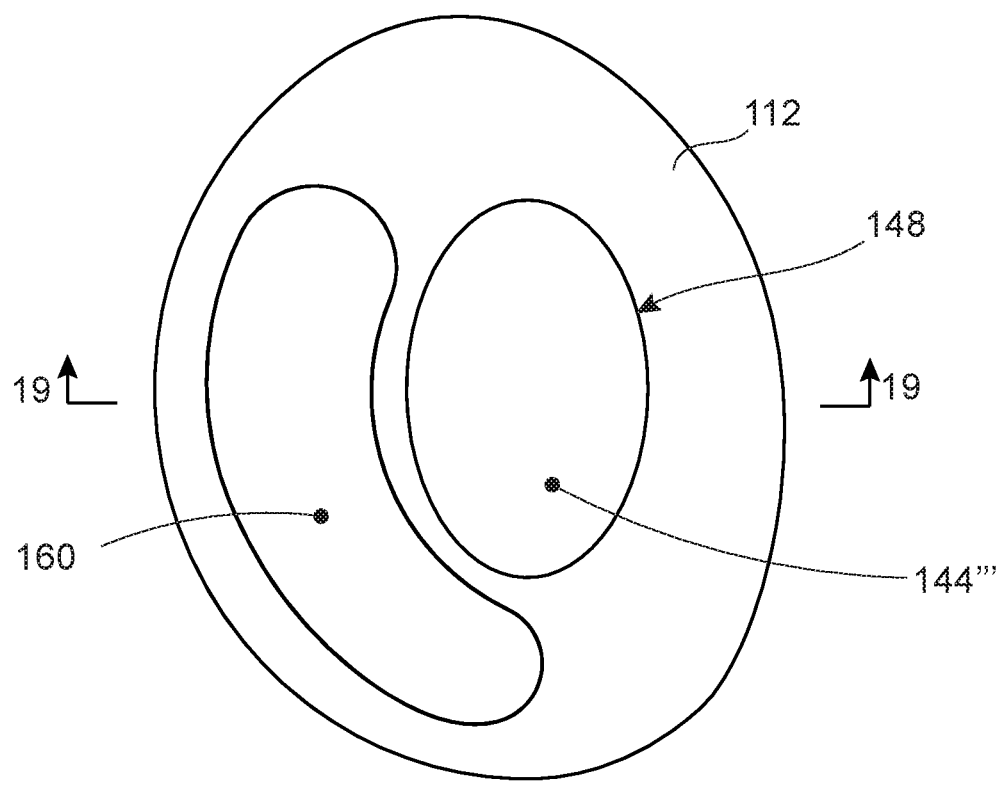
FIG. 17 is a plan view of an insulator element.
Figure 18:
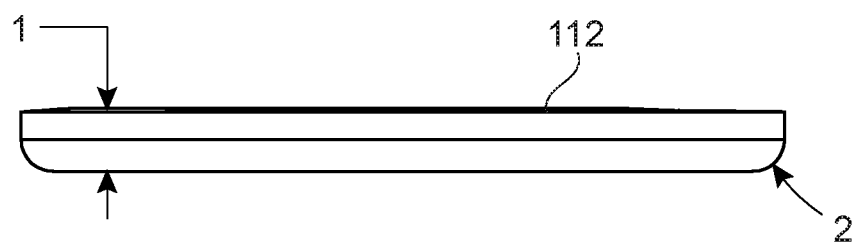
FIG. 18 is a side view of the insulator element in FIG. 17.
Figure 19:
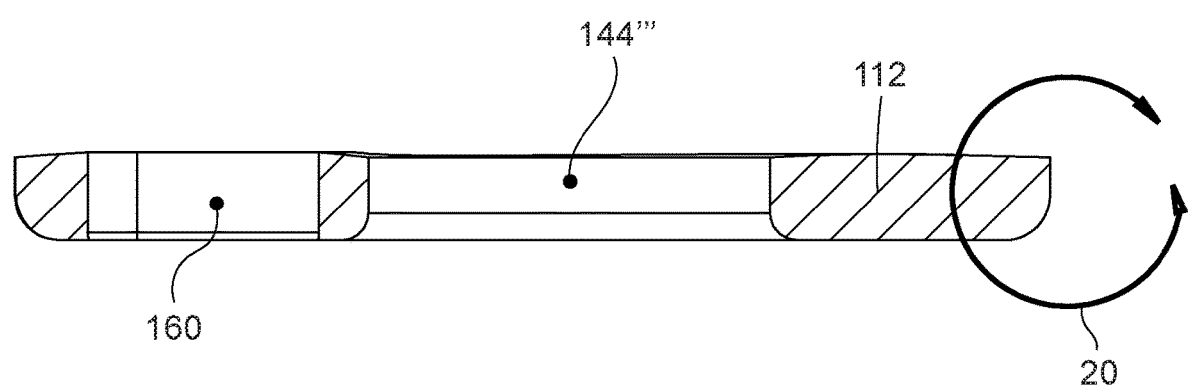
FIG. 19 is the cross-section view indicated in FIG. 17 by section lines 19-19 and looking in the direction of the arrows.
Figure 20:
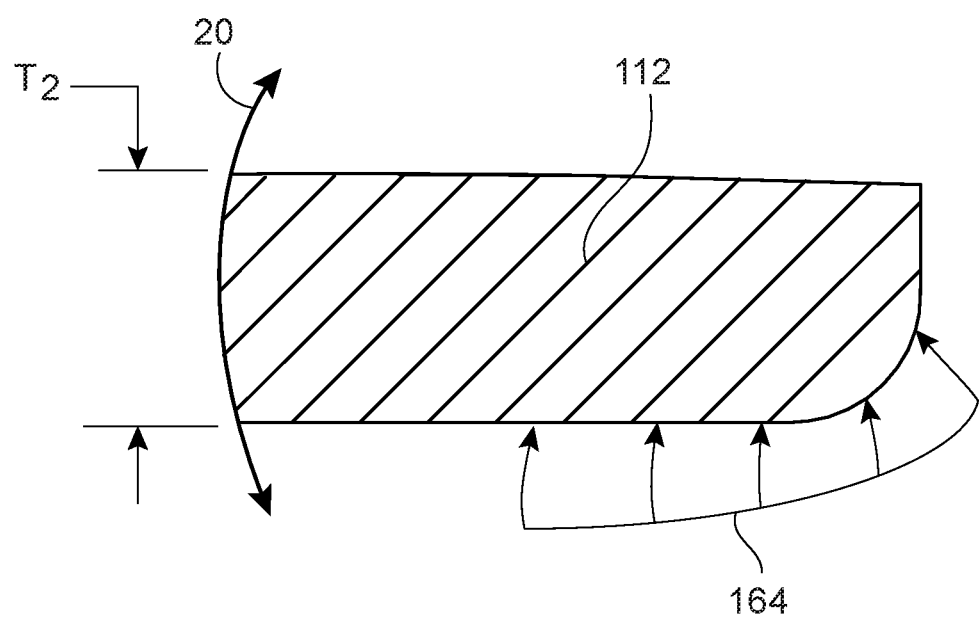
FIG. 20 is a close-up view of the detail indicated by circle 20 in FIG. 19.

Certain details of a workable insulator 112 are illustrated in FIGS. 17-18. A workable insulator resists heat transfer, and may be manufactured from open-cell foam, thermally-resistant material, skinned poly foam, or the like. Portions of an insulator 112 also may contact a patient's head, and are typically deformable or may be pre-shaped in a variety of different assemblies to comfortably accommodate between head shapes of different patients. The insulator 112 desirably providing a deformable surface to contact and conform to a patient's head responsive to an applied pressure profile 164. A currently preferred insulator 112 is made from foam having a thickness $T_2$ (see FIG. 20) of about 0.125-0.5" in thickness. A workable material to form an insulator 112 includes open/closed cell, thermally insulating polymer foam or rubber (closed cell/rubber, e.g., EPDM, neoprene, silicone, PVC, and polypropylene; open cell, e.g., polyurethane foam, open cell rubber).

The various elements may be fused together thermally, joined mechanically, or bonded with adhesives, and the like. Alternative manufacturing methods and suitable materials of construction will be apparent to one of ordinary skill in the art.

Figure 21:
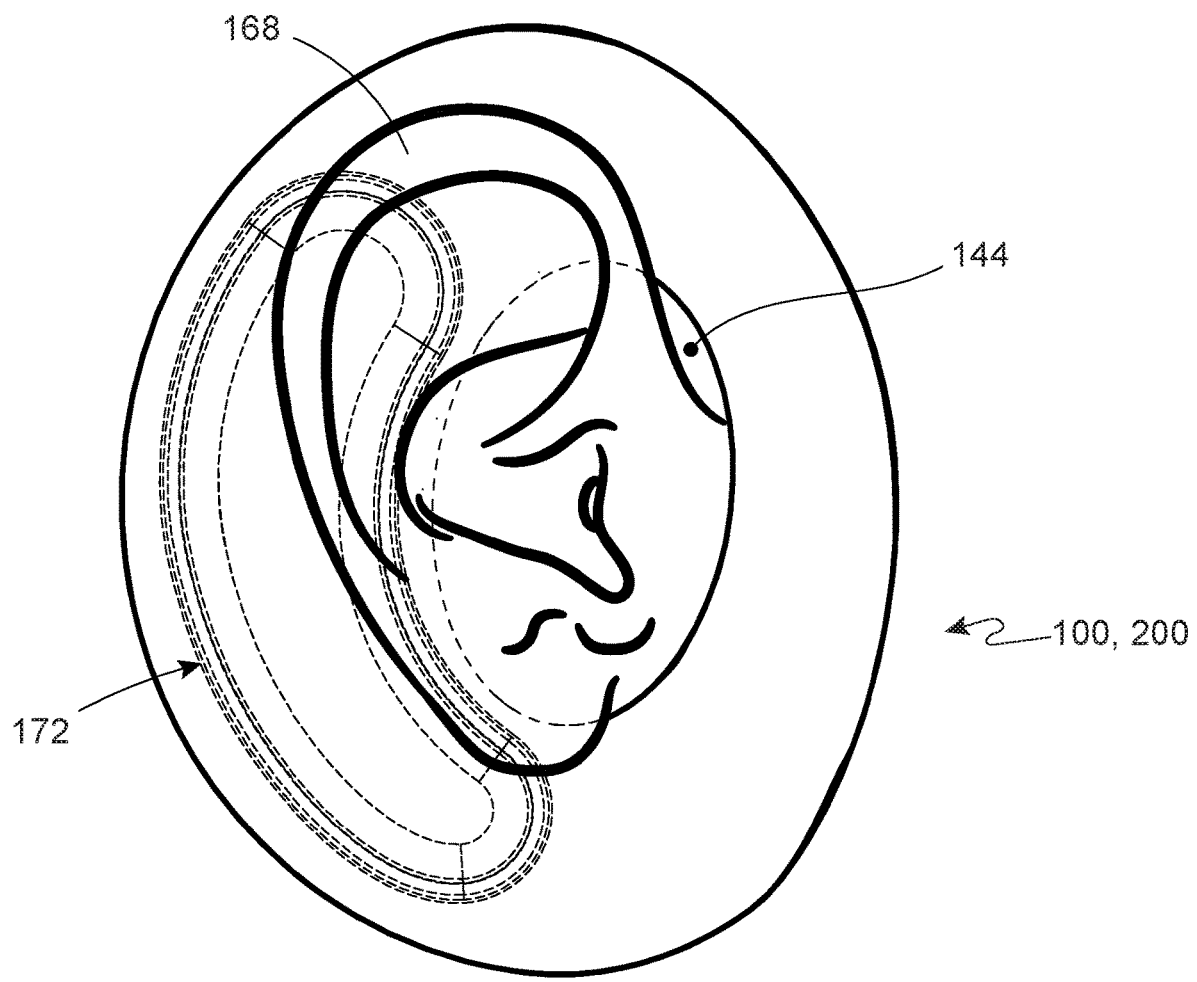
FIG. 21 illustrates a device according to certain principles of the invention installed with reference to an ear on a human head.
Figure 22:
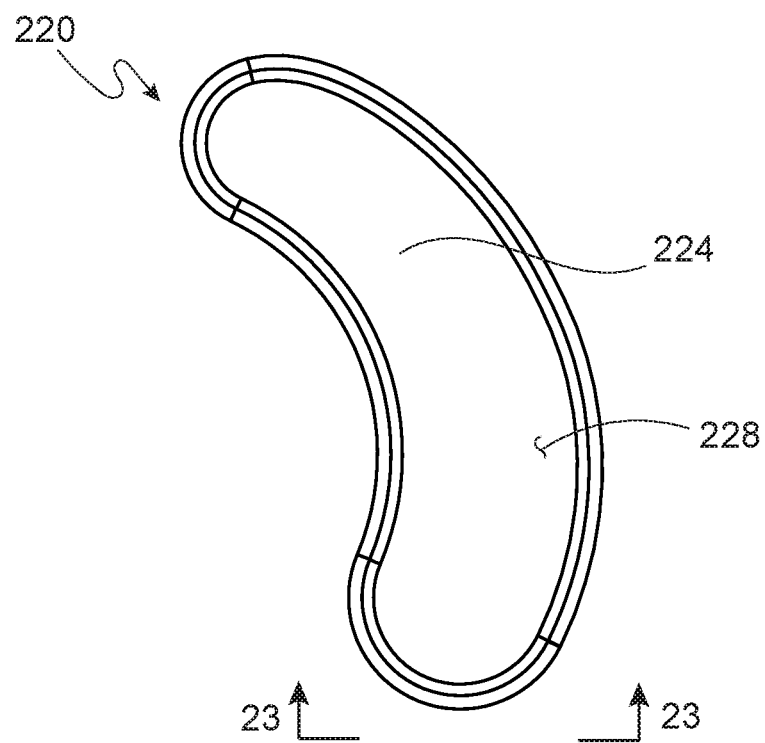
FIG. 22 is a plan view of another embodiment of a localized cooling pack assembly structured according to certain principles of the invention.
Figure 23:
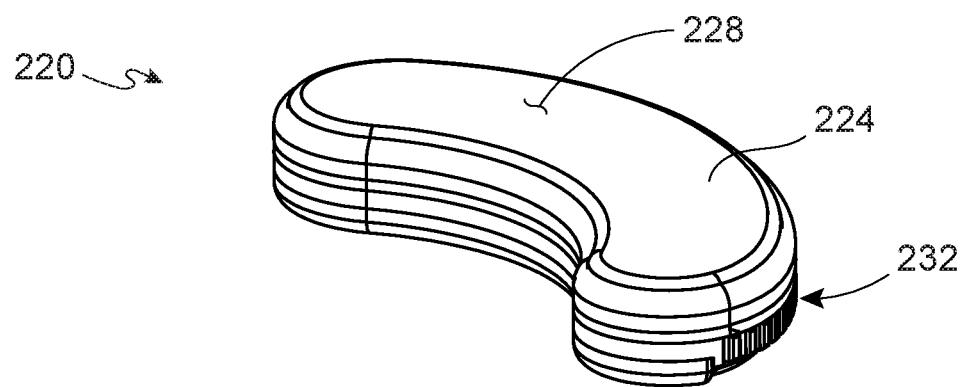
FIG. 23 is a perspective view of the embodiment in FIG. 22.

With reference now to FIG. 21, an embodiment such as 100 or 200 is illustrated in installed registration with respect to an ear 168 of a patient. Note that a portion of an installed device 100, 200 is desirably located between the ear "flap", or helix, and the skin covering the patient's skull. One desired localized area of applied cooling (heat extraction or heat removal from the patient's head) is indicated by phantom-line structure indicated at 172.

Another embodiment is indicated generally at 220 and is described with reference to FIGS. 22-29. Embodiment 220 is an active device, and includes electronic components that provide heat transfer from a localized area of a patient's head. An active device such as 220 may sometimes include one or more passive component, which can be pre-cooled (e.g., frozen). Certain active devices 220 may extend thermal therapy for a time beyond the capability of a passive device, and may provide a desired programmable and time-variable cooling profile to a patient.

Figure 24:
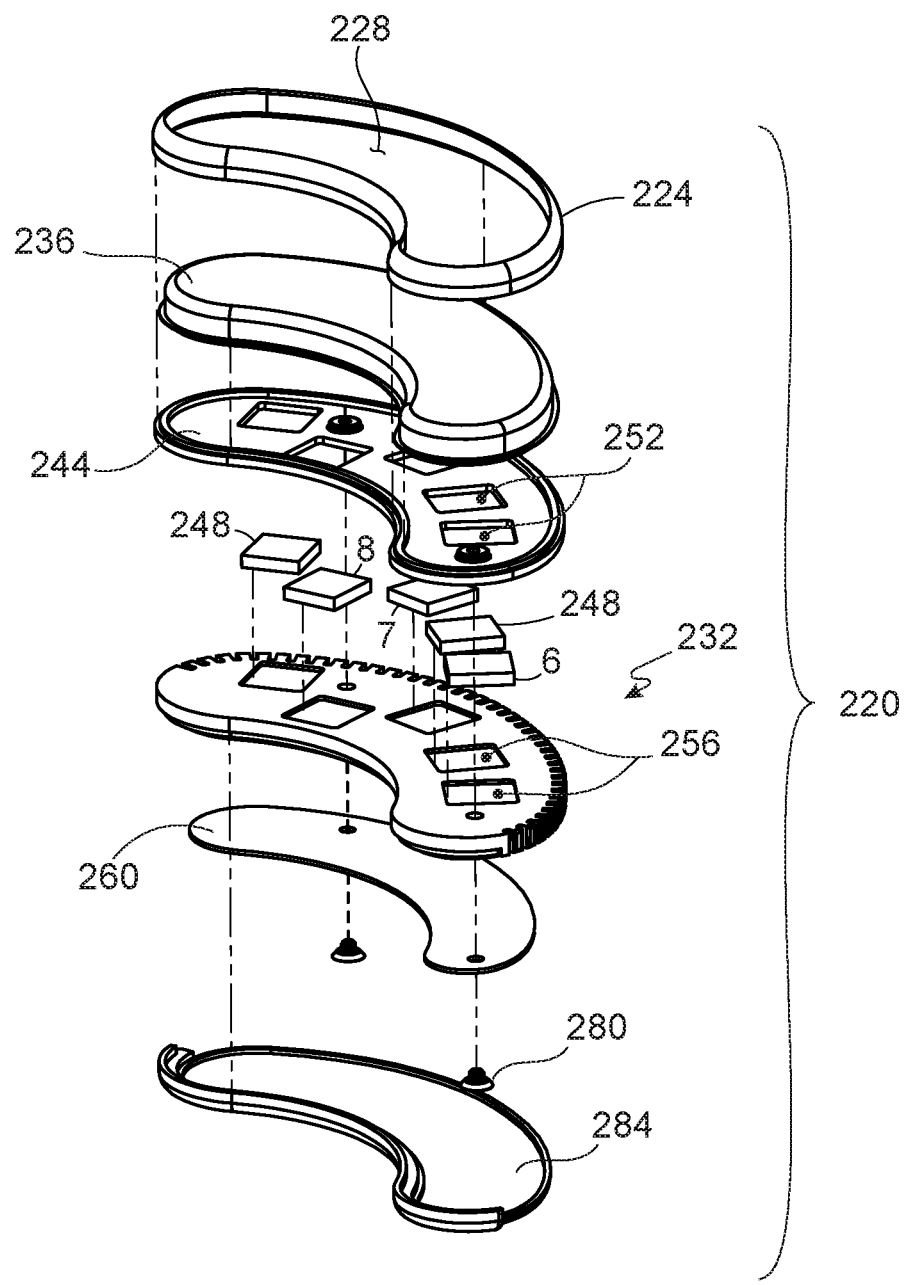
FIG. 24 is an exploded assembly view of the embodiment in FIG. 22.
Figure 25:
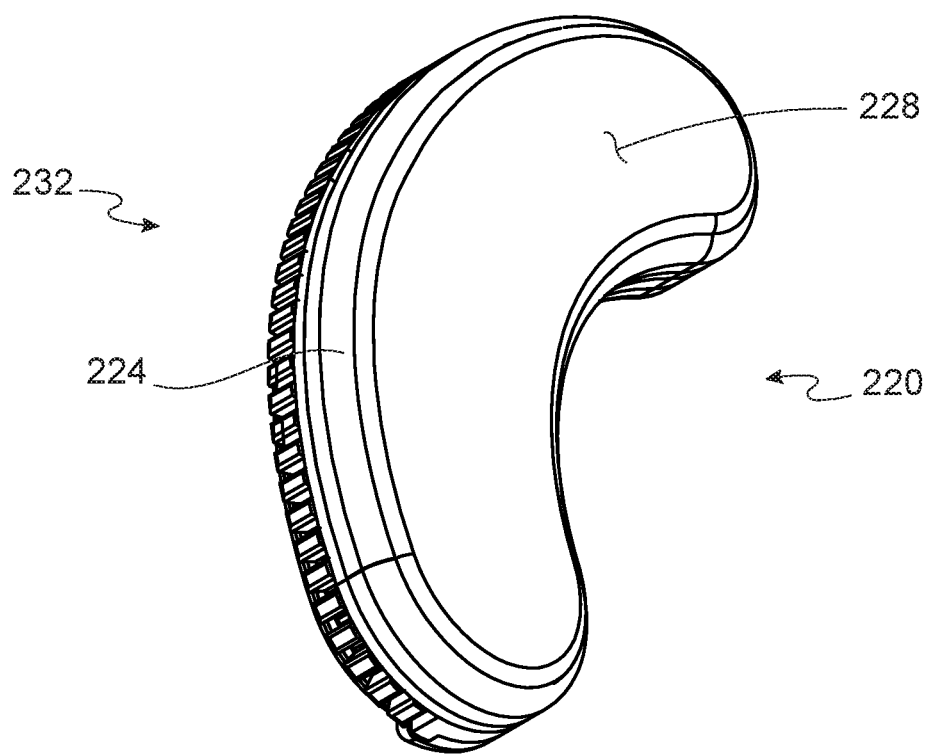
FIG. 25 is another perspective view of the embodiment in FIG. 22.
Figure 26:
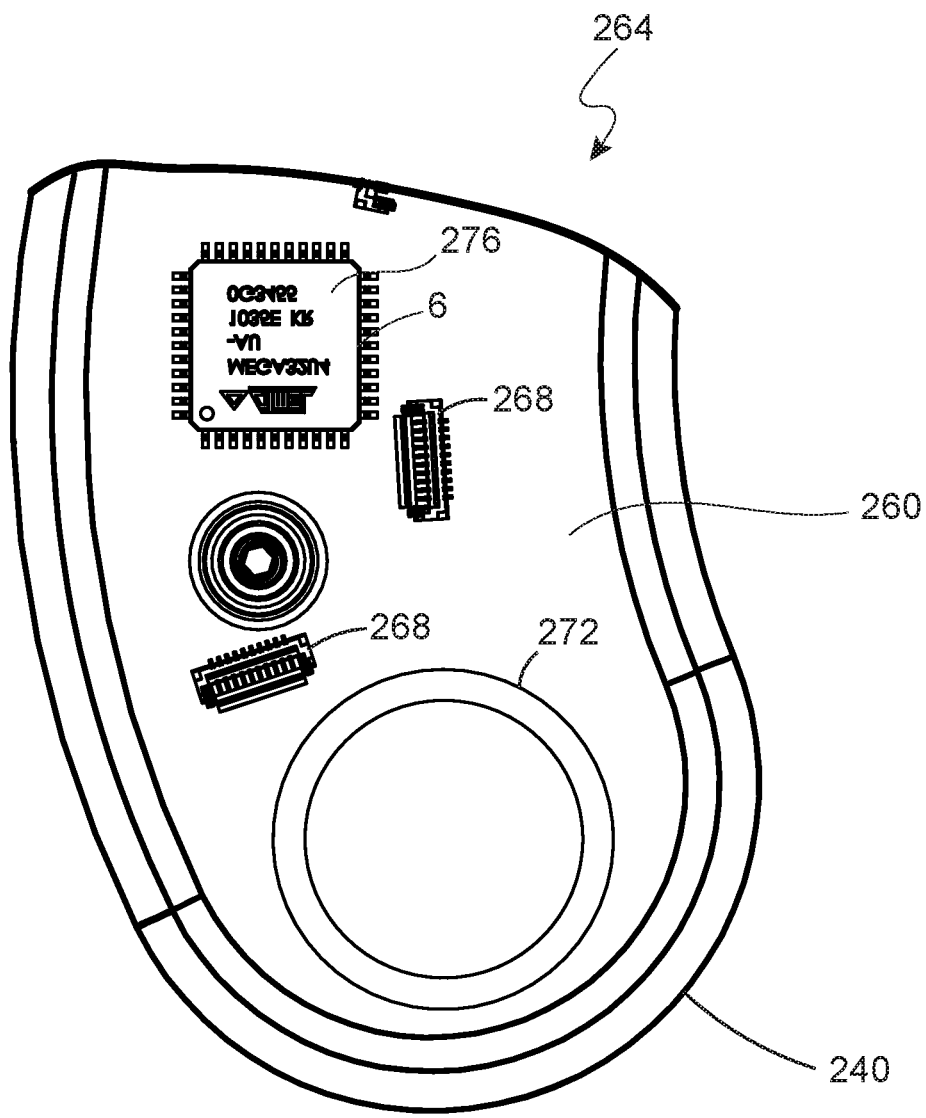
FIG. 26 is a close-up view of a portion of the embodiment in FIG. 22, partially disassembled.
Figure 27:
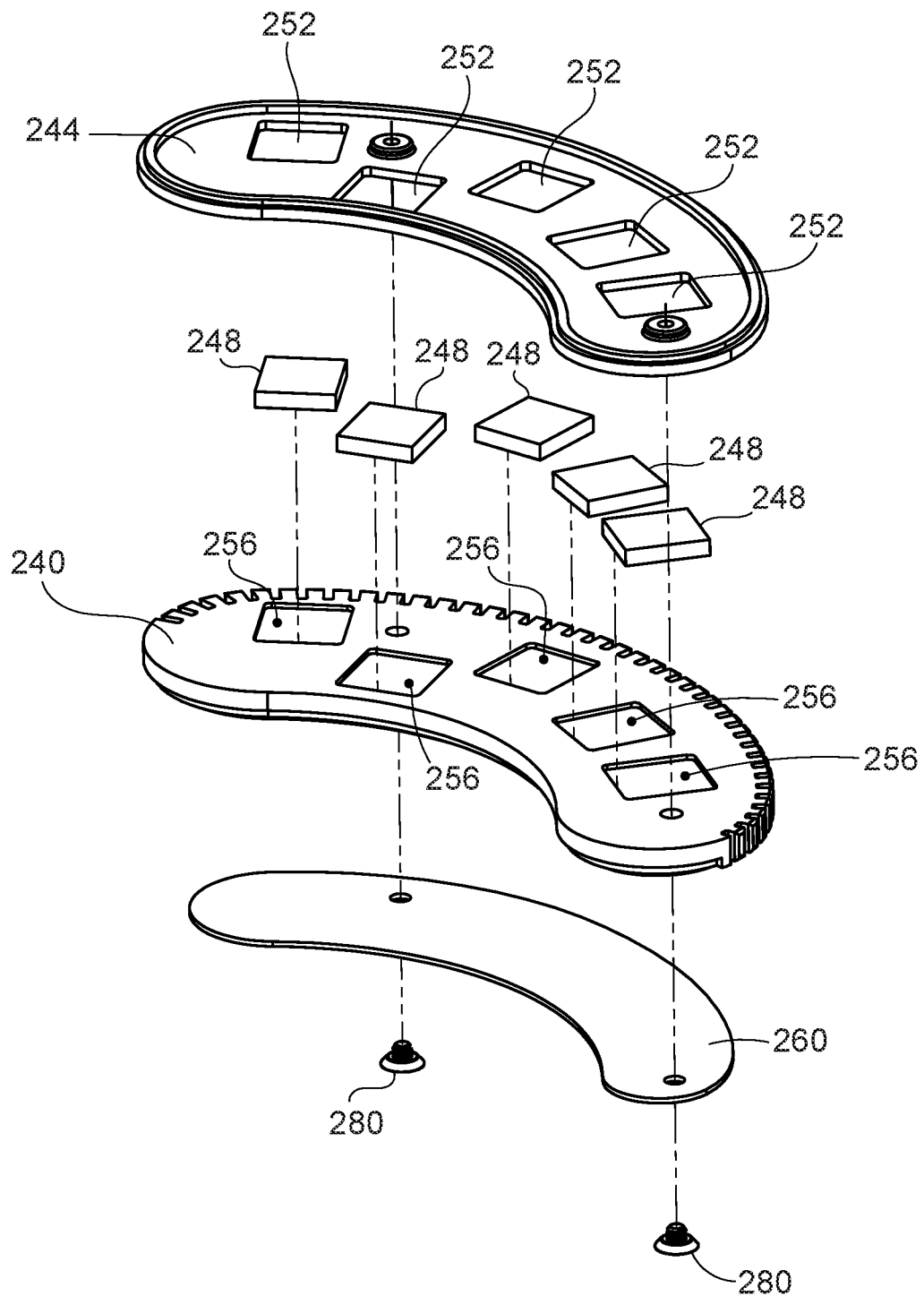
FIG. 27 is an exploded assembly view of a subassembly of the embodiment in FIG. 22.

Active device 220 includes a front cover 224 with a surface 228 structured and disposed for contact to the skin surface behind a patient's ear. A preferred cover 224 is flexible and accommodating to a patient's head shape. A heat-dissipating element, generally 232, is structured to dump heat from the device 220 to the local environment. An operable heat-dissipating element includes a series of fins and gaps provided in a thermally conductive heat sink material. With particular reference to FIGS. 24 and 27, a bladder 236 is installed in registration in contact with cover 224, and functions to draw heat from the patient's localized therapy area. A bladder 236 carries a heat transfer media, and may be pre-cooled (e.g., frozen like a passive ice pack). Bladder 236 is spaced apart from a heat sink element 240 by an insulating layer 244.

One or more (as illustrated, a plurality) thermoelectric heat transfer element 248 can be disposed to transport heat from the bladder 236 to the heat sink element 240. A workable heat sink element 240 may be manufactured from metal. A workable thermoelectric element 248 includes a Peltier device. A cooperating window 252 provides through-penetration of a device 248 and permits the cold side of an element 248 to contact and extract heat from the bladder 236. Sometimes, registration structure, such as a socket 256, may be provided as a manufacturing assembly aide to locate a thermoelectric device 248 with respect to the heat sink element 240.

The thermoelectric element(s) 248 are disposed in electrical communication with circuit board 260, which carries the electrical components (generally indicated at 264 in FIG. 26) for operation and control of the device 220. Electrical components that may be carried by circuit board 260 include: electrical connectors 268 to communicate with elements 248; on-board power supply, such as battery 272; and a micro-controller or integrated circuitry 276. The assembly or subassembly may be held together, at least in part, by one or more fastener 280.

A rear cover 284 provides a protective closure for the device 220. Desirably, rear cover 284 provides an insulation and spacing function to resist contact by the patient with heat sink element 240. In the illustrated embodiment, rear cover 284 is bonded around a portion of its perimeter to front cover 224.

Figure 28:
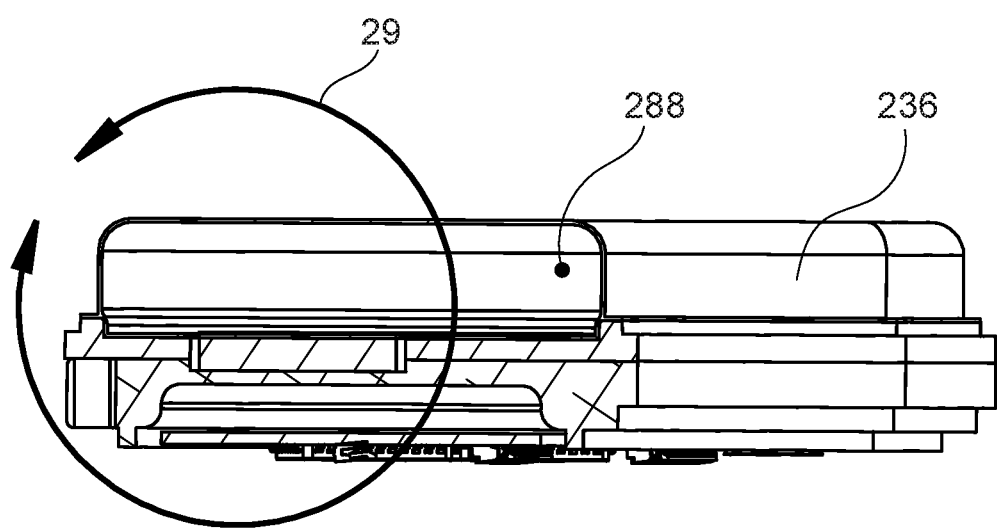
FIG. 28 is a cross-section view of the device in FIG. 23, with the top and bottom covers removed.
Figure 29:
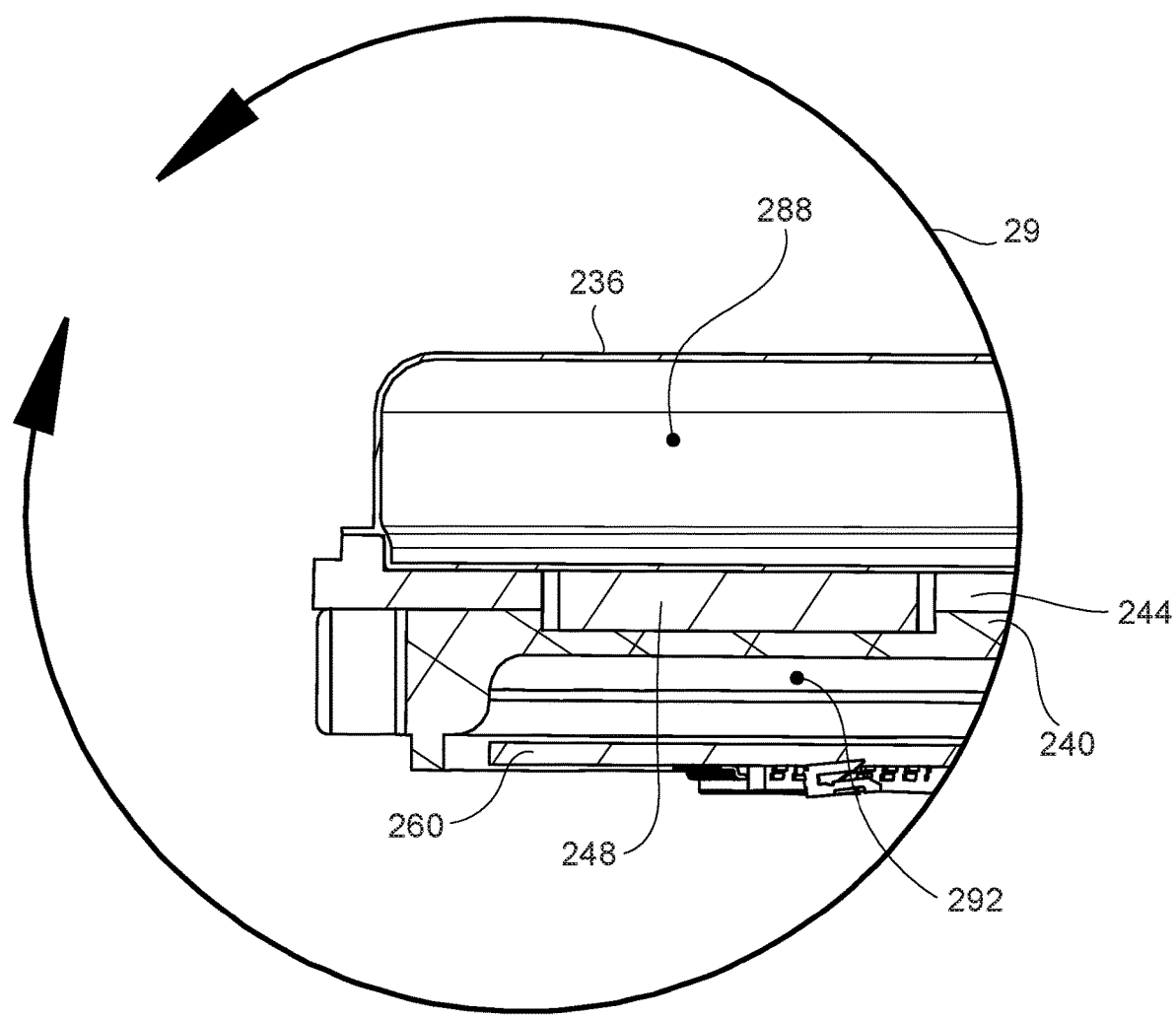
FIG. 29 is a close-up view of the detail indicated by circle 29 in FIG. 28.

With reference now to FIGS. 28 and 29, it can be seen how the various electronic and mechanical elements cooperate to cool heat transfer media confined inside the volume 288 defined by a bladder 236. An air gap 292 is provided to facilitate performance of the heat dissipation structure 232. Currently, air circulation through gap 292 is promoted by convection. Incorporation of a fan to drive air flow is within contemplation.

Figure 30:
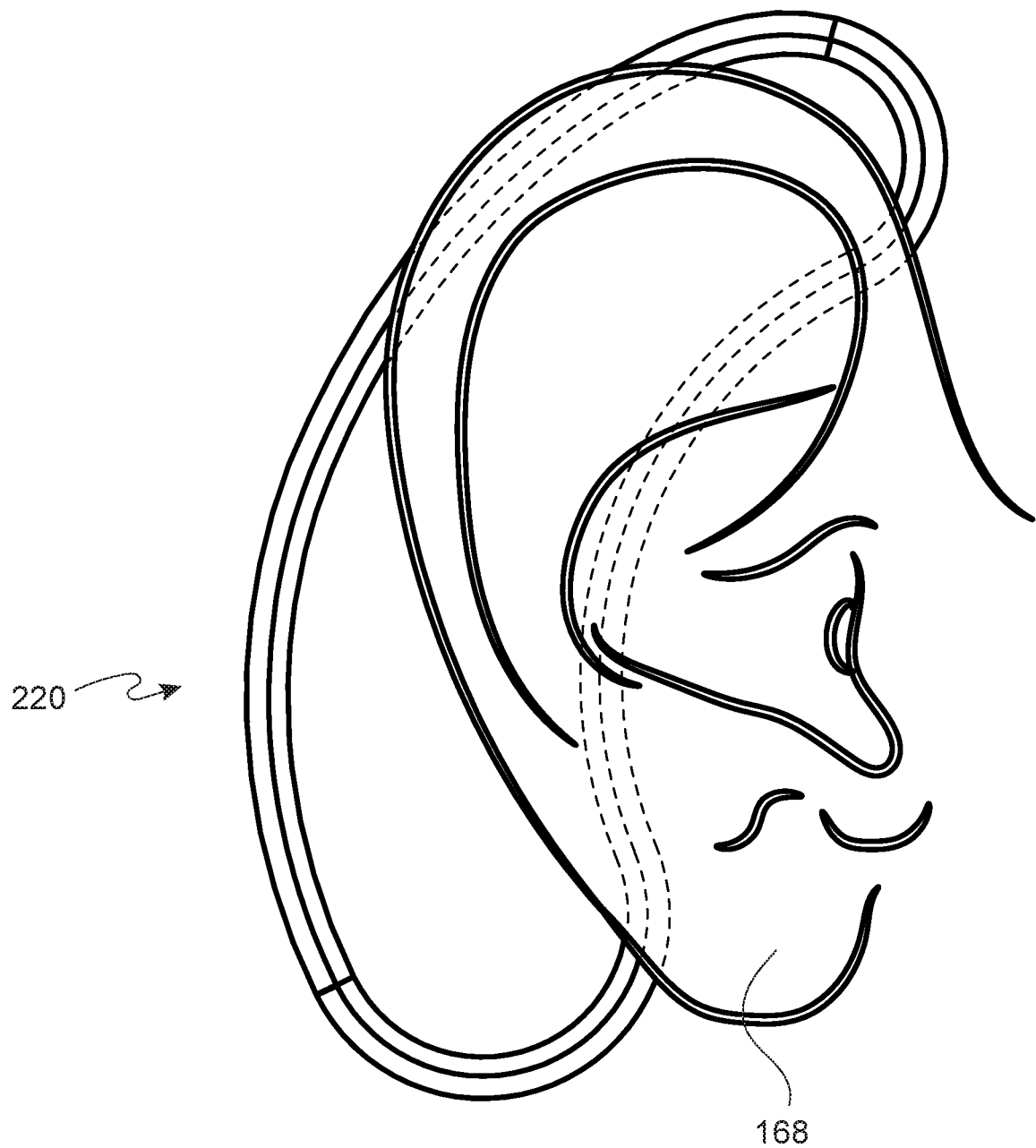
FIG. 30 illustrates another device according to certain principles of the invention installed with reference to an ear on a human head.
Figure 31:
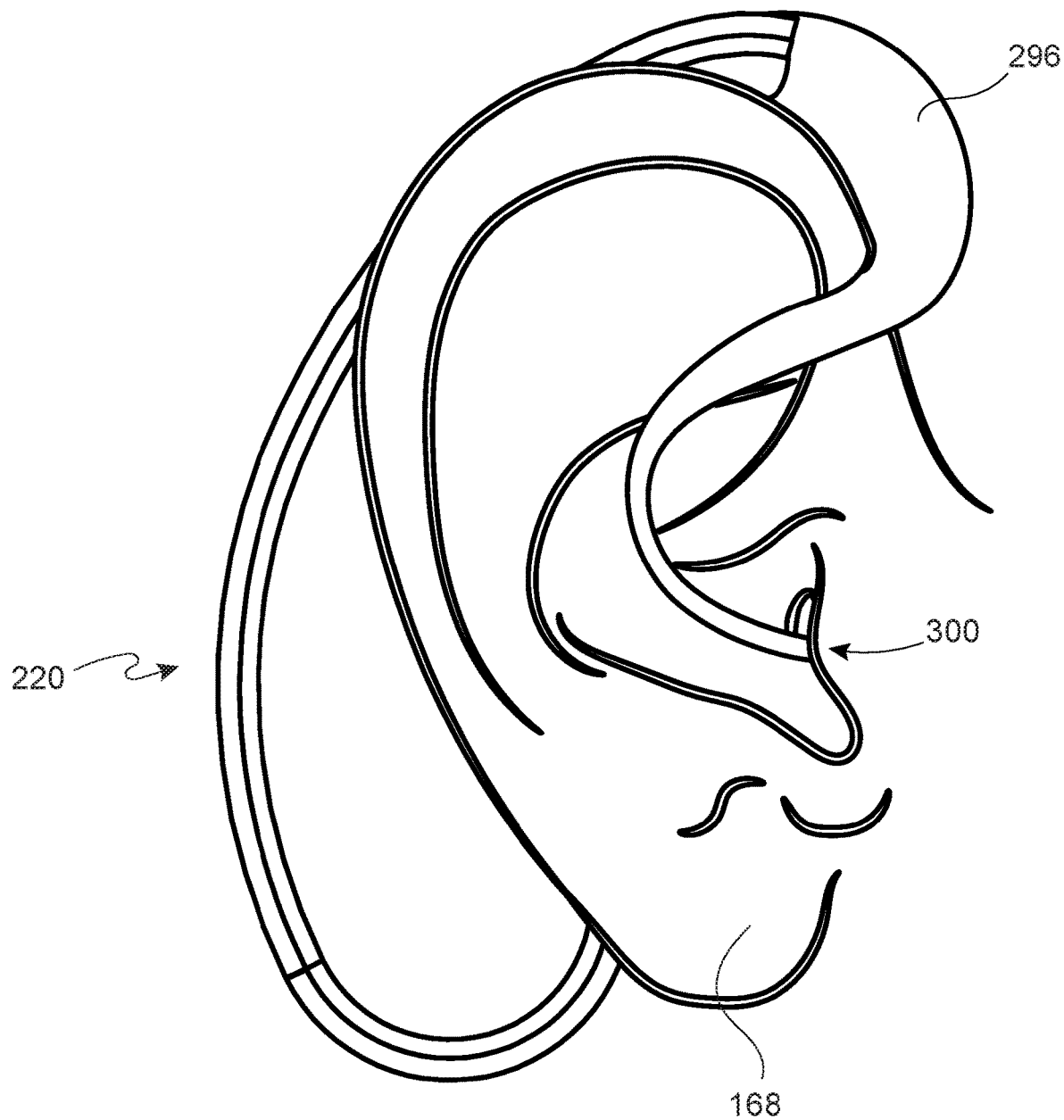
FIG. 31 illustrates another device according to certain principles of the invention installed with reference to an ear on a human head.
Figure 32:
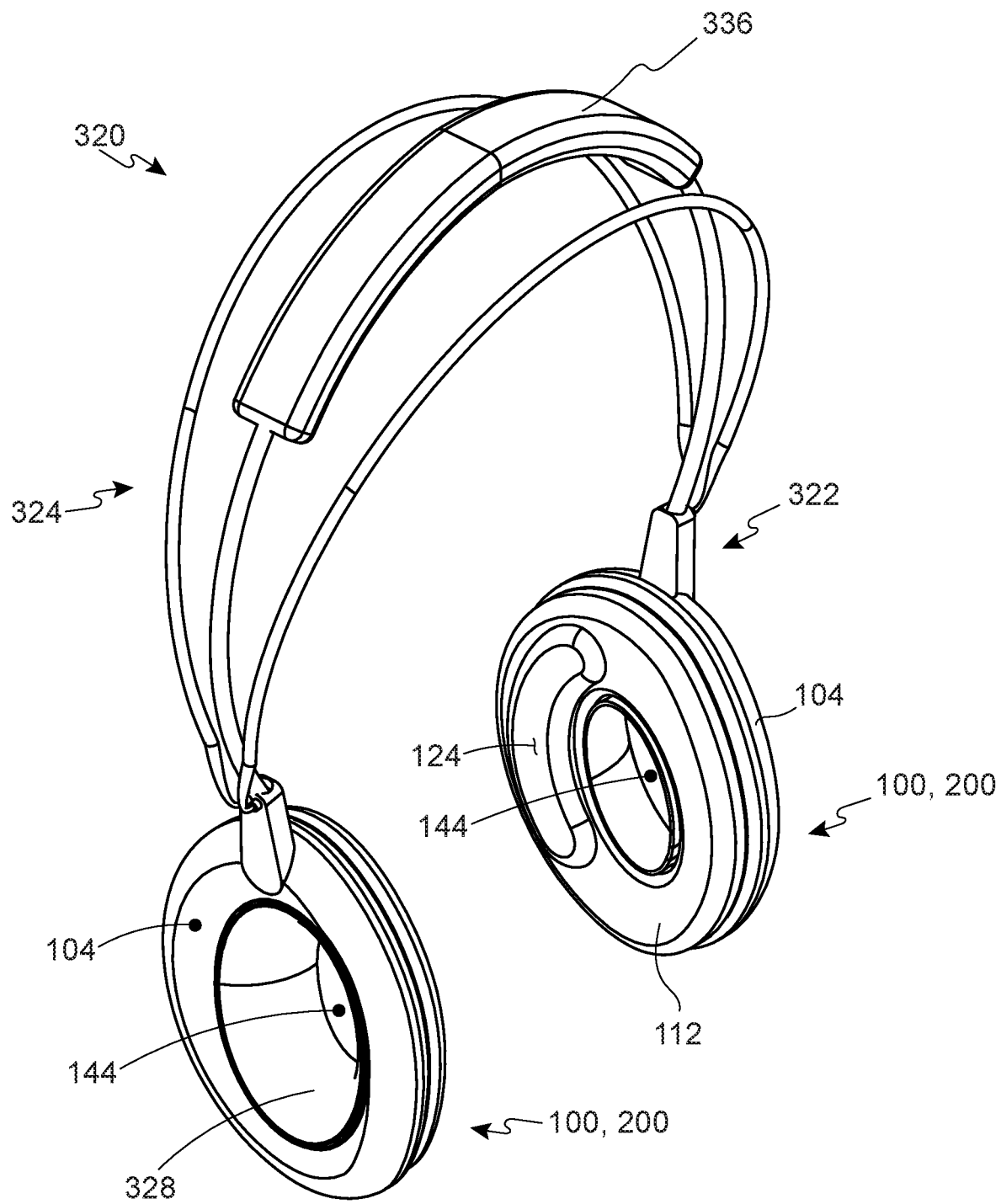
FIG. 32 is a perspective view illustrating an embodiment structured similar to conventional earphones.
Figure 33:
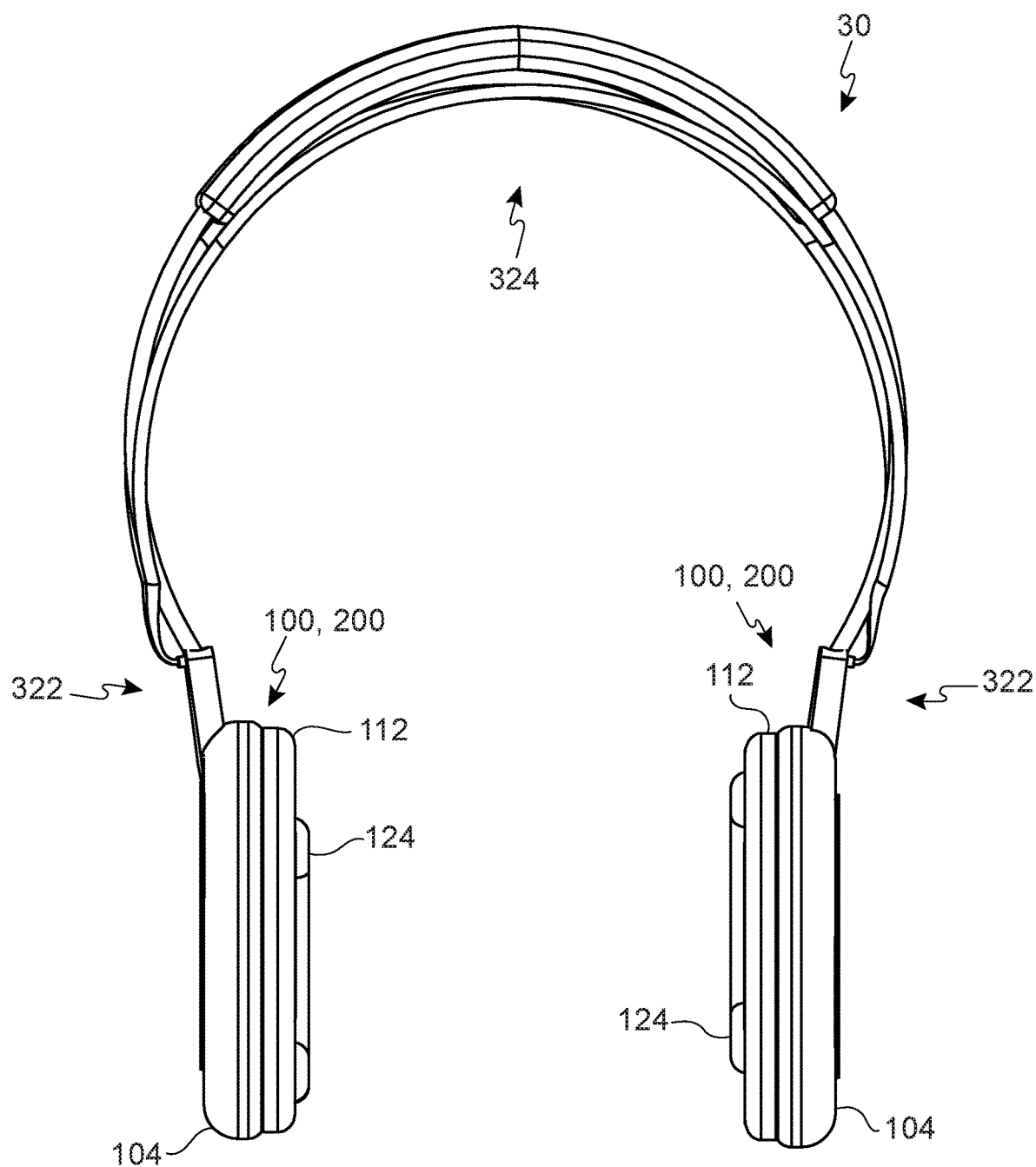
FIG. 33 is a rear view in elevation of the embodiment in FIG. 32.
Figure 34:
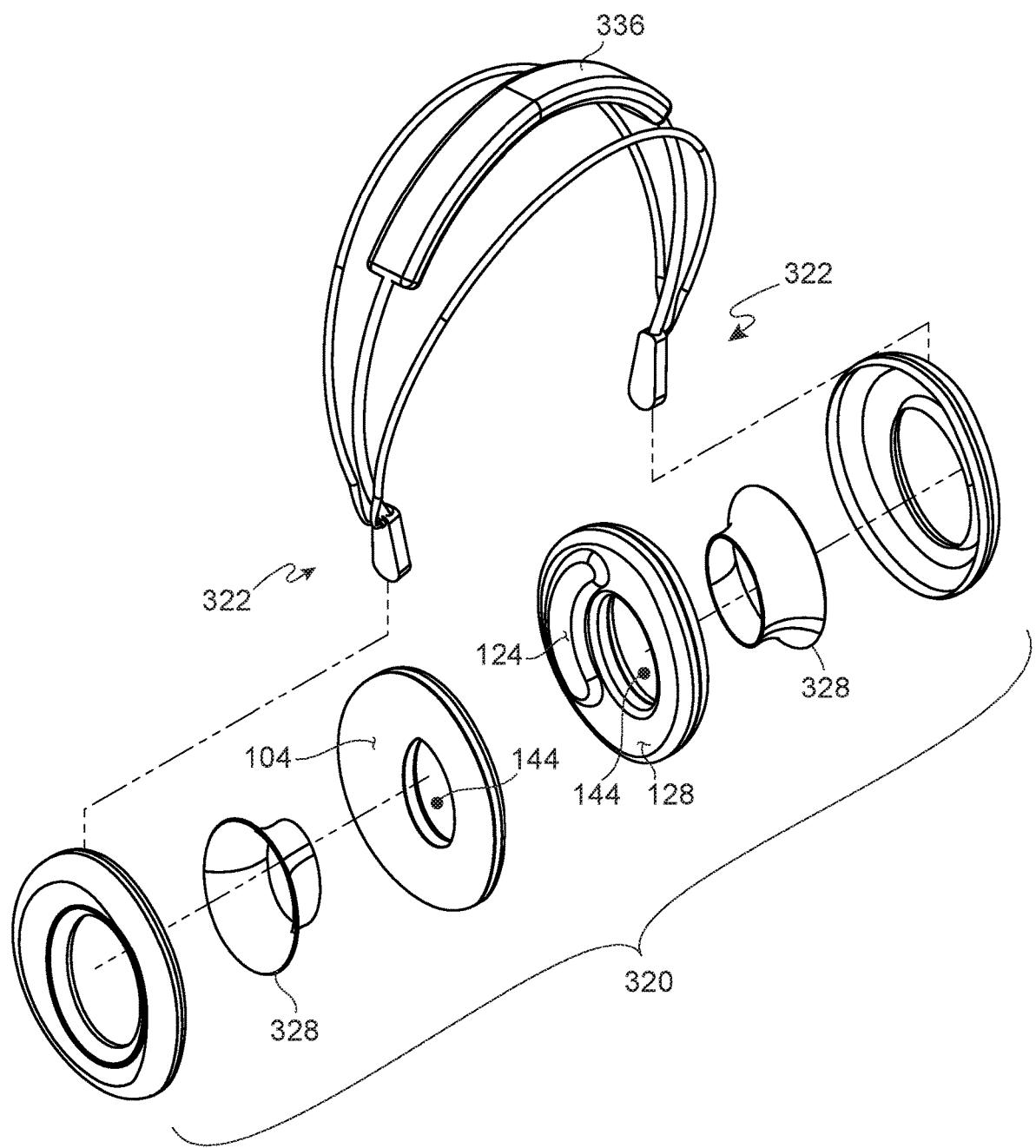
FIG. 34 is an exploded assembly view of the embodiment in FIG. 32.
Figure 35:
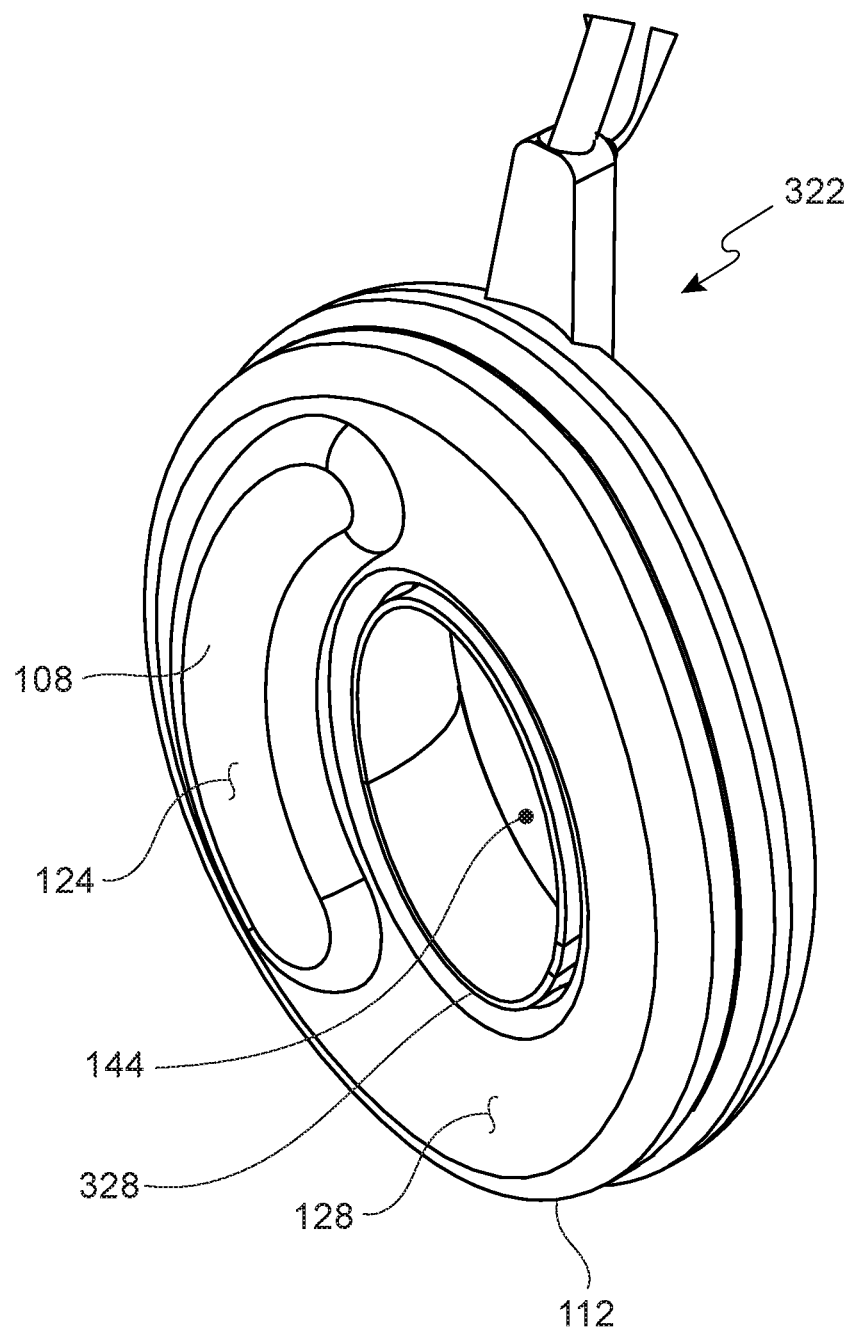
FIG. 35 is a perspective view at the inside, or head-contacting part, of a cooling pack illustrated in FIG. 32.

FIG. 30 illustrates an active embodiment 220 installed in registration with an ear 168 on a human head. An active embodiment 220 may alternatively be replaced by an entirely passive thermal therapy device having a cooperating size and configuration. An embodiment with an external configuration similar to that illustrated in FIG. 30 may be temporarily bonded onto the skin posterior to a patient's ear, or secured with tape or a wrap, or other workable retention structure. FIG. 31 illustrates optional mounting structure 296 affixed to a thermal therapy device and extending over the lateral side of the ear 168. In certain cases, and as illustrated, mounting device 296 may include a portion, generally 300, that extends into the ear canal for additional installation security. Mounting structure 296 may alternatively terminate with structure shaped to register with alternative cooperating and laterally-exposed portions of structure of the patient's ear (loops, swirls, sockets, etc.).

The embodiment indicated generally at 320 in FIGS. 32-35 includes a pair of thermal therapy packs associated with a head band 324, similar to conventional stereo headphones. Although the illustrated thermal packs are externally structured according to embodiments 100 and 200, it is within contemplation that one or both may be replaced with an embodiment including an active heat transfer element.

Of note, embodiment 320 also illustrates optional ear cone elements 328. Cone elements 328 are structured from resilient elastic material that may stretch to facilitate installation of an ear there-through, and for comfort of an installed device. Desirably, the cone elements 328 improve a grip on outer structure of an ear 168 by an installed thermal therapy device. During installation, an ear helix is drawn through the opening 144 of each cooling pack. It is currently desired for the ear cones 328 to be open at each end, to avoid interfering with the hearing of a patient that is undergoing thermal therapy. An operable ear cone 328 can be affixed to a thermal therapy device at a large diameter open end, leaving a free-standing conic section that extends to a smaller diameter opening disposed at the opposite end of the cone. The smaller diameter conic opening may facilitate positioning of a cooling portion 124 in registration near the base of the ear/skull junction, as well as to help grip the ear near its cantilever base. As illustrated in e.g., FIG. 34, an ear cone 328 may be affixed to a shell element 330, and the shell element 330 may be associated with a thermal therapy device. Other arrangements will be readily apparent to one of ordinary skill.

Connection structure, generally 332, may be included to facilitate coupling/decoupling a cooling pack to the headband 324. Connection structure 332 permits removal of a device for pre-cooling without exposing the entire assembly 320 to thermal change and potential temperature or condensate-induced damage. Desirably, a cooling device 100, 200, etc., is mounted with respect to the headband 324 to permit adjusting the device and band 324 to fit a device comfortably in registration on both sides of a patient's head. Typically, that includes degrees of freedom for rotation of each device about horizontal and vertical axes, and a length adjustment of band 324 between the devices. Also, headband 324 may include a compartment 336 in which to dispose electronics, power supply, wireless communication, control circuitry, and the like.

Figure 36:
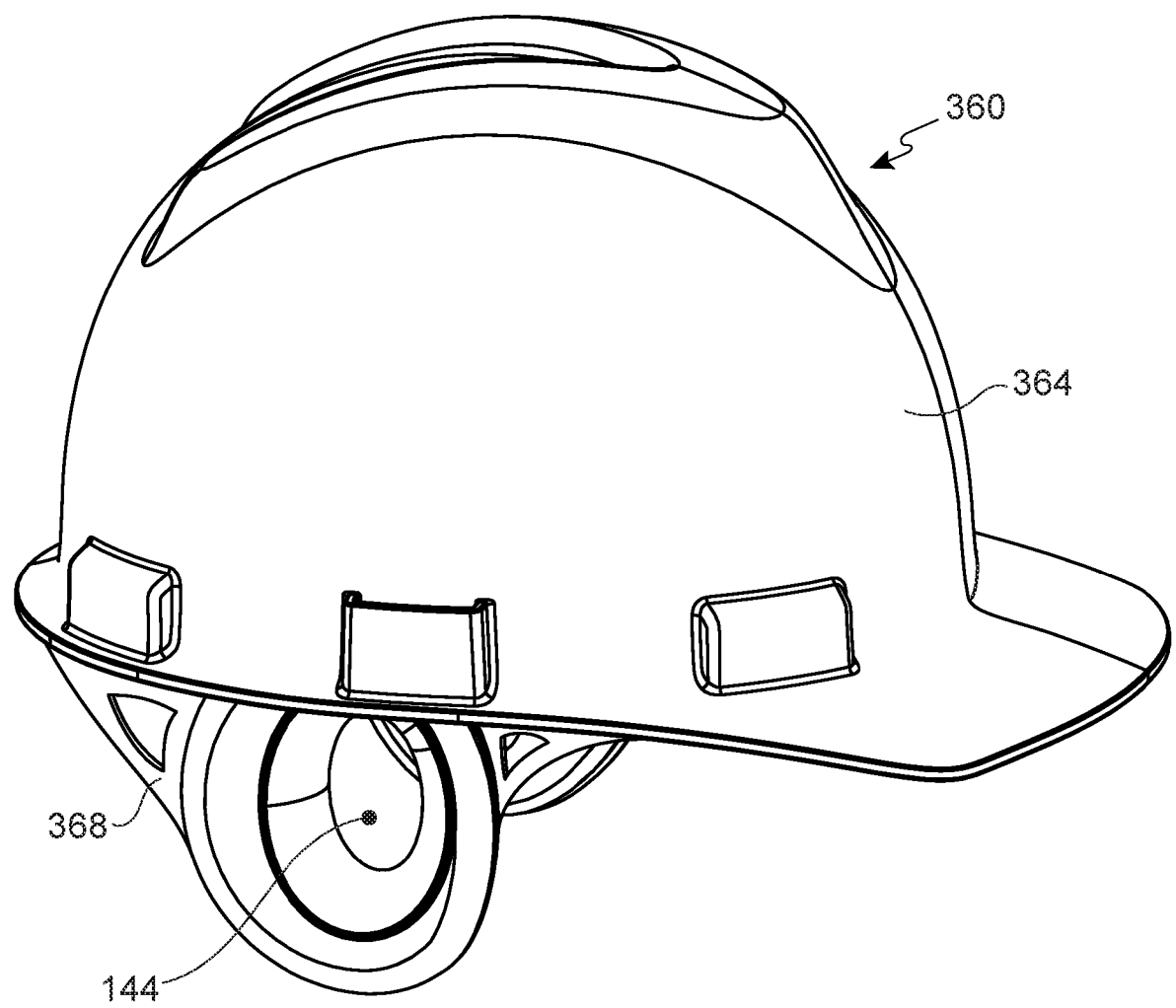
FIG. 36 is a perspective view, slightly from above, illustrating an embodiment adapted for association with a helmet or hat.
Figure 37:
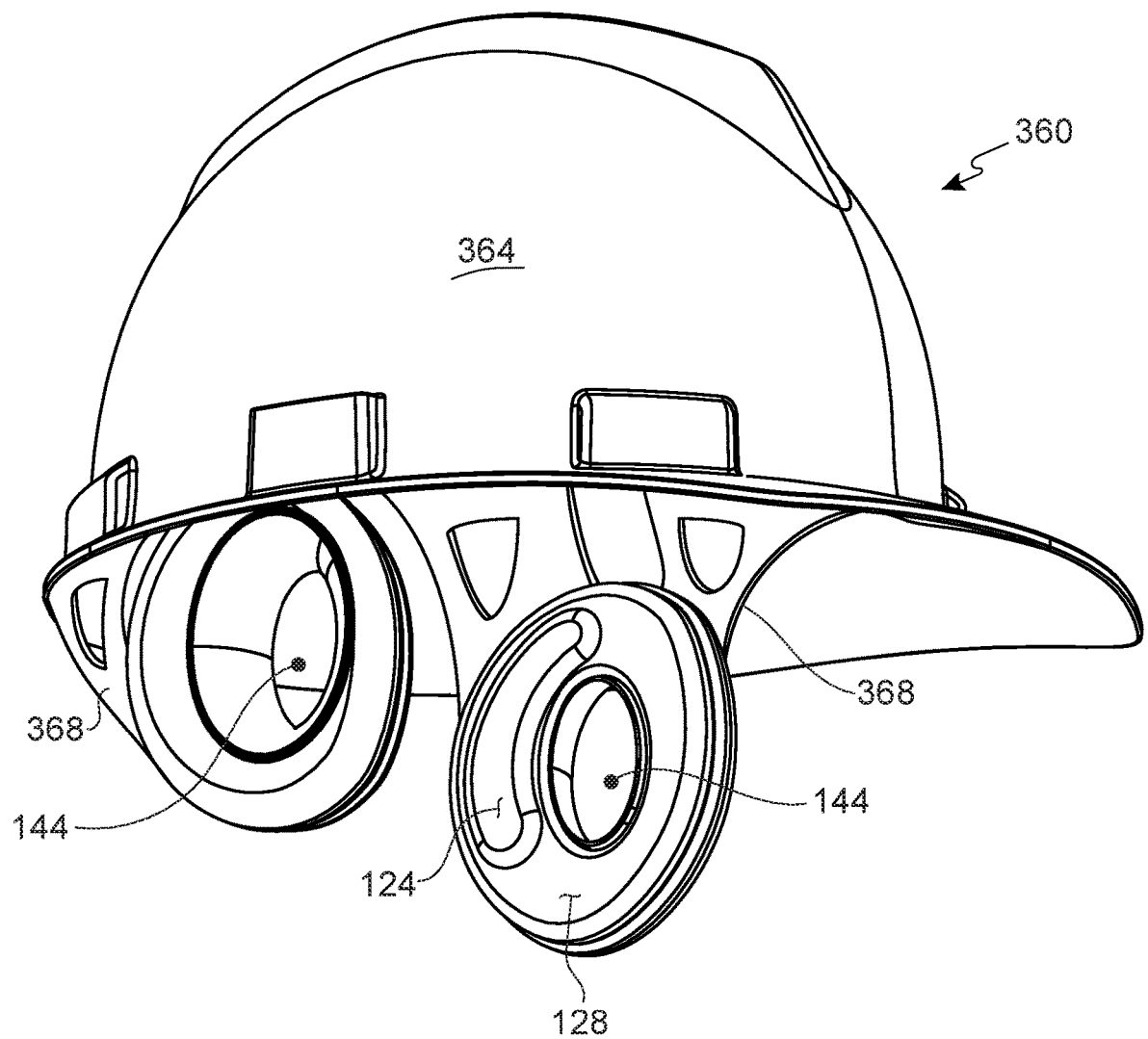
FIG. 37 is a perspective view, slightly from below, looking at the embodiment of FIG. 36.
Figure 38:
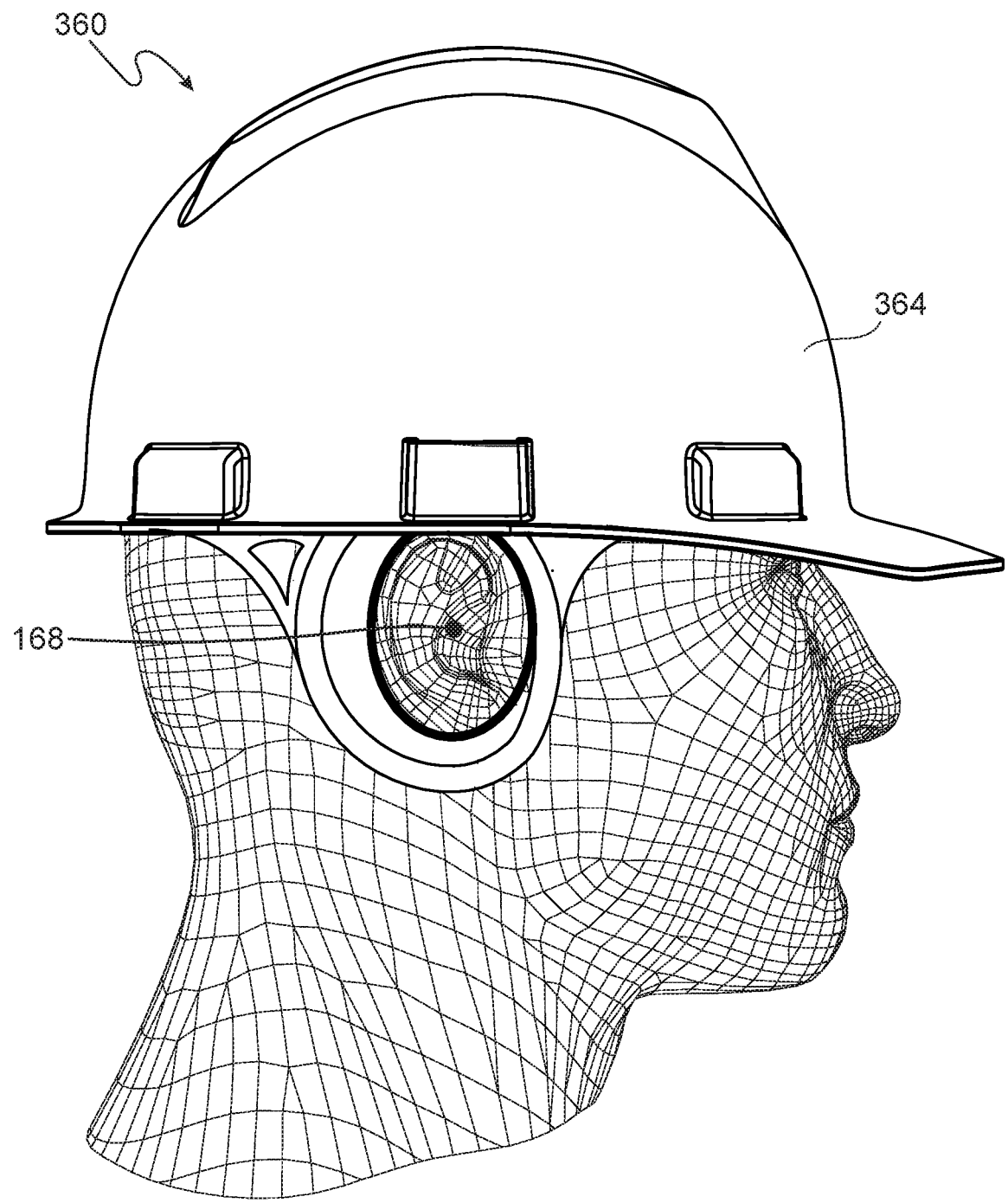
FIG. 38 illustrates the embodiment of FIG. 36 installed on a human head.

FIGS. 36-38 illustrate an alternative assembly, generally 360, including a helmet 364 structured to carry a pair of thermal therapy devices for installation on a human head. A cooling pack mounting band 368 may be adapted to removably hold a pack in position for desired therapy. Desirably, the pack is removable (and sometimes may even be partially dis-assembled) for safe cooling or freezing of one or more removed element.

Figure 39:
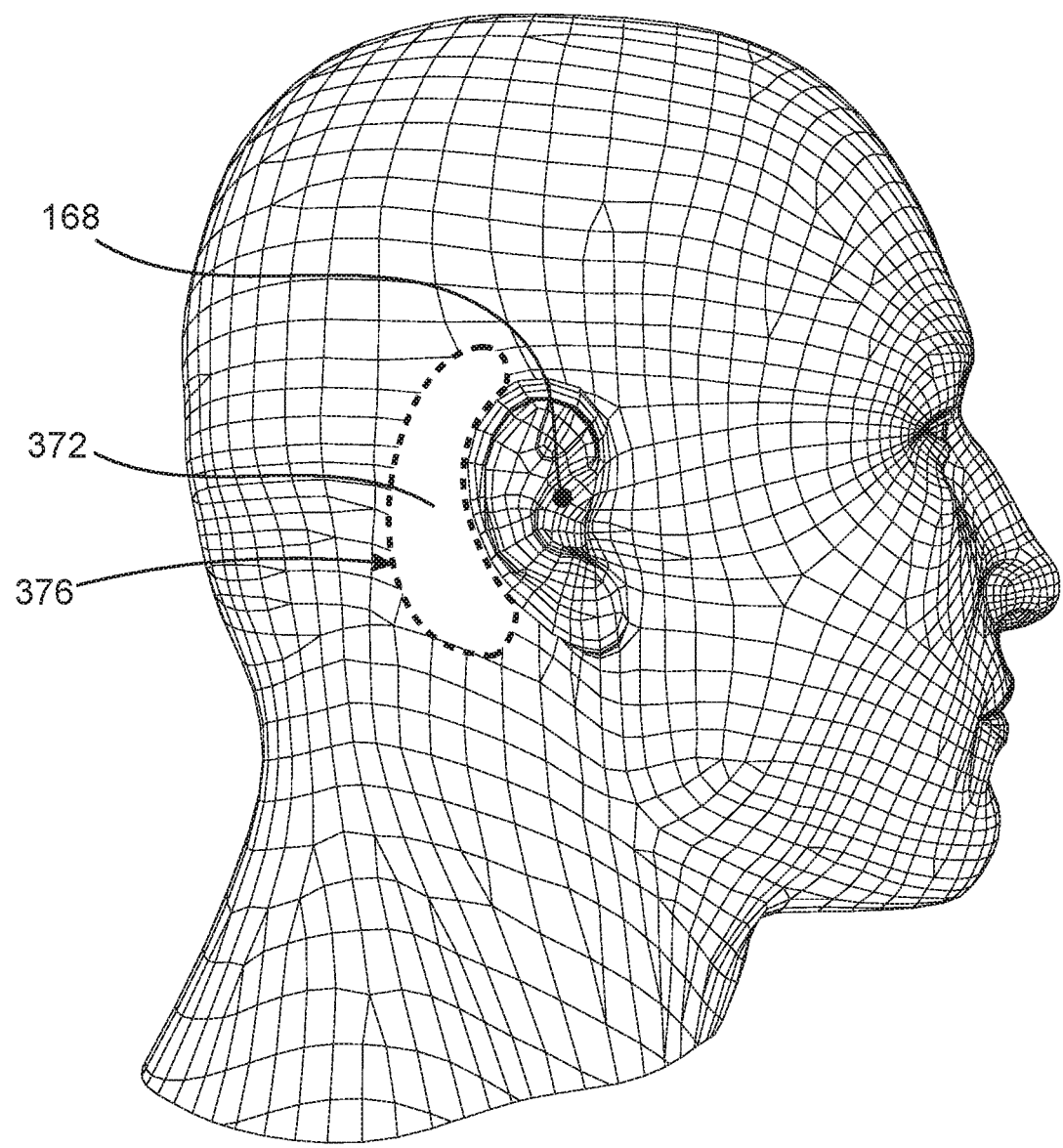
FIG. 39 is a perspective view of a human head indicating a preferred area for application of therapeutic cooling.

FIG. 39 illustrates a desired localized therapy area 372 that is bounded by a perimeter 376. Area 372 is roughly bean-shaped, and may be characterized as an arcuate shape having a center of curvature on the earhole side and extending partially around a circumference of an ear. Area 372 is desirably disposed to approximately abut a posterior ear surface, substantially as close to the ear canal as a thermal therapy device can comfortably fit. It is currently preferred to apply thermal therapy (cooling) only in the localized area 372. Consequently, a contact heat transfer element e.g., cavity 120, is shaped to fit within the perimeter 376. Workable contact shapes for heat transfer patient contact surface 124 include round, rectangular, and arcuate to generally match the bean shape defined by perimeter 376.

Figure 40:
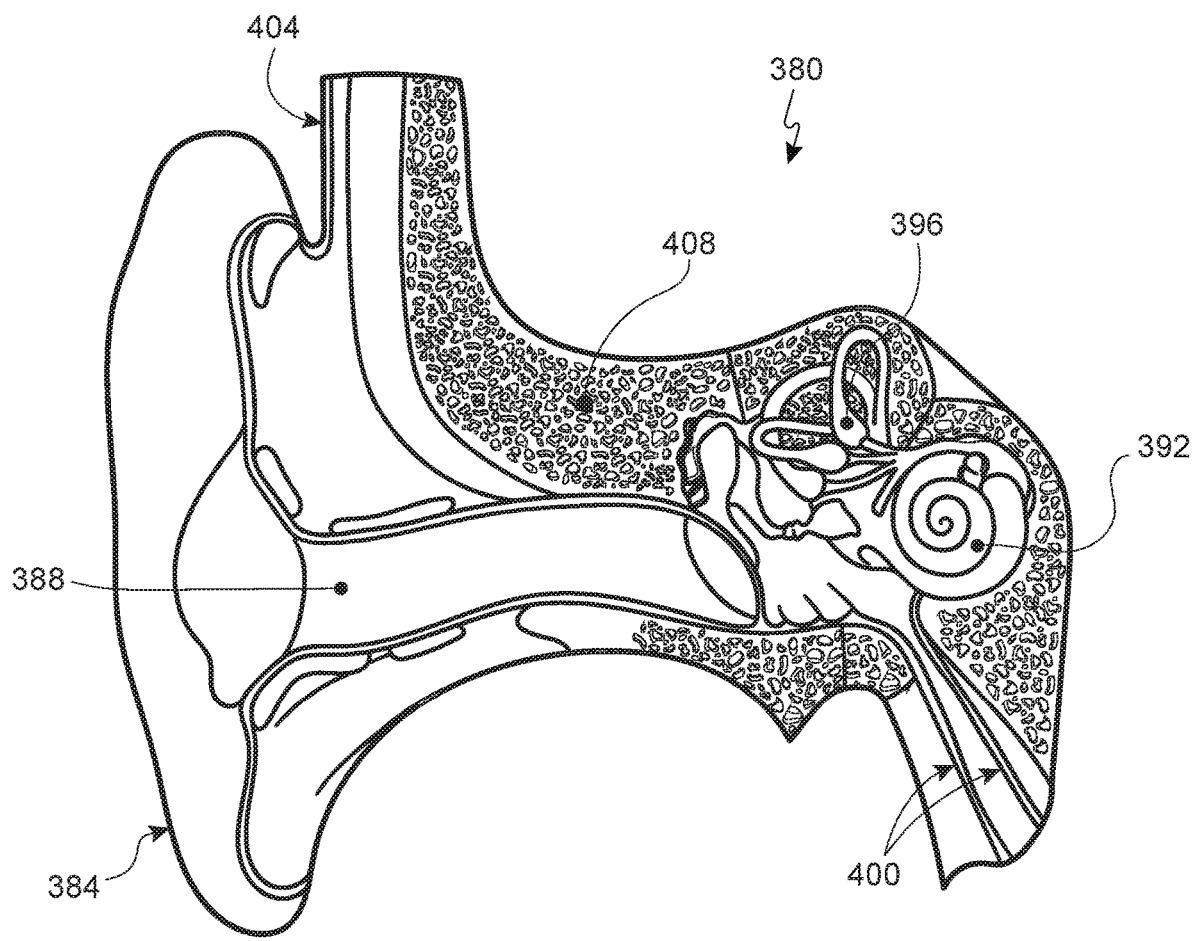
FIG. 40 is a cross-section through a human head illustrating the internal structures effected by cooling therapy.

FIG. 40 illustrates the internal auditory system structures of a human head, generally 380, that are desirably effected by thermal therapy. Inner ear structures 380 include: outer ear 384; ear canal 388; cochlea 392; semi-circular canals (vestibular system) 396; nerve structures (auditory and vestibular 400; skin over the skull 404; and bone of the skull 408. It is believed that currently preferred thermal therapy devices act primarily to transfer heat from the structures of the inner ear by way of conduction through bone 408.

Figure 42:
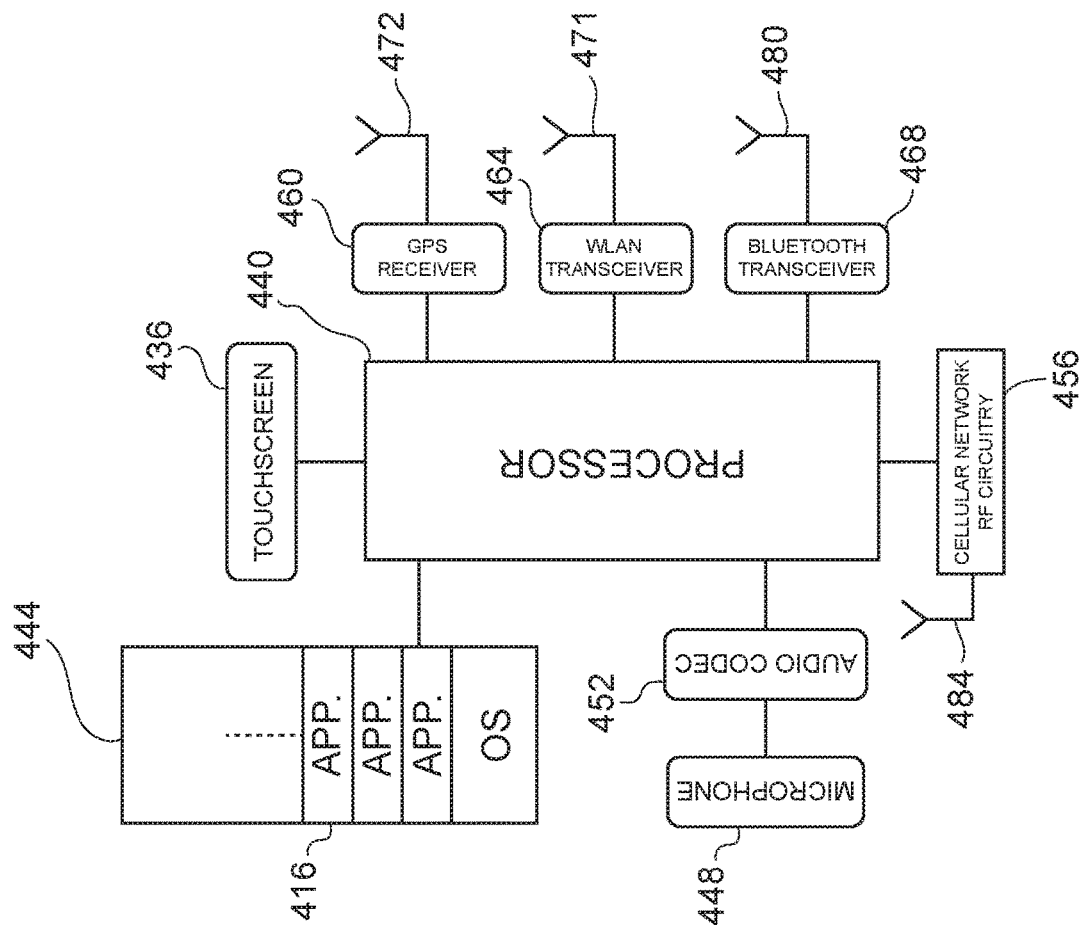
FIG. 42 illustrates an exemplary and workable hardware/software architecture.
Figure 41:
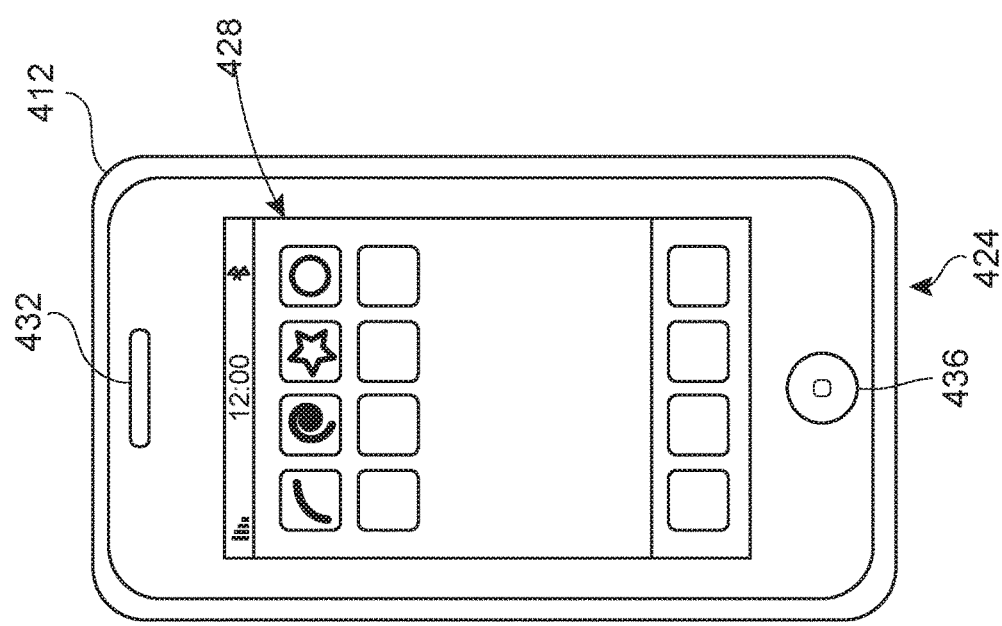
FIG. 41 is a plan view of an exemplary mobile device for use in combination with certain preferred embodiments.
Figure 43:
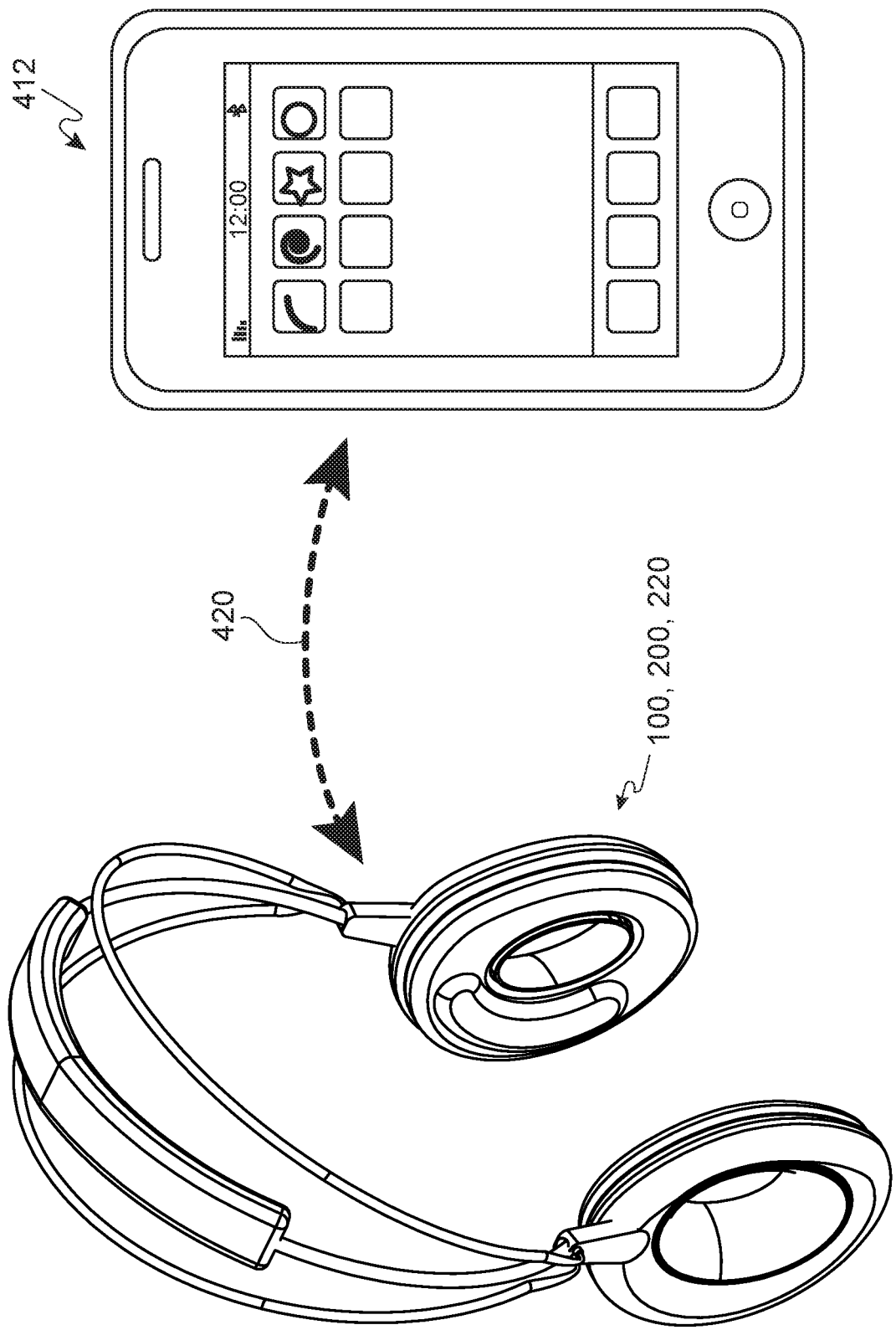
FIG. 43 illustrates communication between an exemplary mobile device and an exemplary therapeutic device

FIGS. 41-43 illustrate an exemplary mobile device platform+software package for interface with embodiments of cooling device(s). For this, a mobile phone 412, with an integrated software application 416, may be structured to communicate (wirelessly or wired) 420 with a cooling device. The communication is desirably 2-way: the cooling device sends/receives data from the mobile device, and the mobile device sends/receives data from the cooling device. Advantageously, a mobile phone includes: a microphone 424; a user interface 428 to convey information to a user; a speaker 432; and a user input control including button 436 to receive input from a user.

An exemplary mobile device platform generally indicated at 412 in FIG. 42 desirably includes: one or more software application(s) 416; a touch screen user input control 436; a microprocessor 440; on-board memory 444; a system microphone 448; an audio codec 452 to compress/decompress audio data; mobile device/cellular network communication circuitry 456; GPS transceiver module 460; wide/local area network (WLAN) transceiver module 464; Bluetooth transceiver 468; GPS antenna 472; WLAN antenna 476; Bluetooth antenna 480; and cellular antenna 484. As indicated generally in FIG. 43, a mobile platform may be placed in cooperation with a therapy device (e.g., passive or active) to monitor, detect, and provide therapy responsive to a perceived sonic event.

Figure 44:
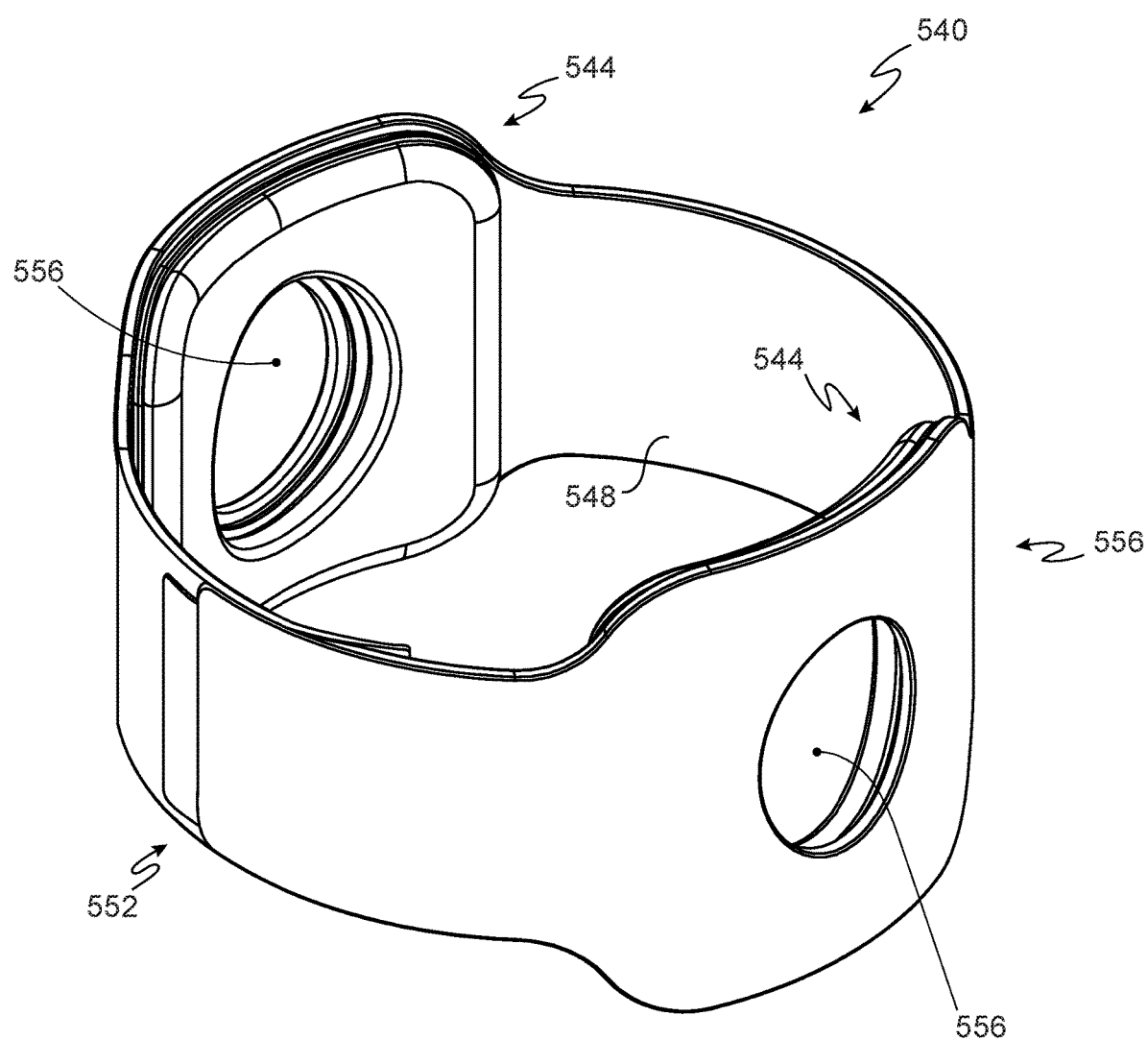
FIG. 44 is a view in perspective of a currently preferred embodiment.

With reference now to FIG. 44, the assembly illustrated generally at 540 includes a pair of spaced-apart cooling packs, generally 544. The cooling packs 544 are illustrated in association with a band 548. In general, a band 548 is operable to hold one or more cooling pack 544 in sufficiently operable registration with a wearer to perform thermal therapy on the wearer.

Preferably, a band 548 is stretchy, regionally stretchy, or may otherwise be adjusted in length to fit comfortably to a human head. Band 548 also desirably possesses sufficient integrity and strength to maintain the cooling packs 544 in compression contact with the head to provide effective heat transfer between the wearer's head and a cooling element of the cooling packs. A workable material of construction for a band 548 includes rubber, Lycra, stretch-faced neoprene, and the like.

A length adjustment mechanism, generally 552, may be provided in some cases. A workable length adjustment mechanism 552 includes hook-and-loop fastener, clasp, snap mechanism, buckle arrangement, pinch mechanism, and the like. It is sometimes desirable for the circumferential spacing between cooling packs 544 to be adjustable, to accommodate to heads of various size. Sometimes, a band may stretch to change the spacing between cooling packs, as desired. Other times, a location of one (or both) cooling pack(s) may be adjustable with respect to the band 548.

Figure 45:
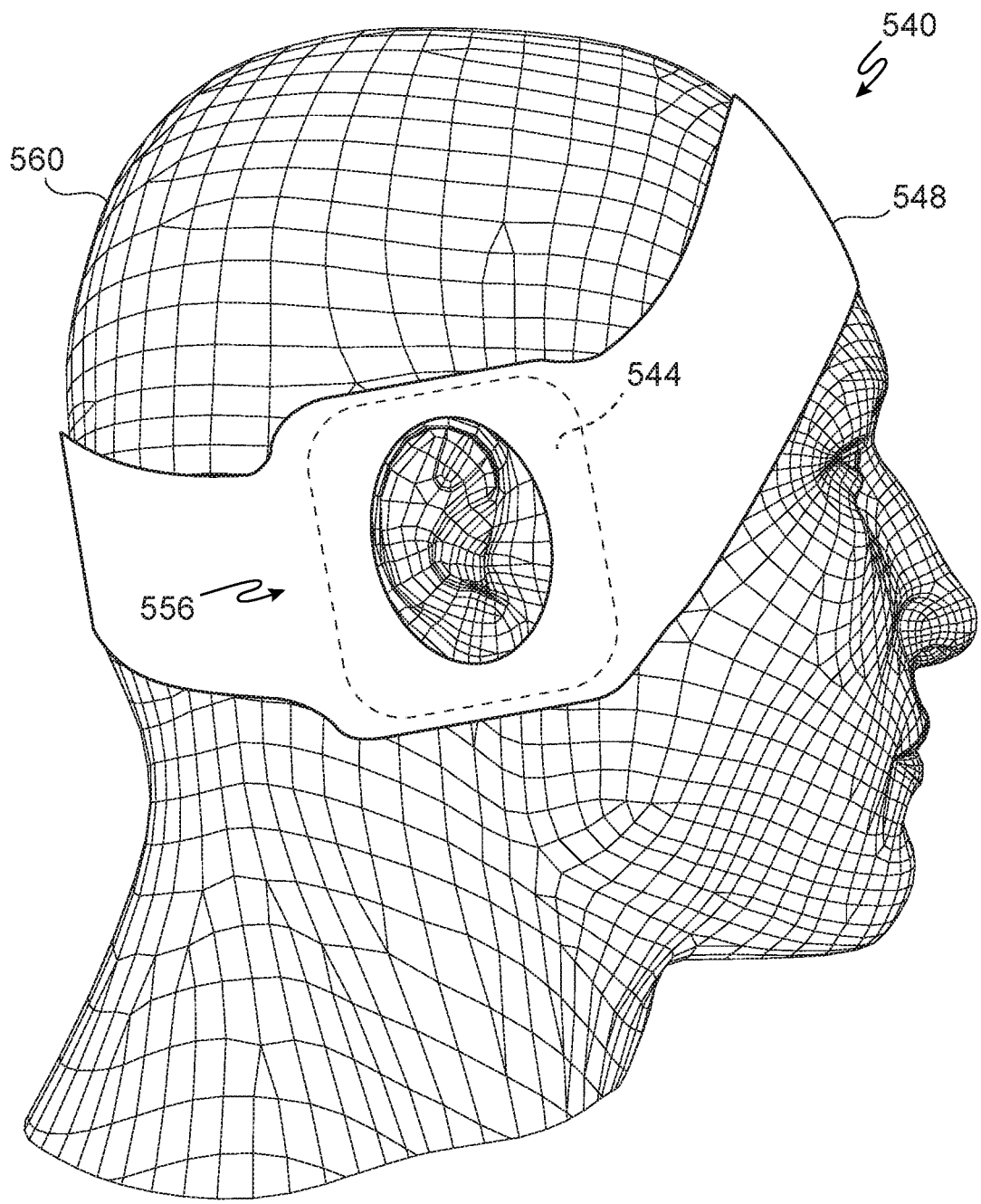
FIG. 45 is an illustration in perspective of the embodiment of FIG. 44 installed on the head of a human.
Figure 46:
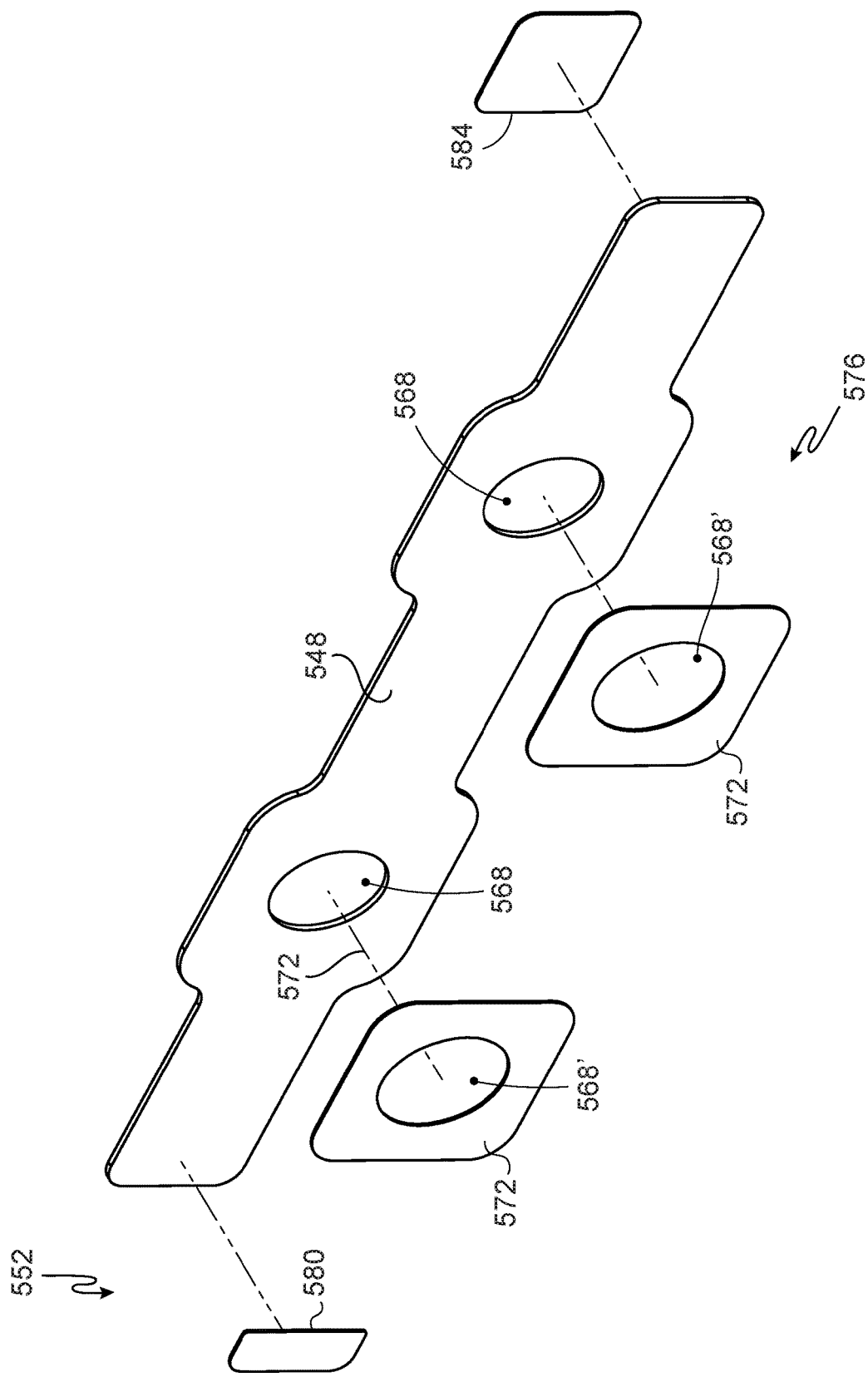
FIG. 46 is an exploded assembly view of certain components of the embodiment in FIG. 44.
Figure 47:
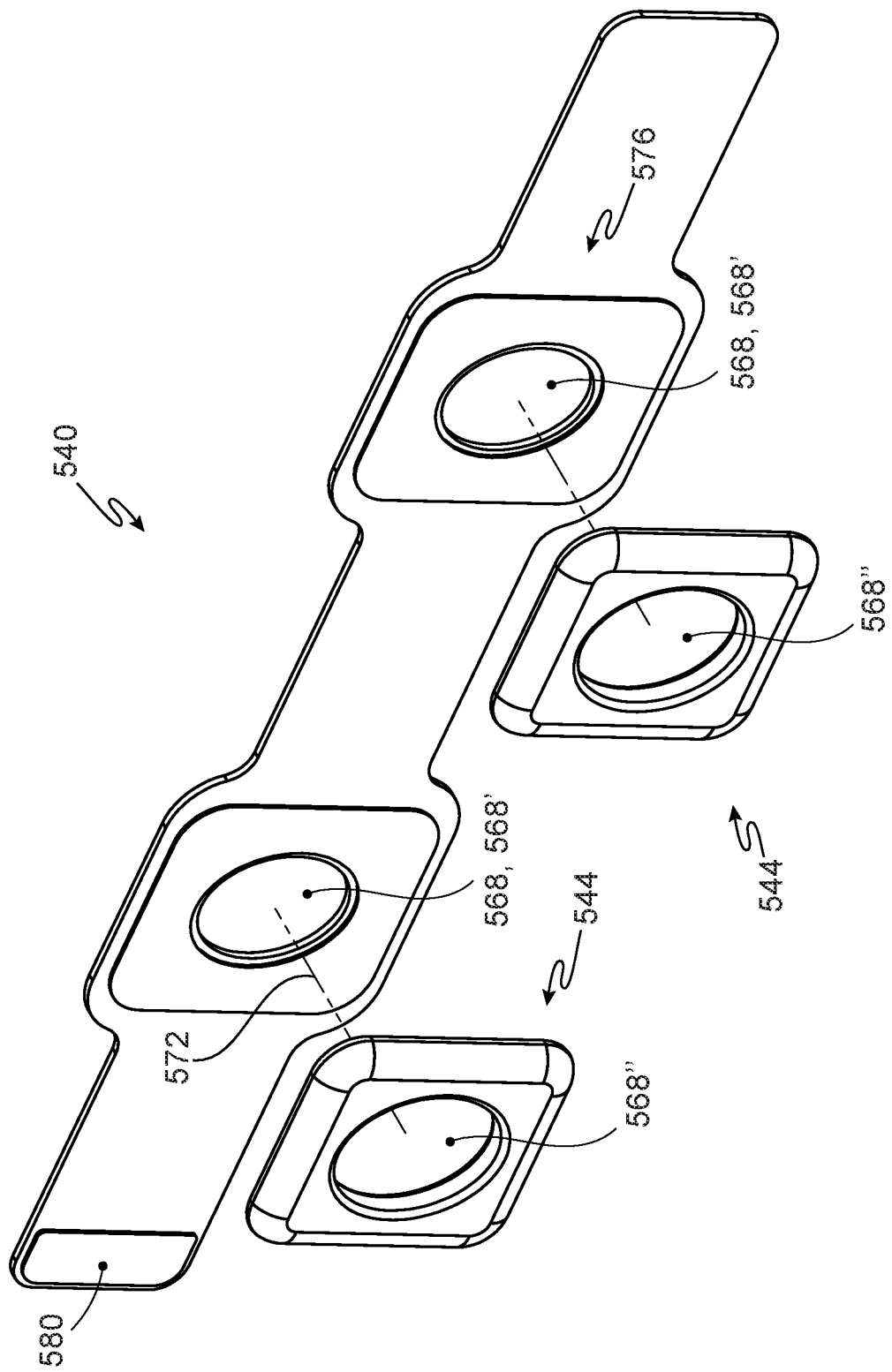
FIG. 47 is an exploded assembly view of additional components of the embodiment in FIG. 44.

Preferred embodiments provide registration structure, generally indicated at 556, to facilitate installing a cooling pack, such as a pack 544, in a desired orientation with respect to the certain structure of the head. As illustrated in FIGS. 44 and 45, one workable registration structure includes a through-tunnel 556 configured to interface comfortably with protruding ear structure of a human wearer 560 of the device 540. The illustrated through-tunnel 556 penetrates an entire cooling pack 544, as well as the band 548. Consequently, the ear canal of the wearer 560 is unobstructed.

Details of construction of an exemplary device 540 will now be explained with reference to FIGS. 46 through 51. A pair of through-holes 568 are formed in the band 548 at locations generally in correspondence with ear locations. Corresponding through-holes 568' are formed in fastening structures 572. A cooperating through-hole 568" is provided by each cooling pack 544. The through-holes 568, 568', and 568" stack in registration to form a through tunnel extending along a tunnel length axis 572.

A fastening structure 576 is configured and arranged to cooperate with a respective cooling pack 544 (FIG. 47), desirably to permit removably affixing the cooling pack in installed registration with respect to the band 548. A workable fastening mechanism 576 may be embodied by a hook-and-loop assembly, a pocket in which to receive a cooling pack, mechanical interference formed between a portion of, or carried by, a pack and cooperating structure of a mechanism 576, and the like.

The illustrated length adjustment mechanism 552 includes one part 580 and the cooperating part 584 of a hook-and-loop assembly. Attachment of a length adjustment mechanism 552 to a band 548 may be accomplished in conventional fashion, as is well known.

Figure 50:
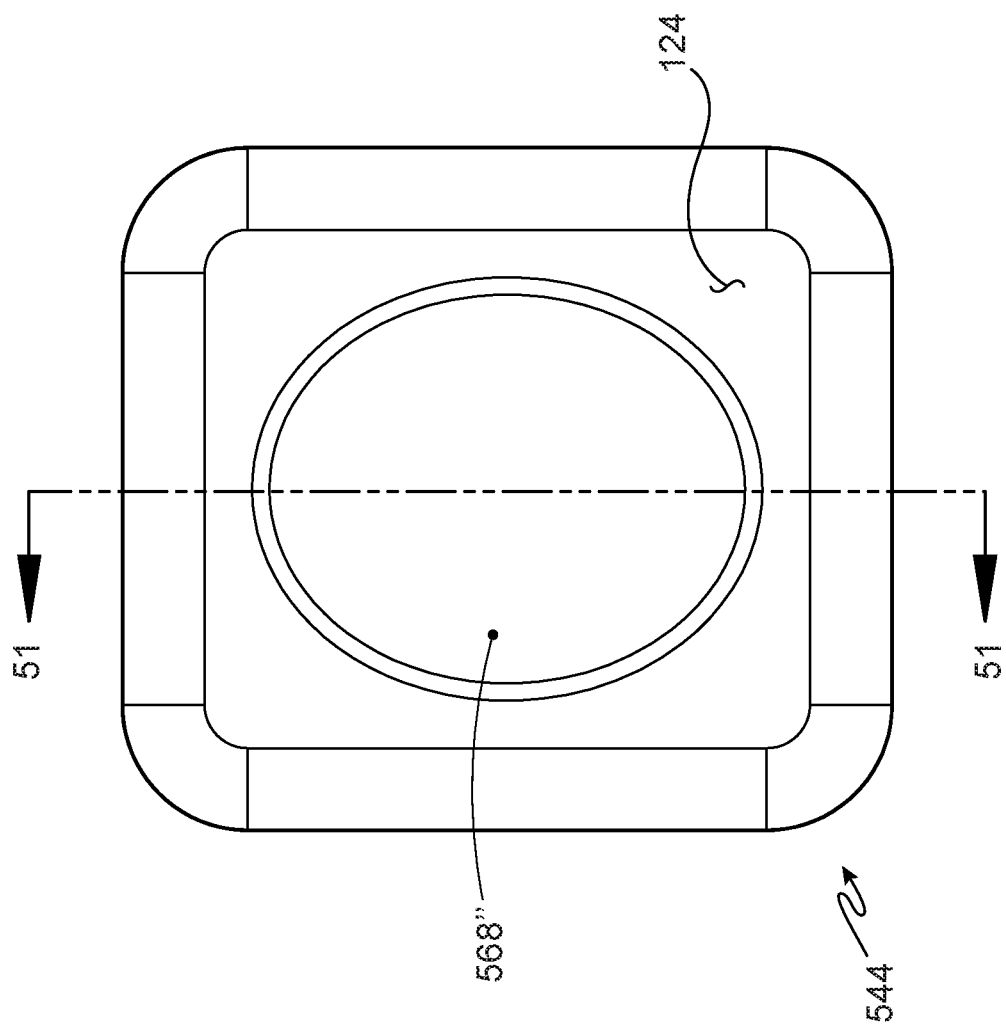
FIG. 50 is a top view of a cooling pack element of the assembly illustrated in FIG. 48.
Figure 51:
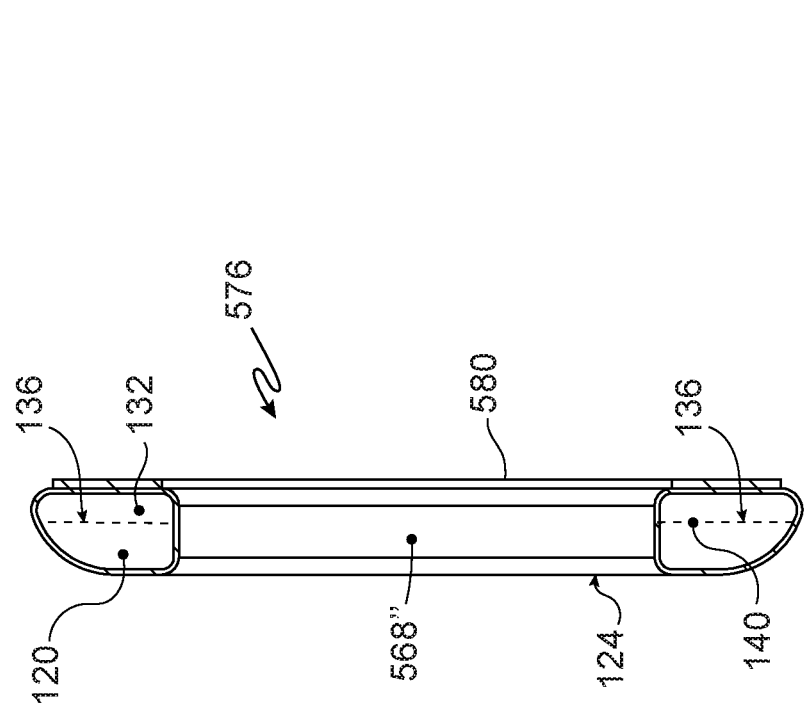
FIG. 51 is a cross-section view taken through section 51-51 in FIG. 50, and looking in the direction of the arrows.

With particular reference to FIGS. 50 and 51, illustrated cooling pack 544 may be constructed similar to cooling packs mentioned above. A contact surface 124 bears on (and desirably adapts in shape to), a heat transferring surface of a wearer, and facilitates transfer of heat from the wearer to fluid confined inside contact heat reservoir 120. A physical boundary, or imaginary boundary 136, may separate contact reservoir 120 from bulk reservoir 132. Again, each cavity 120, 132 may hold a different heat transfer fluid, as desired to convey a particular heat transfer therapy.

Further, any/all embodiments with cooling pack(s) may also include a thermo-electrical device, an electrical circuit with a thermistor (or thermocouple), battery, and electrical hardware/software for monitoring and/or controlling the temperature of the cooling packs, and transmitting the data wirelessly (Bluetooth, Wi-Fi, other) to a mobile computing device or database. Also, portions of a visible surface of a heat transfer element may be printed with a thermochromic ink for temperature indication to the user. Other devices and methods for temperature indication to a user are also within contemplation.

Figure 54:
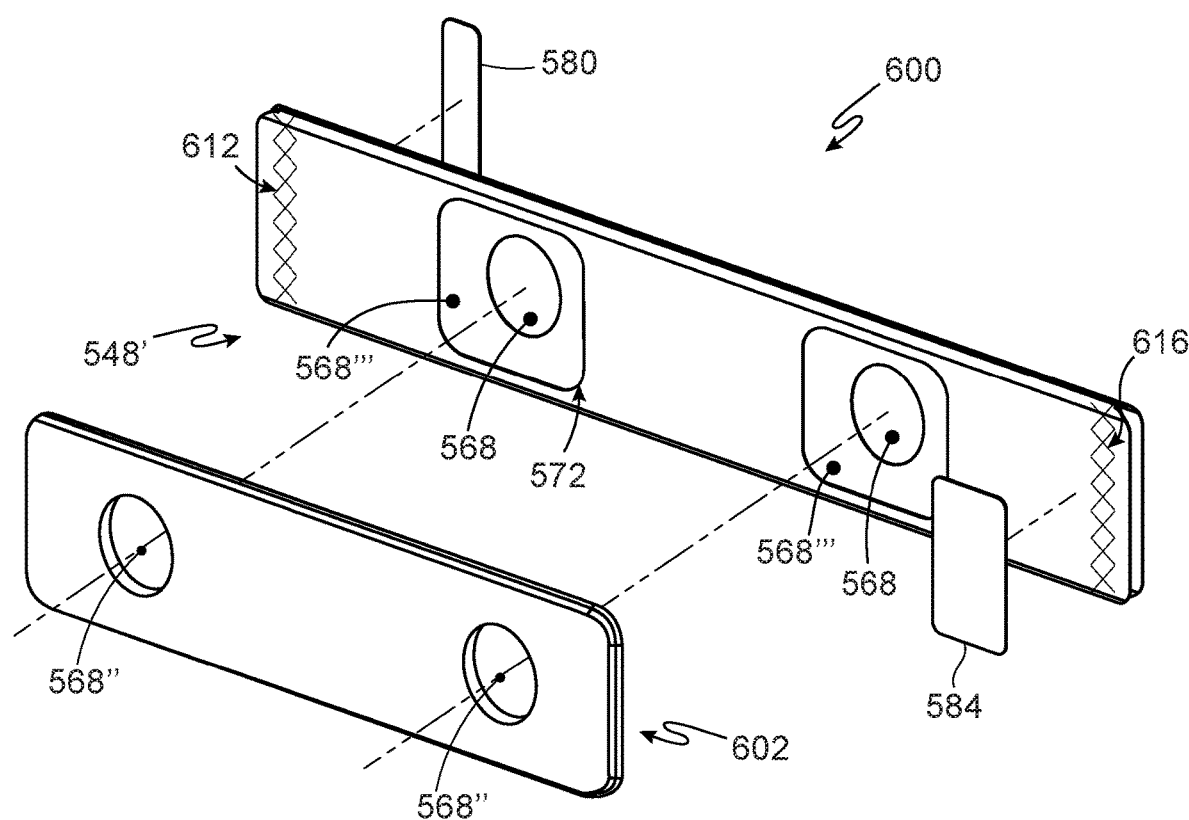
FIG. 54 is an exploded assembly view in perspective of an embodiment incorporating a belt such as the belt in FIG. 50.

The thermal therapy device indicated generally at 600 in FIG. 54 includes a band 548', and a single heat transfer device 602 configured to apply thermal therapy to both ears. A band 548' may be made from a length of tubular stretchy material. Heat transfer element 602 may be placed inside the tube of body 548'. An outer wall of the tubular body may be excised to form a through-hole 568. The inner tube wall may be cut to define an enlarged heat transfer widow 568'.

As illustrated, band 548' may be adjusted in circumferential length by way of an exemplary hook-and-loop arrangement. One part 580 of a fastener arrangement 576 may be affixed to band 548', as indicated by stitching, generally 612. The cooperating part 584 may be affixed to band 548' by way of stitching, generally 616. One or the other of stitching areas 612, 616 may also confine the heat transfer element inside the body. Other workable arrangements are well known.

Certain details of construction and operation of cooling packs that are foldable to form first and second reservoirs (that are disposable to be thermally communicating between each other), are illustrated in FIGS. 55 through 76. The folding cooling pack generally indicated at 640 in FIG. 55 is configured to cost-effectively form a pair of heat transfer reservoirs between planar membranes. As illustrated in FIG. 55, a contact reservoir is provided in cavity 120, and contact surface 124 is configured to extend partially around the circumference of an ear canal. It is within contemplation that the contact reservoir may be configured in alternative ways, e.g., to extend entirely around a canal's circumference, and to provide larger or smaller volumes in a cavity 120.

A cooling pack 640 may advantageously be manufactured from top and bottom plies of polymer film. An exemplary such film may include a foil or metalized film to provide enhanced thermal conductivity. Polymer film is one workable material that may be formed into 3-D shapes, die-, laser-, or water-cut, and thermally welded or otherwise bonded to produce fluid-holding cavities.

Figure 57:
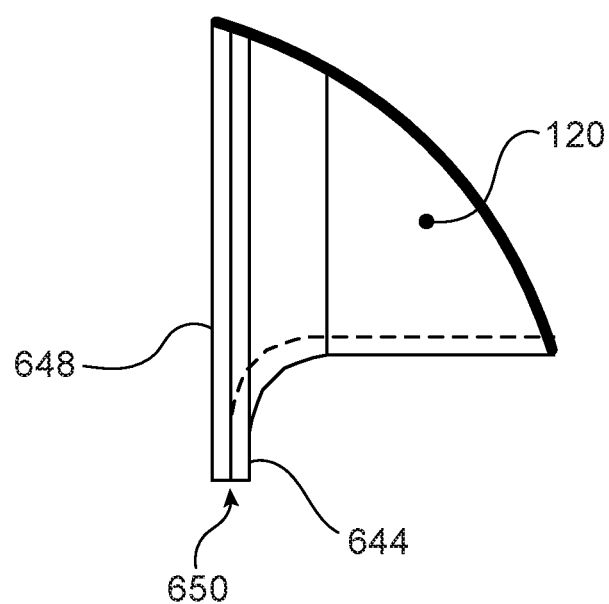
FIG. 57 is a close-up view of the portion indicated by circle 57 in FIG. 56.
Figure 58:
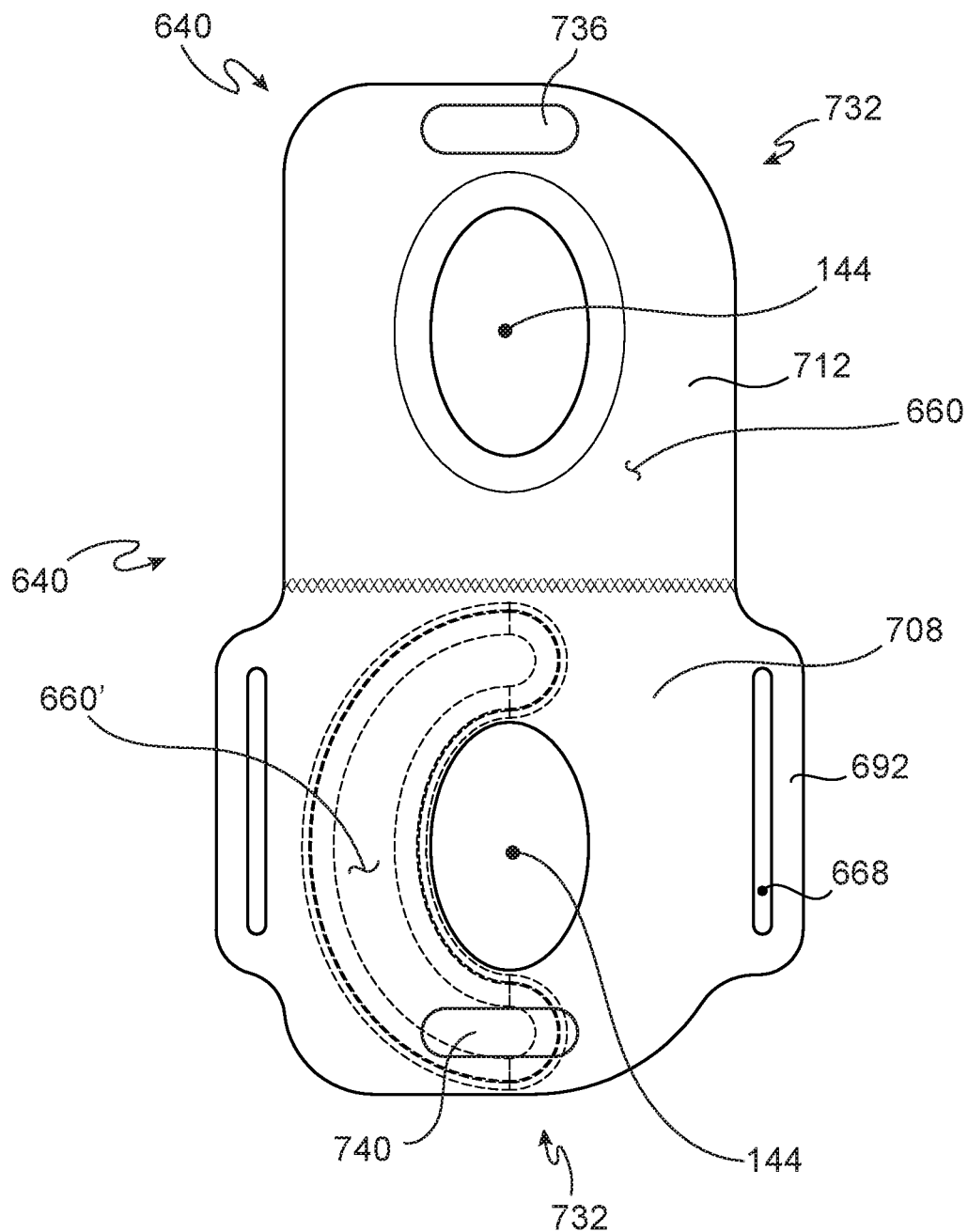

FIG. 57 illustrates top ply 644 bonded to bottom ply 648. Cavity 120 may be provided as a 3-D shape substantially formed in top ply 644. For one nonexclusive example, cavity 120 may be thermoformed into a 3-D structure to substantially define cavity 120. The perimeter of the cavity 120 is sealed by bonding the top and bottom plies 644, 648 to resist escape of heat transfer media from confinement inside cavity 120. A bonded joint formed between the plies, generally 650, may define a fluid-resistant perimeter of a cavity. A similar arrangement produces bulk cavity 132. A hinge, generally 652, is formed between cavity 120 and cavity 132, to permit folding the cavities into selective contact with each other.

A through-hole or tunnel 144 is typically formed to permit the helix of an ear to pass through the contact reservoir portion 120 of device 640. In certain cases, a through-hole 144' is provided to pass completely through the bulk reservoir portion 656 of a foldable cooling pack. In stacked registration, through holes 144, 144' form a through-tunnel passing through the device 640, and thereby provide an unobstructed path through the device 640 to a wearer's ear canal. With particular reference to FIGS. 59, 62 and 67, heat transfer surface 660 may be rotated, as indicated by arrow 664, to selectively contact with cooperating heat transfer surface 660', and thereby form an equivalent barrier element 152 between cavities 120 and 132.

It is sometimes desirable to provide adjusting structure of a cooling pack that is configured in harmony with suspension structure of a pack-application device to permit position-adjustable association of one or more cooling packs with respect to the pack-application device. As a consequence, one or more cooling pack may be positioned to comfortably interface with an ear's helix, and orient a contact heat transfer reservoir 120 in desired registration with a target location of a wearer's head 628 (FIG. 76).

An exemplary pack-position adjusting structure, generally 680, is illustrated in FIG. 55. As shown in FIG. 55, an adjusting structure 680 carried by a cooling pack may be embodied as a belt loop having a perimeter 684 that defines an aperture 688 to receive a belt or strap-like suspension structure or element. A belt loop tab 692 spaces the aperture 688 apart from an edge 696 of the illustrated cooling pack 640.

As previously mentioned, heat transfer reservoirs may be provided having alternative volumes of heat transfer media. The embodiment 640' illustrated in FIGS. 60 and 61 includes a bulk reservoir 132' that lacks a through-hole. Consequently, and by visual inspection, the volume disposed inside cavity 132' can be larger than, for example, cavity 132 in FIG. 55.

The end view illustrated in FIG. 64 shows how a folded embodiment may sometimes define a cavity 704 disposed between a front or inner part (sometimes made reference to as bladder 1), generally 708, and a rear or outer part (sometimes made reference to as bladder 2), generally 712, of a folding embodiment 640. In certain cases, a suspension structure, generally 716, may be disposed inside cavity 704. In such cases, a portion of suspension element 716 may also provide a thermal barrier to thermal communication between contact cavity 120 and bulk cavity 132. The suspension structure 716 may cause a compression, generally indicated at 720, to be exerted by contacting heat transfer surface 124 onto a portion of the wearer's head.

An exemplary suspension structure 716 illustrated in FIG. 65 includes belt or band 720. A workable belt 720 may include one or more through-hole 144", to receive a helix in penetration there-through. A through-hole having an alternative extended length is pointed out by 144'''. It can be advantageous to provide an elongated through-hole of the type indicated by 144''', to permit adjusting a position of a cooling pack at a desired position along a length of the band 720, as indicated by arrow 724.

As illustrated in FIG. 66, band 720 may be woven through pack-position structure 680 to dispose a belt loop tab 692 on the opposite side of the band 720 from contact surface 124. As illustrated in FIG. 64, the suspension structure 716 (e.g., band 720) may be disposed between front part (or bladder 1) 708 and rear part or (bladder 2) 712. In another configuration illustrated in FIG. 67, the front and rear parts 708, 712 are in direct contact, and the band 720 is disposed on the opposite side of the belt loop tab 692 compared to both front and rear parts 708, 712. Consequently, the band 720 presses onto bladder 2 (shown by distributed force 724), and the heat transfer contact surface 124 of bladder 1 presses on the user's head (shown by distributed force 720).

Sometimes, an anti-flop mechanism, generally 732 (FIG. 58), may be included in a folding cooling pack, such as pack 640. A workable mechanism 732 may include a catch element 736 carried by one portion 712, and a latch 740 carried by the other portion 708. An anti-flop mechanism 732 can be embodied as a hook-and-loop assembly, or a magnet and magnetically-attracted counterpart, and the like. An anti-flop mechanism 732 may be disposed in any location that is operable. For example, a mechanism 732 that forms a structural interference would be located at respective positions on front and rear portions 708, 712, that permit coupling of the catch and latch elements. In certain cases, coupling between a catch and latch may occur regardless of an intervening element, such as band 720.

FIGS. 77 through 79 illustrate details of construction and operation of an alternative embodiment of a thermal therapy device, generally indicated at 760. A device 760 may include constituent elements having internal structure that operates in similar fashion to those described above, in relation to other embodiments. For example, device 760 includes a band 764, and a pair of cooling packs 768. An exemplary cooling pack may be formed from a pair of polymer membrane sheets, as discussed above, and include a contact heat transfer surface 124. An attachment portion 772 may be provided by membrane sections, typically in an area lacking a heat transfer media cavity. An aperture 144 desirably communicates through each cooling pack to accommodate disposition of an ear helix there-through. Typically, a cooperating aperture 774 communicates through the band 764, to provide an unobstructed ear canal for a wearer of device 760.

Suspension structure, generally 716, is configured to create a length adjustable band 764, and includes a plurality of sub-portions that individually may provide a different functionality. Band 764 includes a left wing flap 776, a resilient panel 780, a head support panel 784, a resilient panel 788, and a right wing flap 792. Typically, left and right wing flaps are relatively stiff, to not stretch significantly as the device 760 is attached to a wearer's head. A workable wing flap may be manufactured of neoprene, or similarly transversely compliant material having some stretch. A transversely compliant wing flap made from such a membrane-like element is operable to fit comfortably in contact with the varying head shape expected from a population of human heads. However, it is desirable that a wing flap stretch in length under tension to a lesser degree than certain other band elements. Sub-portions of a band (wing flap, panels, supports, adjustment mechanisms, etc.) may be affixed to each other in accordance with well-known arrangements, including welding, adhesive joints, and stitching with needle and thread. Panels 780, 788 can also be created by stitching band 764 in specific areas, with specific stitch geometries to effect mechanical stretch of the band 764.

One or more resilient panel 780, 788 provides primarily for extension of suspension structure 716 in a circumferential length of the band 764, and to facilitate orienting cooling packs 768 in registration with ear protrusions (helixes) of a wearer. Optional head support element 784 is typically not as resilient or stretchy as a resilient panel 780, 788. Workable resilient panels may include Lycra or Spandex material, or some other similarly elastic and extensible element. The illustrated band 764 includes cooperating parts of a hook-and-loop fastener assembly to effect a circumferential band length change. Alternative arrangements to adjust a circumferential length of a band 764 are within contemplation.

Desirably, cooling packs are affixed to the band 764 at one end, and their opposite end portion is free to move with respect to the band 764. Such an arrangement permits an aperture 144 to remain in registration with an ear as the circumferential length of a band is adjusted. As illustrated in FIG. 79, exemplary cooling pack 768 is affixed at its anterior end (e.g., at a weld, stitch line, etc., 796) to wing 792. In that case, the posterior end can slide with respect to the band as the band circumference is changed in length. In the illustrated embodiment, cooperating hook-and-loop portions 580, 584 provide adjustment in a length of band 764 that spans circumferentially between the anterior ends of cooling packs 768. Presence of at least one stretchy panel 780 operates to regulate the circumferential spacing between the posterior ends of the cooling packs responsive to tension in the band 764 (e.g., to increase or decrease spacing between packs depending on band tension).

Sometimes, openings 772 of a wing flap are oversized (as illustrated), compared to corresponding openings 144 in respective cooling packs. As illustrated, a covering for a portion of an oversized aperture may carry a logo, or other element, that may be imprinted with thermochromic ink to provide an indication of operating temperature of a cooling pack. Because the covering occupies a portion of the oversize opening, it may register against the heat transfer element of a cooling pack, and provide real-time cooling pack temperature feedback.

While aspects of the invention have been described in particular with reference to certain illustrated embodiments, such is not intended to limit the scope of the invention. The present invention may be embodied in other specific forms without departing from its spirit or essential characteristics. For one example, one or more element may be extracted from one described or illustrated embodiment and used separately or in combination with one or more element extracted from one or more other described or illustrated embodiment(s), or in combination with other known structure. The described embodiments are to be considered as illustrative and not restrictive. Obvious changes within the capability of one of ordinary skill are encompassed within the present invention.

The scope of the invention for which a monopoly position is currently desired is indicated by the appended claims rather than by the foregoing description. All changes which come within the meaning and range of equivalency of the claims are to be embraced within their scope.

What is claimed is:

1. An apparatus, comprising:
a first cooling pack comprising a first heat transfer element with a first contact surface and a first pack aperture to a first tunnel, the first tunnel communicating from the first contact surface through a first thickness of the first pack;
a second cooling pack comprising a second heat transfer element with a second contact surface and a second pack aperture to a second tunnel, the second tunnel communicating from the second contact surface through a first thickness of the second pack;
a band comprising a band thickness between a band inside surface and a band outside surface, the band being adjustable in length along a band circumference to accommodate human heads of various sizes in reception within the band circumference, the first and second cooling pack being carried by the band for application of thermal therapy to the head of a human wearer of the band; wherein:
the first and second tunnels communicate from respective first and second contact surfaces to at least an inside surface of the band, the first and second tunnels to receive a helix portion of a human ear therein, and wherein:
the first and second tunnels communicate from respective first and second contact surfaces through the band thickness.

2. The apparatus according to claim 1, wherein:
each of the first and second cooling pack comprises a second thickness disposed on the opposite side of the band from the respective first thickness; and
the first and second tunnels further extend through the second thickness of each respective cooling pack.

3. The apparatus according to claim 1, wherein:
the first cooling pack and the second cooling pack are removably affixable to the band at a plurality of operable locations disposed around the band circumference to dispose the first and second tunnels in agreement with respective left and right ears of a user such that each respective tunnel may receive protruding portions of a human ear to permit the first and second contact surfaces to be disposed in contact with the user's head in the vicinity of the user's respective left and right ear canals.

4. The apparatus according to claim 1, further comprising:
a holding mechanism configured to permit adjusting a held position of at least one of the first cooling pack and the second cooling pack with respect to the band to operably align a band aperture in the band and a pack aperture in the at least one of the first and second cooling packs, the aligned band aperture and pack aperture to receive the helix portion in penetration there-through.

5. The apparatus according to claim 4, wherein:
the holding mechanism comprises a hook-and-loop connection between the pack and the band.

6. The apparatus according to claim 4, wherein:
the holding mechanism comprises a belt loop connection between the pack and the band, the belt loop connection comprising a belt loop aperture spaced apart from a cooling pack edge to define a belt loop tab, the band being installed in penetration through the belt loop aperture.

7. The apparatus according to claim 6, wherein:
the first cooling pack comprises a first bladder and a second bladder, the first and second bladder being spaced apart by a foldable element to permit juxtaposition of a thermally conductive face of the first bladder and a thermally conductive face of the second bladder.

8. The apparatus according to claim 7, wherein:
the belt loop tab is disposed on the opposite side of the band from the first contact surface.

9. The apparatus according to claim 7, wherein:
the belt loop tab is disposed on the opposite side of the band from the first bladder and the second bladder.

10. The apparatus according to claim 1, wherein:
the first cooling pack and second cooling pack are permanently affixed to the band at respective operable locations of the band circumference, and the band is structured to dispose the first and second tunnels in agreement with respective left and right ears of a user such that each respective tunnel may receive protruding portions of a human ear to permit the first and second contact surfaces to be disposed in contact with the user's head in the vicinity of the user's respective left and right ear canals.

11. The apparatus according to claim 1, wherein:
the band comprises a multi-part adjustment mechanism operable to change a circumferential length of the band.

12. The apparatus according to claim 11, wherein:
the multi-part adjustment mechanism comprises a hook-and-loop fastener assembly.

13. The apparatus according to claim 11, wherein:
the band is configured such that operation of the multi-part adjustment mechanism to effect a change in the band circumference primarily causes a corresponding change in a circumferential distance between posterior ends of respective first and second cooling packs.

14. The apparatus according to claim 11, wherein:
the band is configured such that operation of the multi-part adjustment mechanism to effect a change in the band circumference primarily causes a corresponding change in a circumferential distance between anterior ends of respective first and second cooling packs.

15. The apparatus according to claim 11, wherein:
the band comprises an oversize through-hole to permit displacement/cooperating alignment of a cooling pack tunnel with an ear canal of the wearer.

16. The apparatus according to claim 11, wherein:
the band comprises portions of varying extensibility to permit modification of a circumferential length disposed between anterior ends or posterior ends of the first and second cooling packs.

17. The apparatus according to claim 11, wherein:
the first cooling pack is structured in cooperation with the band to trap one layer of a multi-layer cooling pack between a wearer's head and the band.

18. The apparatus according to claim 11, wherein:
the first cooling pack is structured in cooperation with the band to trap both layers of a 2-layer cooling pack between a wearer's head and the band.

19. An apparatus, comprising:
a first cooling pack comprising a first heat transfer element with a first contact surface and a first pack aperture to a first tunnel, the first tunnel communicating from the first contact surface through a first thickness of the first pack;
a second cooling pack comprising a second heat transfer element with a second contact surface and a second pack aperture to a second tunnel, the second tunnel communicating from the second contact surface through a first thickness of the second pack;
a band comprising a band thickness between a band inside surface and a band outside surface, the band being adjustable in length along a band circumference to accommodate human heads of various sizes in reception within the band circumference, the first and second cooling pack being carried by the band for application of thermal therapy to the head of a human wearer of the band; wherein:
the first and second tunnels communicate from respective first and second contact surfaces to at least an inside surface of the band, the first and second tunnels to receive a helix portion of a human ear therein, and wherein:
each of the first and second cooling pack comprises a first and a second bladder, each such first and second bladder being spaced apart by a foldable element to permit juxtaposition of a thermally conductive face of the first bladder and a thermally conductive face of the second bladder.

* * * * *